United States Patent [19]

Yabe et al.

[11] Patent Number: 5,536,235

[45] Date of Patent: Jul. 16, 1996

[54] ENDOSCOPE APPARATUS OF ENDOSCOPE COVER TYPE

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Toshiyuki Kubonoya, Koganei, all of Japan

[73] Assignee: Olympus Optical Co., Ltd., Tokyo, Japan

[21] Appl. No.: 35,255

[22] Filed: Mar. 22, 1993

[30] Foreign Application Priority Data

Feb. 9, 1993 [JP] Japan ................. 5-003618 U
Feb. 9, 1993 [JP] Japan ................. 5-003619 U
Feb. 9, 1993 [JP] Japan ................. 5-003620 U

[51] Int. Cl.$^6$ ............................................. A61B 1/00
[52] U.S. Cl. .................... 600/121; 600/139; 138/118
[58] Field of Search ................. 128/4; 138/118, 138/118.1, 124, 125, DIG. 7, 177; 600/139, 144, 121, 123

[56] References Cited

U.S. PATENT DOCUMENTS

| Re. 34,110 | 9/1992 | Opie . | |
|---|---|---|---|
| 3,162,190 | 12/1964 | Del Gizzo . | |
| 4,646,722 | 3/1987 | Silverstein | 128/4 |
| 4,690,175 | 9/1987 | Ouchi et al. | 128/4 X |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,899,787 | 2/1990 | Ouchi et al. | 128/4 X |
| 4,907,395 | 3/1990 | Opie | 53/434 |
| 4,919,112 | 4/1990 | Siegmund | 128/4 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi et al. | 128/4 |
| 5,058,567 | 10/1991 | Takahashi | 128/4 |
| 5,199,417 | 4/1993 | Muller et al. | 128/4 X |
| 5,217,002 | 6/1993 | Katsurada et al. | 128/4 |

FOREIGN PATENT DOCUMENTS

| 0184778 | 6/1986 | European Pat. Off. . |
| 0310515 | 4/1989 | European Pat. Off. . |
| 0338567 | 10/1989 | European Pat. Off. . |
| 0341719 | 11/1989 | European Pat. Off. . |
| 0341718 | 11/1989 | European Pat. Off. . |
| 0349479 | 1/1990 | European Pat. Off. . |
| 0440254 | 8/1991 | European Pat. Off. . |
| 0440252 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-29635 | 2/1991 | Japan . |
| 3-37030 | 2/1991 | Japan . |
| 3-37029 | 2/1991 | Japan . |
| 3-29634 | 2/1991 | Japan . |
| 3-221024 | 9/1991 | Japan . |
| 3-101903 | 10/1991 | Japan . |
| 3-101901 | 10/1991 | Japan . |
| 3-101902 | 10/1991 | Japan . |
| 3-101904 | 10/1991 | Japan . |
| 3-101907 | 10/1991 | Japan . |
| 3-101906 | 10/1991 | Japan . |
| 3-101905 | 10/1991 | Japan . |
| 4-325138 | 11/1992 | Japan . |
| 5-277061 | 10/1993 | Japan | 128/4 |

Primary Examiner—Richard J. Apley
Assistant Examiner—Beverly M. Flanagan
Attorney, Agent, or Firm—Armstrong, Westerman, Hattori, McLeland & Naughton

[57] ABSTRACT

An endoscope apparatus of an endoscope cover type using an endoscope cover comprises an endoscope having a long and narrow insertion tube, and an endoscope cover covering at least an endoscope insertion tube. In the endoscope apparatus, flexibility varies in a direction of a longitudinal axis of at least one of the endoscope and the endoscope cover.

3 Claims, 40 Drawing Sheets

○ HARDNESS-LOW
▲ HARDNESS-HIGH

FIG.16
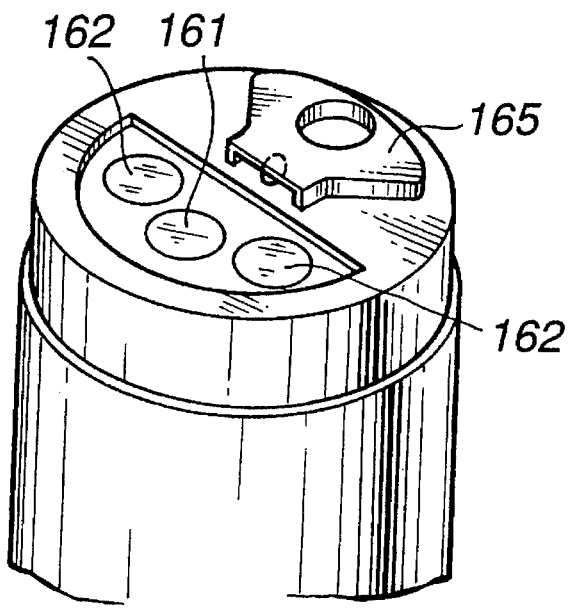
FIG.17
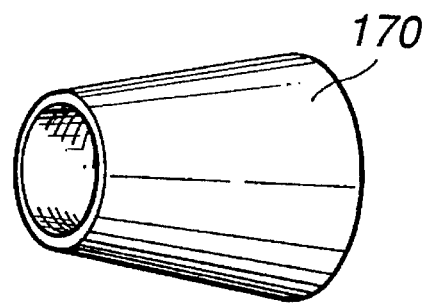
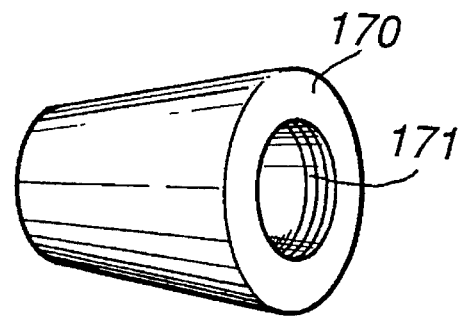

s,536,235

ENDOSCOPE APPARATUS OF ENDOSCOPE COVER TYPE

BACKGROUND OF THE INVENTION

1. Field of the Invention

The present invention relates to an endoscope apparatus of an endoscope cover type which uses an endoscope cover to prevent the endoscope from being contaminated and, more particularly, to prevent the contamination of the structure of an insertion tube inserted into an object position to be examined and of the portion adjacent to the object position.

2. Description of the Related Art

Recently, endoscopes have been widely used in the field of medical treatment. When an endoscope used in the field of medical treatment is inserted into a living body, an observation window provided at the tip of an insertion tube is sometimes soiled by bodily fluid, so that it becomes difficult for the endoscope to observe the inside of the living body. Therefore, an endoscope is provided with an air supplying channel or water supplying channel so as to be able to remove the bodily fluid adhered to the observation window by spraying the observation window with fluid, such as washing water and washing gas, which is operated from the proximal end portion of the endoscope. Further, an endoscope is provided with a sucking channel so as to be able to discharge unnecessary bodily fluid. Also, another endoscope is provided with a forceps channel (treatment tool channel) so as to be able to gather tissues by means of biopsy forceps or to be able to give treatment using treatment tools.

For an endoscope examination, a clean endoscope which is sufficiently washed and disinfected before the examination should be used. Thus, when the endoscope provided with a channel such as a supplying gas channel or forceps channel is applied to a patient, the endoscope is washed or disinfected in order to prevent infection. However, it requires a lot of time to wash and disinfect an endoscope completely, which reduces the efficiency of the endoscope.

Therefore, an endoscope apparatus of an endoscope cover type has been considered. In the endoscope apparatus, an endoscope itself is covered with an endoscope cover to be used. Then, the cover is used once and thrown away after used, and then, exchanged. The endoscope itself is kept clean after use and does not require washing and disinfecting.

As an endoscope apparatus of an endoscope cover type for example, U.S. Pat. Nos. 4,646,722 and 3,162,190 disclose an apparatus in which an endoscope insertion tube is inserted into a cover and the insertion tube is covered with the cover to be insulated from surroundings.

A forceps channel and supplying gas and water channels provided in the endoscope heretofore in use might be soiled by bodily fluid and these channels are long and narrow, so that it requires a lot of time to wash and disinfect these channels. Thus, the endoscope cover is provided with a forceps channel and gas and water supplying channels to prevent the endoscope body inserted into the channels from becoming unclean.

In such an endoscope of an endoscope cover type, the insertion tube is washed or disinfected before the tube is inserted. Then, while the insertion tube is kept being covered with an endoscope cover, the tube is inserted into a body cavity of a patient to examine the body cavity and give treatment to the patient. After use, the endoscope cover is removed and thrown away. In this way, an endoscope cover is used only once for a patient and thrown away, therefore, the endoscope is not required to be washed and disinfected, so that the endoscope can be kept clean and is very easily used. Thus, without being washed or disinfected, the endoscope can be continuously used.

However, in the endoscope apparatus of the aforesaid endoscope cover type, no proposal about the construction material which affects the characteristic of an insertion tube, such as flexibility, elasticity and stability, has been supplied. Therefore, in a case in which the endoscope apparatus of an endoscope cover type was inserted deeply inside the object to be examined, the proximal end portion of the insertion tube was bent when the insertion tube was inserted into the body cavity, so that it happened sometimes that the tube could not be easily inserted into it. In a case in which the tube was inserted into the intestines, there was a problem of a difficult inserting operation because the tip of the insertion tube could not be bent along the intestines producing pain in the patient.

If the aforesaid insertion tube was bent to an extreme degree when inserted into an object to be examined, there was danger in which the proximal end operating portion of the insertion tube of the endoscope was bent and deformed in the horizontal direction. In this way, there were cases in which inconvenience was brought about at the time of insertion.

When a clean cover portion is carried, if the form is such that the cover portion of the endoscope insertion tube is coiled and wrapped and put in a wrapping member, a channel such as a forceps channel provided in the endoscope cover becomes a bent shape. Therefore, the cover portion of the endoscope insertion tube containing the aforesaid channel becomes a bent shape. In addition, the insertion tube becomes a bent shape even in a state in which the insertion tube of an endoscope to be covered is covered with the cover portion of the endoscope insertion tube, so that the insertability of the tube into the body cavity will be quite worse. If the cover portion becomes a bent shape, there is inconvenience in which the cover portion is hard to cover the insertion tube of the endoscope to be covered.

SUMMARY OF THE INVENTION

An object of the present invention is to provide an endoscope apparatus of an endoscope cover type which can improve the insertability of an insertion tube when the tube is inserted into an object position to be examined in the body cavity or the like.

Another object of tile present invention is to provide an endoscope apparatus of an endoscope cover type which can prevent the proximal end portion of an insertion tube from bending and deforming in the horizontal direction and to improve the insertability of the tube when the tube is inserted into an object position to be examined.

Further, another object of the present invention is to provide an endoscope apparatus of an endoscope cover type in which an insertion tube of an endoscope cover is to bend, and the insertabilty of the insertion tube can be prevented from being worse and the fitting performance of an endoscope can be improved even in the case where the endoscope cover fitted to an endoscope to be covered is bent and wrapped while the cover is carried.

The present invention is an endoscope apparatus of an endoscope cover type comprising an endoscope having a long and narrow insertion tube and at least an endoscope cover for covering the insertion tube of the endoscope characterized in that the flexibility varies in a direction of the longitudinal axis of at least one insertion tube of the endoscope and the endoscope cover.

These objects and advantage of the present invention will be further apparent from the following explanation.

BRIEF DESCRIPTION OF THE DRAWINGS

FIG. 1 is an explanatory diagram showing the whole construction of an endoscope apparatus of an endoscope cover type;

FIG. 2 is a sectional view showing construction of an insertion tube of an endoscope cover type;

FIG. 3 is a construction explanatory diagram, partly broken away to show a flexible tube portion of an endoscope to be covered which is inserted into an endoscope cover;

FIG. 4 is a sectional view showing the construction of an exterior portion of the flexible tube portion of the endoscope in FIG. 3;

FIG. 5 is a sectional view showing construction of connected portion between cover exterior of an insertion tube of an endoscope cover and the tip of the cover or a connector for fixing of an endoscope operation part;

FIG. 6 is a sectional view showing a modification of the connected portion on between the cover exterior of the insertion tube and the tip of the cover or the connector for fixing the endoscope operation part shown in FIG. 5;

FIGS. 13 to 18 relate to the third embodiment of the present invention;

FIG. 13 is an explanatory diagram showing the whole construction of an endoscope apparatus of an endoscope cover type;

FIG. 14 is an explanatory diagram showing the whole construction of an endoscope to be covered which is inserted into an endoscope cover;

FIG. 15 is a sectional view showing construction of an insertion tube of an endoscope apparatus of an endoscope cover type;

FIG. 16 is a perspective view showing construction of the tip of an insertion tube cover portion;

FIG. 17 is a perspective view showing construction of a preventing member for preventing an insertion tube from breaking;

FIG. 18 is an explanatory diagram showing construction of a proximal end portion of an insertion tube cover portion in a state in which an endoscope to be covered is inserted into the cover portion;

FIG. 27 is a sectional view showing construction of an insertion tube of an endoscope apparatus of an endoscope cover type;

FIG. 28 is an explanatory diagram showing construction of a proximal end portion of an insertion tube cover portion in a state in which an endoscope to be covered is inserted into the cover portion;

FIGS. 30 to 55 relate to the fifth embodiment of the present invention;

FIG. 30 is an explanatory diagram showing the whole construction of an endoscope apparatus of an endoscope cover type;

FIG. 31 is an explanatory diagram showing the whole construction of an endoscope to be covered which is inserted into an endoscope cover;

FIG. 32 is a sectional view showing construction of an insertion tube of an endoscope apparatus of an endoscope cover type;

FIG. 33 is a perspective view showing construction of the tip of a cover of an insertion tube cover portion;

FIG. 34 is an explanatory diagram showing construction of connection between a fluid controlling device and a fluid channel of an endoscope cover;

FIG. 35 is an explanatory diagram showing construction example of an endoscope cover in which a fluid channel and a channel in an insertion tube cover portion are joined as one tube;

FIG. 36 is a sectional view showing connected portion between a fluid channel and a supplying air controlling valve provided in a fluid controlling device;

FIG. 37 is a perspective view showing an outward appearance of a supplying air controlling valve;

FIG. 38 is a sectional view showing the operation state of the supplying air controlling valve shown in FIG. 36;

FIG. 39 is a sectional view showing construction of connected portion when a silicon tube is connected to a fluid channel in a supplying air controlling valve;

FIG. 40 is an explanatory diagram showing construction of a fluid channel extended from an insertion tube cover portion and an insertion tube cover portion;

FIG. 41 is a perspective view showing a stranded state of the fluid channel shown in FIG. 40 and a sucking channel;

FIG. 42 is an explanatory diagram showing a state in which the endoscope to be covered shown in FIG. 40 fitted with an insertion tube cover is covered with an operation part cover portion and an universal cord cover portion;

FIG. 43 is a perspective view showing a first modification of means for stranding a fluid channel and sucking channel;

FIG. 44 is a perspective view showing a second modification of means for stranding a fluid channel and sucking channel;

FIG. 45 is a sectional view showing construction of the tip of an insertion tube cover portion in a state in which an insertion tube of an endoscope to be covered is inserted into the cover portion;

FIG. 46 is an explanatory diagram showing construction of joined portion between an insertion tube of an endoscope to be covered and operation part;

FIG. 47 is an explanatory diagram showing construction of a connector for fixing an endoscope operation part at the proximal end portion of an insertion tube cover portion;

FIG. 48 is a perspective view showing a state when an endoscope to be covered is fitted with an insertion tube cover portion;

FIG. 49 is a sectional view showing a state in which an insertion tube cover portion is fixed to an endoscope to be covered;

FIG. 50 is a perspective view showing an outward appearance of a state in which an insertion tube cover potion is fixed to an endoscope to be covered;

FIG. 51 is a sectional view showing construction of a modification of an insertion tube cover portion in which the distal end and proximal end of an endoscope insertion channel have the same axis;

FIG. 52 is a perspective view showing construction of a cover fixing portion of an endoscope insertion tube proximal end portion in the modification shown in FIG. 51;

FIG. 54 is an explanatory diagram showing construction of a wrapping material which wraps an insertion tube cover portion;

FIG. 55 is an explanatory diagram showing a state in which an insertion tube of an endoscope apparatus of an endoscope cover type fitted with an insertion tube cover portion is hung down in the vertical direction;

DETAILED DESCRIPTION OF THE PREFERRED EMBODIMENTS

FIGS. 1 to 6 show a first embodiment of the present invention.

Figure 1:
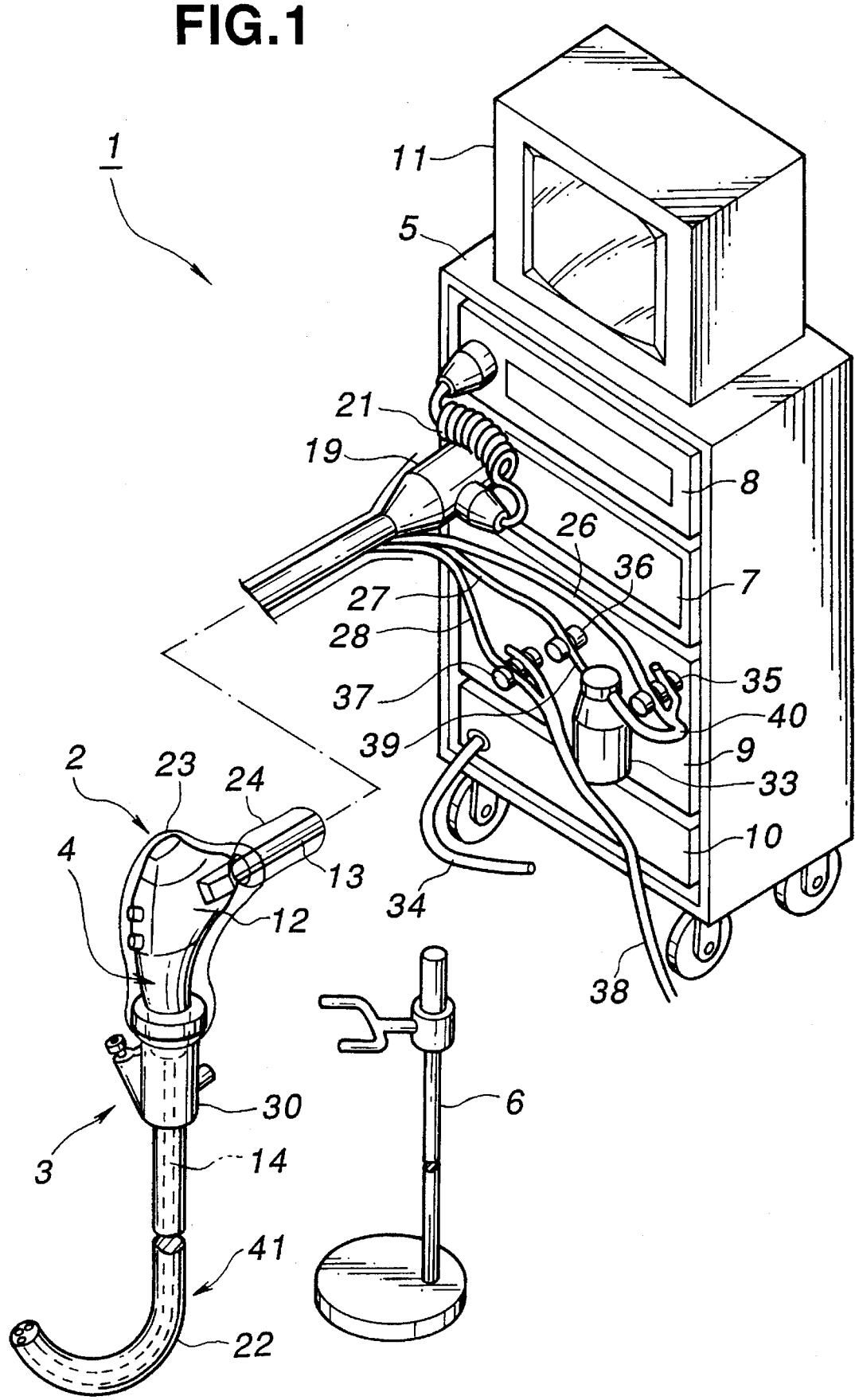
FIGS. 1 to 6 relate to the first embodiment of the present invention.

As shown in FIG. 1, an endoscope apparatus of an endoscope cover type 1 has an endoscope of an endoscope cover type (hereinafter, endoscope of a cover type) 2.

In the endoscope of a cover type 2, an endoscope cover (hereinafter, cover) 3 and an endoscope of an endoscope to be covered (hereinafter, endoscope to be covered) 4 which is fitted to the cover 3 are combined. When an endoscope examination is performed, the clean cover 3 covers the insertion tube of the endoscope to be covered 4. After the examination, the cover 3 is thrown away, and at the same time, the endoscope to be covered 4 is covered with a new clean cover 3 and repeatedly used. Therefore, the endoscope does not require washing and disinfecting after the examination.

The aforesaid endoscope apparatus 1 comprises the endoscope of a cover type 2, a cart 5 in which various kinds of surrounding devices to which the endoscope of a cover type 2 is connected and cover holder 6 which holds the endoscope of a cover type 2.

The aforesaid cart 5 houses, for example, a light source device 7, a video processor 8, a fluid controlling device 9 and an endoscope cover expander (hereinafter, expander) 10. A monitor 11 which displays an endoscope image by receiving a video signal from the video processor 8 is mounted on the top surface of the cart 5.

The endoscope to be covered 4 is provided with an operation part 12 having a wide diameter holding part at the proximal end of a long and narrow endoscope insertion tube 14. A universal cord 13 is extended from the operation part 12. A connector 19 is provided at the end of the universal cord 13.

The light source device 7 is detachably connected to the endoscope to be covered 4 through the connector 19 to supply illuminating light to an endoscope. The video processor 8 is detachably connected to the endoscope to be covered 4 through a signal cable 21 extended from the side of the connector 19. The video processor 8 drives an imaging apparatus contained in the endoscope to be covered 4 and processes a signal output from the imaging apparatus so as to convert the signal into a standard video signal and supply the video signal to the monitor 11.

An expanding tube 34 is connected to the expander 10. The expander 10 is to expand the cover 3 by supplying air into the cover 3 through the expanding tube 34. By this expansion, the cover 3 can be easily fitted to or pulled out from the endoscope to be covered 4. When the cover 3 is fitted to or pulled out from the endoscope to be covered 4, the cover holder 6 is used. For example, the proximal end of the cover 3 is held by the cover holder 6, and then, the endoscope to be covered 4 is inserted to or pulled out from the cover 3.

The cover 3 comprises a soft insertion tube cover portion 22 and an operation part cover portion 23 and universal cord cover portion 24 which consist of a thin and soft high polymer material, such as vinyl chloride. These cover portions cover an endoscope insertion tube 14 of the endoscope to be covered 4, the operation part 12 and the universal cord 13, respectively.

Since the fluid controlling device 9 is provided with a supplying air controlling valve 35, a supplying water controlling valve 36 and a sucking controlling valve 37, the supply of air and water and sucking are controlled by these electromagnetic valves. The supplying air controlling valve 35, supplying water controlling valve 36 and sucking controlling valve 37 are connected with a supplying air channel 26, supplying water channel 27 and sucking channel 28 extended from an insertion tube cover portion 22, respectively.

A sucking tube 38 is connected to the sucking controlling valve 37. An aspiration (not illustrated) is connected to the end of the sucking tube 38 to suck unnecessary body fluid or the like from the tip of the endoscope. A supplying water tube 39 is connected to the supplying water controlling valve 36. A supplying water tank 33 is connected to the tip of the supplying water tube 39. Further, two supplying air tubes 40 are extended from the fluid controlling device 9 and connected to the supplying air controlling valve 35 and the supplying water tank 33.

Figure 2:
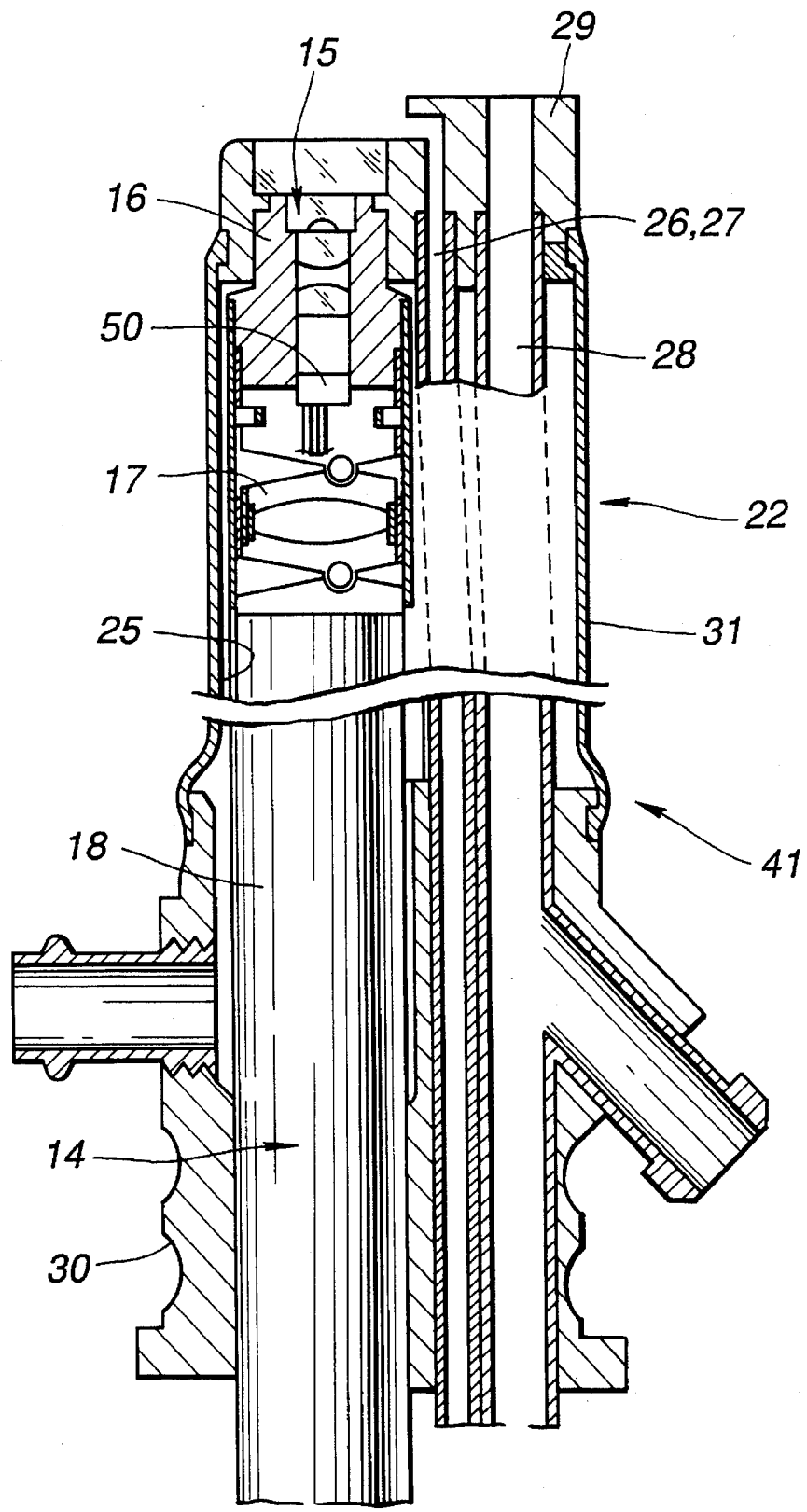

FIG. 2 shows a sectional view of an insertion tube 41 of an endoscope apparatus of an endoscope cover type in which the insertion tube cover portion 22 covers the endoscope to be covered 4.

An insertion tube 41 of an endoscope apparatus of an endoscope cover type contains mainly the insertion tube cover portion 22 and the insertion tube of an endoscope to be covered 14.

The insertion tube cover portion 22 is provided with the supplying air channel 26, supplying water channel 27, sucking channel 28 and an endoscope insertion channel 25 inserted into the endoscope insertion tube 14. These channels are preferably made of PTFE tube (polytetrafluoroethylene tube) and the tips of these channels are connected with a cover tip portion 29 which is made of hard resin or the like. The supplying air channel 26 and supplying water channel 27 are joined as one channel at the tips.

The proximal end of the insertion cover portion 22 is provided with a connector for fixing the endoscope operation part 30 made of hard resin or the like to connect and fix the insertion cover portion 22 and endoscope to be covered 4. Then, the cover tip portion 29 and a connector for fixing the endoscope operation part 30 are tightly connected with an insertion tube cover exterior 31 made of thin and soft high polymer which separates the insertion tube 14 of the endoscope to be covered 4 from surroundings. The sucking channel 28 also serves as a forceps channel into which forceps are inserted. A forceps insertion entrance is provided at the connector 30.

The endoscope insertion channel 25 is formed of the interior space, except for the portion of the supplying air channel 26, supplying water channel 27 and sucking channel 28, surrounded by a cover tip portion 29, an insertion tube cover exterior 31 and the connector for fixing the endoscope operation part 30. The endoscope insertion channel 25 indicates the part into which the endoscope to be covered 4 is inserted. The endoscope insertion channel 25 opens to the outside only in the connector for fixing the endoscope operation part 30 at the proximal end portion of the endoscope insertion channel 25, so that the other portions of the channel 25 are not exposed to the outside, Accordingly, when the endoscope insertion tube 14 is inserted into the channel 25, the insertion tube 14 is covered with a channel forming member (such as insertion tube cover exterior 31) which forms the endoscope insertion channel 25 excepts for the proximal end portion of the tube 14, so as not to be exposed to the outside. Further, the operation part 12 on the proximal end portion of the endoscope insertion tube 14 is covered with the operation part cover portion 23 and universal cord cover portion 24.

Therefore, when this apparatus is used for the endoscope examination, a state in which the insertion tube 14 of the endoscope to be covered 4 is not soiled is maintained. At the same time, the cover 3 is soiled, so that the cover is thrown away after use.

The endoscope insertion tube to be covered 14 consists of a hard tip portion 16 having an observation optical system 15 and illumination optical system (not illustrated), a bendable bending portion 17 and a flexible tube portion 18 having flexibility. Because of the flexibility of the flexible tube portion 18, an insertion tube 41 of an endoscope apparatus can be inserted into the body cavity and directed to the observing direction of the object by bending the bending portion 17.

A light guide (not illustrated) is inserted into the endoscope insertion tube 14. The distal end of the light guide is connected to the light source device 7 so that illuminating light from a lamp in the light source device 7 is transmitted and irradiated from the illumination optical system at the tip portion. In the endoscope insertion tube to be covered 14, an imaging device 50 is arranged in the image forming position of the observation optical system 15 and connected to the video processor 8 through a signal cable. An optical image of the subject of a patient which is illuminated by illuminating light is created on the imaging device 50 through the observation optical system 15. Thus, an observation window and illumination window are arranged against the observation optical system 15 of the endoscope insertion tube to be covered 14 and the illumination optical system (not illustrated) so that light is transmitted.

The imaging signal of the optical image which is photoelectrically converted by the imaging device 50 is fed to the video processor 8, and processed and converted into a standard video signal in the video processor. Then, the video signal is fed to the monitor 11, so that a subject image is displayed on the displaying picture plane.

Figure 3:
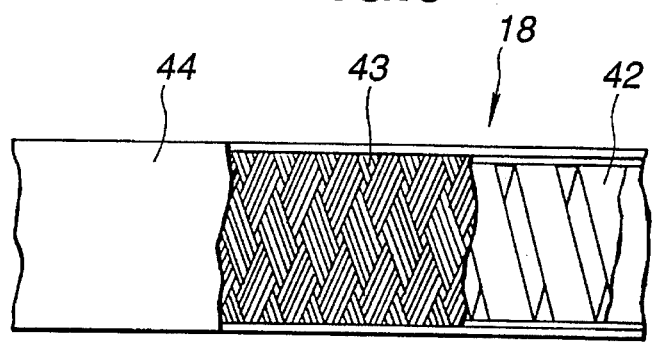

The flexible tube portion 18 of the endoscope insertion tube to be covered 14 is provided with a blade 43 which is combined by a plurality of strands on the outer periphery of a flex 42 as shown in FIG. 3 covered with an exterior cover 44 and formed of, for example, thermoplastic elastomer, which is more flexible. The exterior cover 44 is formed by making the mixed percentage of a plurality of kinds of thermoplastic elastomer having different hardness vary in the axis direction.

Figure 4:
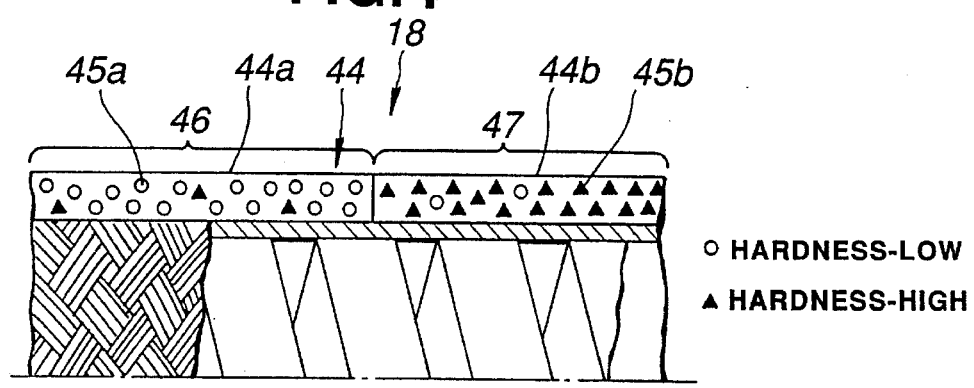

FIG. 4 is the sectional view of the exterior cover 44. FIG. 4 shows the mixed percentage of a plurality of kinds of thermoplastic elastomer having different hardness. In FIG. 4, a circle represents thermoplastic elastomer having low hardness 45a and a black triangle represents thermoplastic elastomer having high hardness 45b.

As shown in FIG. 4, the distal end portion 44a of the exterior cover 44 increases the percentage of low hardness elastomer 45a and the proximal end portion 44b of the exterior cover 44 increases the percentage of high hardness elastomer 45b, so that a soft portion 46 is formed at the distal end portion of the exterior cover 44a and a hard portion 47 at the proximal end portion 44b which is harder than the distal end portion is formed.

In addition, the hardness of the exterior cover 44 is adjusted to obtain favorable flexibility by combining the insertion tube cover portion 22 and insertion tube of an endoscope to be covered 14, so that the flexibility of the insertion tube of an endoscope to be covered 14 can be adjusted.

In FIG. 4, the flexibility of the exterior cover 44 of the insertion tube of endoscope to be covered 14 is changed by two stages in the direction of the longitudinal axis of the tube. However, it can be changed by two or more stages it can and also be changed continuously without levels.

Figure 5:
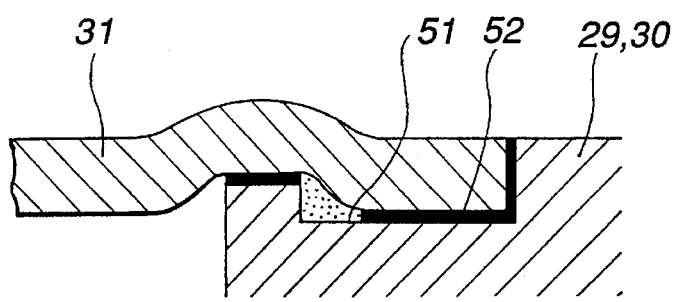

FIG. 5 shows an enlarged section of the connected portion between an insertion tube cover exterior 31 of the insertion tube cover portion 22 and a cover tip portion 29 or the connector for fixing endoscope operation part 30.

On the side surface of the connected side end portion between a cover tip portion 29 and the insertion tube cover exterior 31 of the connector for fixing the endoscope operation part 30, a recess part 51 is rotatably provided. The end of the insertion tube cover exterior 31 is dropped in the recess part 51 and fixed with glue 52 in the recess part 51.

Both ends of the insertion tube cover exterior 31 of the insertion tube cover portion 22 are fixed to the cover tip portion 29 and the connector for fixing the endoscope operation part 30. Since a general endoscope of a cover type has not been provided with recess and convex parts in which the end of the insertion cover exterior is caught at the tip of the cover and the connector for fixing the endoscope operation part, the cover tip portion and the connector for fixing the endoscope operation part could not be firmly fixed to the insertion tube cover exterior. Therefore, there is danger that the endoscope cover comes off when the insertion tube of an endoscope of an endoscope cover type is inserted into the object to be examined and the insertion tube is bent.

At the same time, the construction is formed as shown in FIG. 5 makes it possible that the connectability between the insertion tube cover exterior 31 and the cover tip portion 29 or the connector for fixing the endoscope operation part 30 is raised. The construction can make it prevent that the cover tip potion 29 or the cover tip portion 29 and insertion tube cover exterior 31 are dropped during insertion into the object to be examined, an affected part is soiled or cut, so that a safe examination can be carried out.

Figure 6:
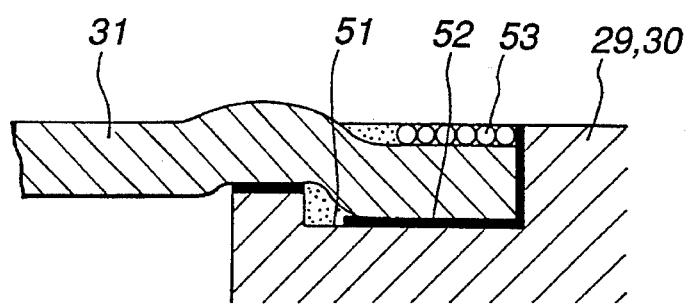

FIG. 6 shows a modification of the connected portion between the insertion tube cover exterior 31 and the cover tip portion 29 and the connector for fixing the endoscope operation part 30.

As shown in this modification, the end of the insertion tube cover exterior 31 can be dropped in the recess part 51 and fixed with the glue 52 in the recess part 51, and further, a thread 53, such as nylon can be bound around the insertion tube cover exterior 31 which is dropped in the recess part 51. Further, the glue 52 can fix thread 53 by applying the glue 52 on the thread 53.

In this way, much stronger fixation can be obtained by binding the thread 53 such as nylon and fixing the thread 53 with the glue 52. In addition, it is effective that the end surface of the insertion tube cover exterior 31 does not come off. The outer diameter 8 of the connected portion does not become wide and the insertion tube of the endoscope apparatus of an endoscope cover type can be thin, so that insertability into the body cavity of a patient can be improved.

In the endoscope apparatus of an endoscope cover type 1 of this embodiment, the clean cover 3 is fitted to the endoscope to be covered 4 and inserted into the object to be examined, such as the body cavity as the endoscope of a cover type 2 in a state in which the endoscope to be covered 4 is separated from surroundings. When the endoscope is used, a clean state can be maintained because the endoscope to be covered 4 is covered with the cover 3. The sucking channel 28 which serves as the supplying air channel 26, supplying water channel 27 and forceps channel is fitted to the cover 3 and thrown away with the cover 3 after used. Therefore, the contaminated channel will not be used again.

Since the endoscope of a cover type 2 is formed in this way, it is not necessary to wash and disinfect the endoscope to be covered 4, which is an endoscope main body, in every examination and the endoscope can be kept clean all the time. Thus, the endoscope examination can be easily carried out. The endoscope to be covered 4 can be continuously used without being washed and disinfected again. For example, when all examinations of one day are completed, the endoscope can be washed and disinfected. Accordingly, using efficiency of the endoscope can be made to be raised.

Also, the endoscope insertion tube to be covered 14 is formed in such that the flexibility changes in the direction of the longitudinal axis, so that the flexibility of the insertion tube 41 of the endoscope apparatus of an endoscope cover type is changed in the direction of the longitudinal axis. Because the proximal end portion of the endoscope has relatively high hardness and the distal end portion has relatively low hardness, the insertability of the endoscope can be improved without bending the proximal end of the insertion tube or catching the distal end in the body cavity.

Thus, when the flexibility of the insertion tube is changed in the direction of the longitudinal axis, it is useful to change the mixed percentage of a plurality of thermoplastic elastomer having different hardness in the direction of the longitudinal axis as mentioned above, in order to obtain stable quality. However, if the insertion tube cover portion 22 has such a structure, the insertion tube cover portion 22 to be thrown away becomes expensive and complicated in its structure. In this embodiment, because the structure in which the flexibility of the insertion tube is different is provided in the endoscope to be covered 4 which is repeatedly used, the endoscope can be inexpensively formed as an endoscope of an endoscope cover type. Therefore, it can reduce the burden of a user. In addition, because the structure of the cover is simple, the durability of the cover can be improved and the infection due to the damage of the cover when it is fitted to or used can be prevented.

In the aforesaid endoscope to be covered 4, the insertion tube 14 is covered with the insertion tube cover portion 22 and inserted into an object to be examined. In a general endoscope apparatus of an endoscope cover type, the relation between the insertion tube length of the endoscope to be covered and the insertion tube length of the insertion tube cover portion has not been considered. Thus, when the insertion tube length of the insertion tube cover portion is longer than the insertion tube length of the endoscope to be covered, the insertion tube cover portion is slack during insertion. Therefore, there was danger that it had a bad influence on the insertability or on observation or illumination because the tip of the endoscope to be covered comes off from the fitted portion of the tip of the cover.

Figure 7:
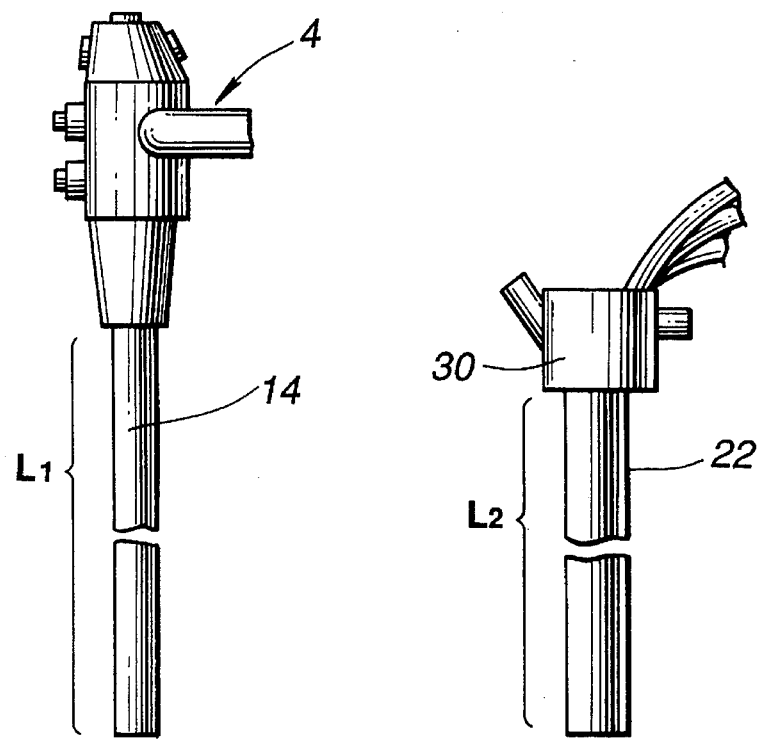
FIG. 7 is an explanatory diagram showing relation of an insertion tube length of a state before fitting an insertion tube cover into an endoscope of an endoscope to be covered.
Figure 8:
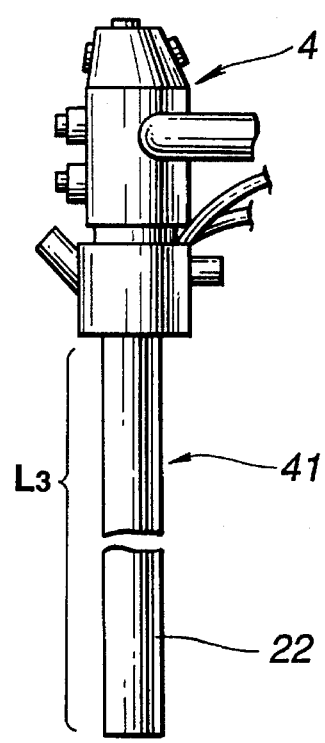
FIG. 8 is an explanatory diagram showing relation of an insertion tube length of a state fitting an insertion tube cover into an endoscope to be covered.

FIGS. 7 and 8 show that examples of the structure to which an insertion tube cover portion can be tightly fitted into the insertion tube of the endoscope to be covered at all the time by forming at least a part of the insertion tube cover portion using an elastic member.

FIG. 7 shows a state before the insertion tube cover portion 22 is fitted to the endoscope to be covered 4. FIG. 8 shows relation of each insertion tube length in a state in which the insertion tube cover portion 22 is fitted to the tube.

In the insertion tube cover portion 22, at least a part of the insertion tube cover exterior 31 is formed of an elastic member and expands and contracts in the direction of the longitudinal axis. Provided that the length of the insertion tube 14 of the endoscope to be covered is L1, the length of the insertion tube of the insertion tube cover portion 22 is L2 and the length of the insertion tube (that is, the length of the insertion tube 41 of the endoscope apparatus of the endoscope cover type) of the insertion tube cover portion in a state in which the insertion tube cover portion 22 is fitted to the endoscope to be covered 4 is L3, each length is determined to make the relation of

L1=L3>L2.

That is, the insertion tube length of the insertion tube cover portion 22 is shorter than the insertion tube length of the endoscope to be covered 4 before fitting the tube cover portion 22. When the cover portion 22 is fitted to the endoscope to be covered 4, the length of the insertion tube cover exterior 31 extends by the length L1–L2 to fit the insertion tube of the endoscope to be covered 14.

Therefore, when the insertion tube of the endoscope apparatus of the endoscope cover type 41 is inserted into an object to be examined (not illustrated), the insertion tube 41 is bent, so that the insertion tube cover portion 22 is slack against the insertion tube 14 of the endoscope to be covered and then, the cover tip portion 29 is separated from the tip of the endoscope to be covered 16. Thus, it prevents the examination from narrowing an observation visual field or darkening illumination for observation. Therefore, the examination can be performed safely and certainly.

Here, although it is explained that the whole insertion tube cover exterior 31 uses an elastic member, the elastic member may be used for a part of it. Both of the insertion tube cover exterior of the insertion tube cover portion and internal channel tube may be made of an elastic member, or only the insertion cover exterior may be made of the elastic member, or the internal channel tube may be assembled as the length required when the tube is fitted to the endoscope.

Figure 10:
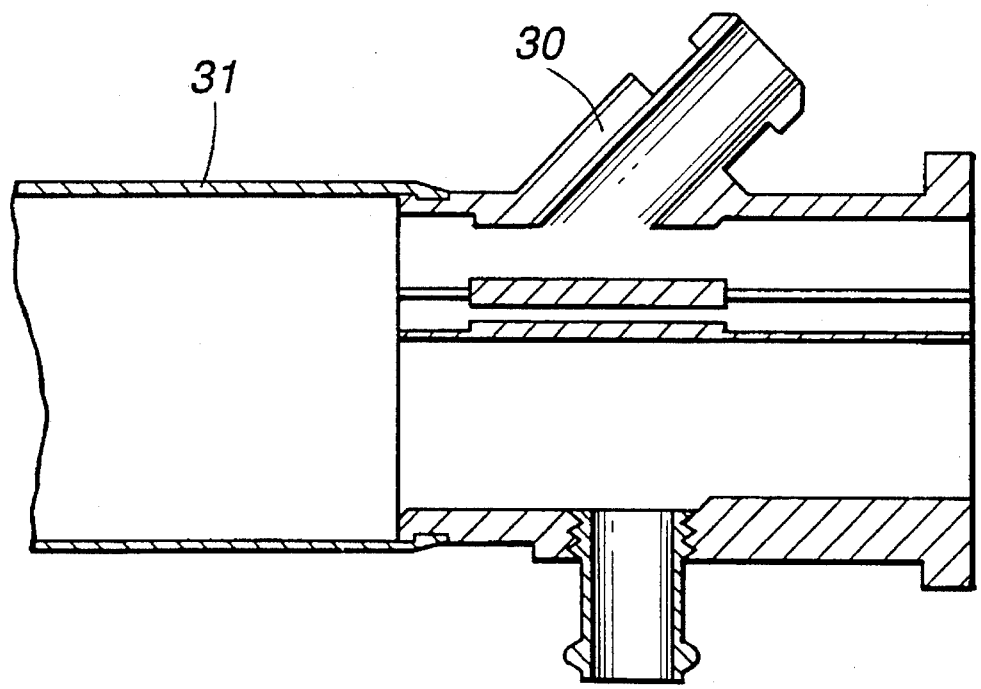
FIG. 10 is a sectional explanatory diagram explaining the second process in an assembling method of an insertion tube cover.
Figure 11:
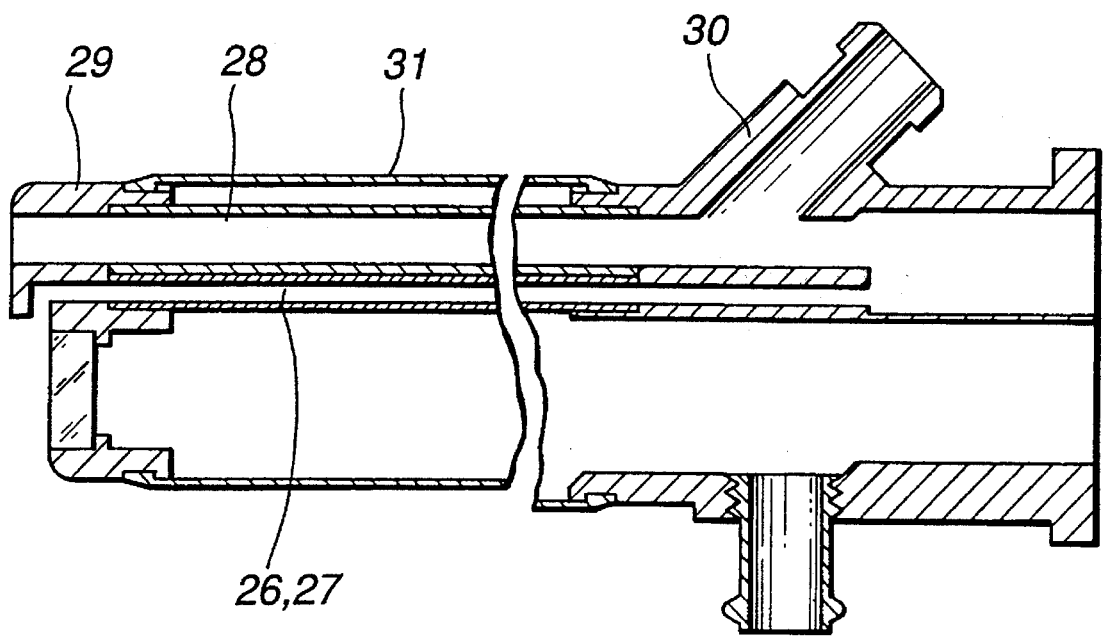
FIG. 11 is a sectional explanatory diagram explaining the third process in an assembling method of an insertion tube cover.

Next, an assembling method of the insertion tube cover portion 22 will be explained in reference to FIGS. 9 to 11.

Figure 9:
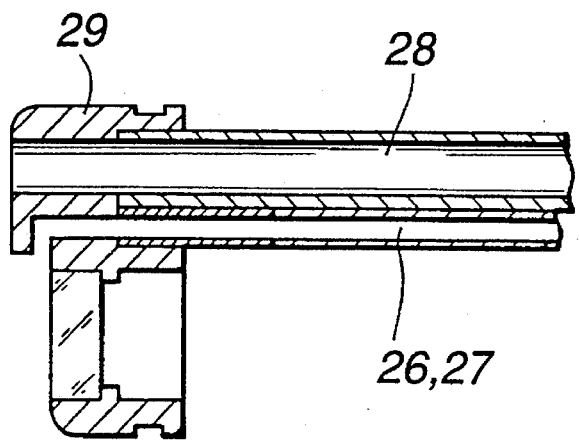
FIG. 9 is a sectional explanatory diagram explaining the first process in an assembling method of an insertion tube cover.

First of all, FIG. 9 shows the first process which connects the ends of the supplying air channel 26, supplying water channel 27 and sucking channel 28 to the cover tip portion 29. FIG. 10 shows the second process which connects and fixes the end of the insertion tube cover exterior 31 to the connector for fixing the endoscope operation part 30. FIG. 11 shows the third process which combines the cover tip portion and channel completed by the first process and the connector for fixing the endoscope operation part and insertion tube cover exterior completed by the second process, and connects and fixes them. These three processes form the assembling process of the insertion tube cover portion 22.

In this way, the process is divided into three stages, so that the first process and second process can be performed in parallel, or the first process and second process can make and store parts, individually. Therefore, this method can improve the operation efficiency of the apparatus in comparison with the former process which connects all of the supplying air channel 26, supplying water channel 27, sucking channel 28 and insertion tube cover exterior 31 and connects the connector for fixing the endoscope operation part 30 to the end of the aforesaid all channels. Further, the costs with regard to the production can be cut down due to the improvement of the operation efficiency. Then, an inexpensive endoscope apparatus of an endoscope cover type can be provided.

Figure 12:
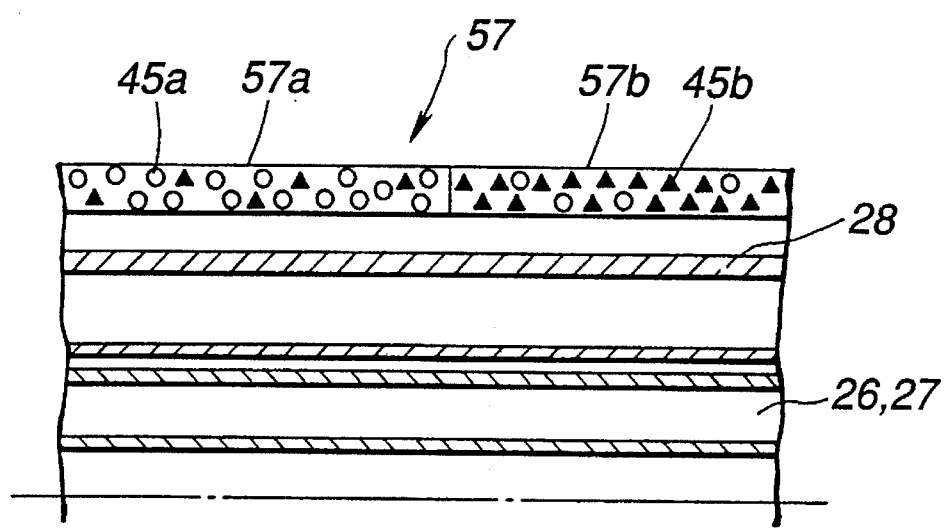
FIG. 12 is a sectional view showing construction of exterior of an insertion tube cover of an endoscope cover related to the second embodiment of the present invention.

FIG. 12 is a sectional view showing the construction of the insertion tube cover exterior of the endoscope cover related to the second embodiment of the present invention.

In the first embodiment, the flexibility of the insertion tube of the endoscope to be covered 14 is changed in the axis direction, so that the flexibility of the insertion tube 41 of the endoscope apparatus of an endoscope cover type is changed in the axis direction. In this embodiment, the flexibility of an insertion tube cover portion 22 which covers an endoscope insertion tube 14 is changed in the axis direction, so that the flexibility of an insertion tube of an endoscope apparatus of an endoscope cover type 41 is changed in the axis direction.

The material of the insertion tube cover portion 22 is, for example, thermoplastic elastomer. This embodiment uses the mixed percentage of a plurality of kinds of thermoplastic elastomer having different hardness that is changed in the axis direction.

FIG. 12 is a sectional view of an insertion tube cover exterior 57 of a plurality of kinds of thermoplastic elastomer having different hardness. In FIG. 12, a circle represents thermoplastic elastomer having low hardness 45a and a black triangle represents thermoplastic elastomer having high hardness 45b. As shown in FIG. 12, a distal end portion 57a of an insertion tube cover exterior 57 increases the percentage of low hardness elastomer 45a and the proximal end portion 57b of the exterior cover 57 increases the percentage of high hardness elastomer 45b so as to make the distal end portion 57a soft and to make the proximal end portion 57b harder than the distal end portion. Then, the insertion tube cover exterior 57 is formed so that the flexibility changes in the axis direction.

Further, the hardness of the insertion tube cover portion 22 is adjusted such that favorable flexibility can be obtained by combining the insertion tube cover portion 22 and insertion tube of the endoscope to be covered 14. Then, the flexibility of the insertion tube of the endoscope to be covered 14 can be adjusted.

Thus, the flexibility of the insertion tube cover portion 22 is changed in the axis direction, so that the flexibility of the insertion tube 41 of the endoscope apparatus of an endoscope cover type change in the same manner as that of the first embodiment. Accordingly, the insertability of the insertion tube when the tube is inserted into the body cavity can be improved and the inconvenience, such as a pain of a patient when the tube is inserted, can be extremely reduced.

In the first and second embodiments, either flexibility of the insertion tube of the endoscope to be covered and insertion tube cover portion is changed in the axis direction. However, as a modification which combines the first and second embodiments, each flexibility of the insertion tube of the endoscope to be covered and the insertion tube cover portion is changed in the axis direction, individually, so that the flexibility of the insertion tube of the endoscope apparatus of the endoscope cover type 41 may be changed in the axis direction. As a result, we can pliably deal with the examination in order that the favorable flexibility can be obtained.

FIGS. 13 to 18 show the third embodiment of the present invention.

Figure 13:
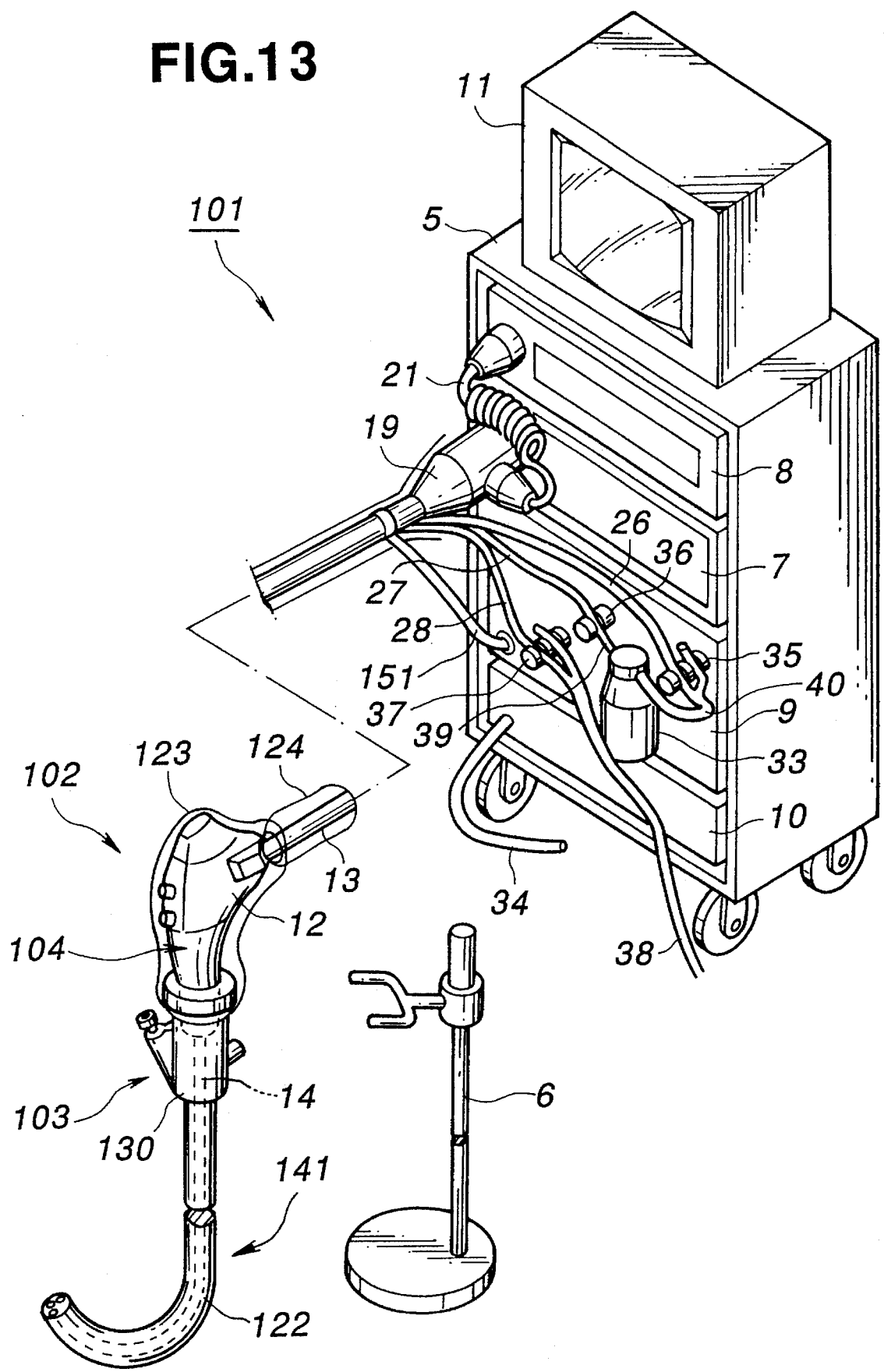

The whole construction of an endoscope apparatus of an endoscope cover type 101 of the third embodiment is shown in FIG. 13 and formed in the same manner as that of the first embodiment shown in FIG. 1. Only different constructional elements are explained. To the same constructional elements, the same reference numerals are given and the explanation thereof is omitted.

An endoscope of a cover type 102 provided in an endoscope apparatus of an endoscope cover type 101 is formed by combining an endoscope cover having channels (cover, hereinafter) 103 and an endoscope to be covered 104 which is fitted to the cover 103. When the endoscope examination is performed, the insertion tube of the endoscope to be covered 104 is covered with a clean cover 103. After the examination, the cover 103 is thrown away. At the same time, the endoscope to be covered 104 is covered with a new clean cover 103 and repeatedly used.

The cover 103 is formed of an insertion tube cover portion 122 made of thin and soft resin or the like, an operation part cover portion 123 and an universal cord cover portion 124 which are made of polymer materials, such as vinyl chloride. These cover portions cover an endoscope insertion tube 14, operation part 12 and universal cord 13 of the endoscope to be covered 104, respectively.

The endoscope of an cover type 102 is connected to a light source device 7 provided in a cart 5, video processor 8, fluid controlling device 9, endoscope cover expander 10 or the like, so that an endoscope image of a position to be examined which is obtained by the endoscope is displayed in a monitor 11.

Figure 14:
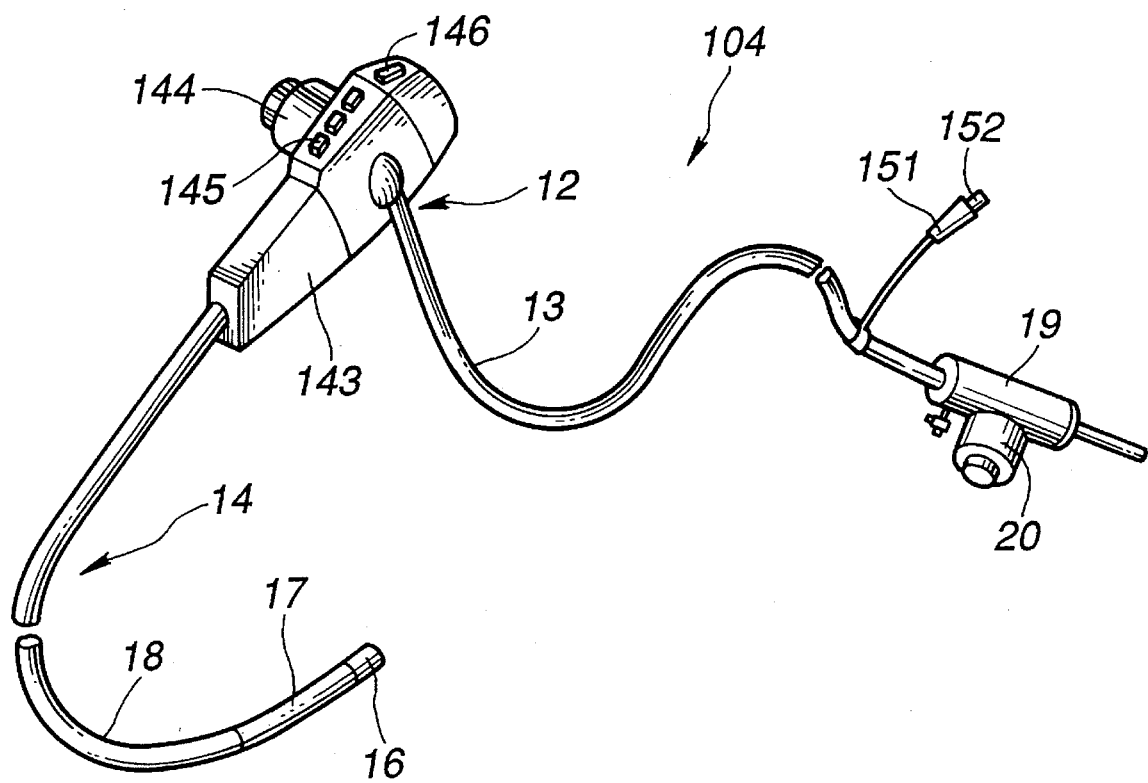

FIG. 14 shows the whole construction of the endoscope to be covered 104.

The endoscope to be covered 104 is provided with the operation part 12 which is held by an operation and performs various kinds of operations. The insertion tube 14 and the universal cord 13 are connected so that the tube 14 and the cord 13 are extended from the operation part 12. The holding part 143 is provided in the operation part 12. Above the holding part 143, an angle knob 144 for performing bending operation, supplying air and water sucking control switch 145 and a function switch 146 for performing freeze and release for photographing are provided.

The insertion tube 14 is formed of a hard tip 16 having an observation optical system and illumination optical system which are not illustrated, a bendable bending part 17 and a flexible tube having flexibility, from the tip. Due to the flexibility of the flexible tube 18, an insertion tube 141 of the endoscope apparatus covered with the cover 103 can be freely inserted into the body cavity and can direct the tip in the direction for observing an object by bending the bending part 17.

At the same time, the end of the universal cord 13 branches out into two parts. One of the two parts is provided with a connector 19. A side of the connector 19 is provided with an electric connector part 20 to which a signal cable 21 for connecting a video processor 8 is connected. The other side of the connector 19 is provided with a second connector 151. A second electric connector 152 is provided at the end of the second connector 151. As shown in FIG. 13, the second connector 151 is connected to a fluid controlling device 9, so that an operation indicating signal from the supplying air and water sucking control switch 145 provided in the operation part 12 is transmitted to the fluid controlling device 9 through the universal cord 13 and the second connector 151.

Figure 15:
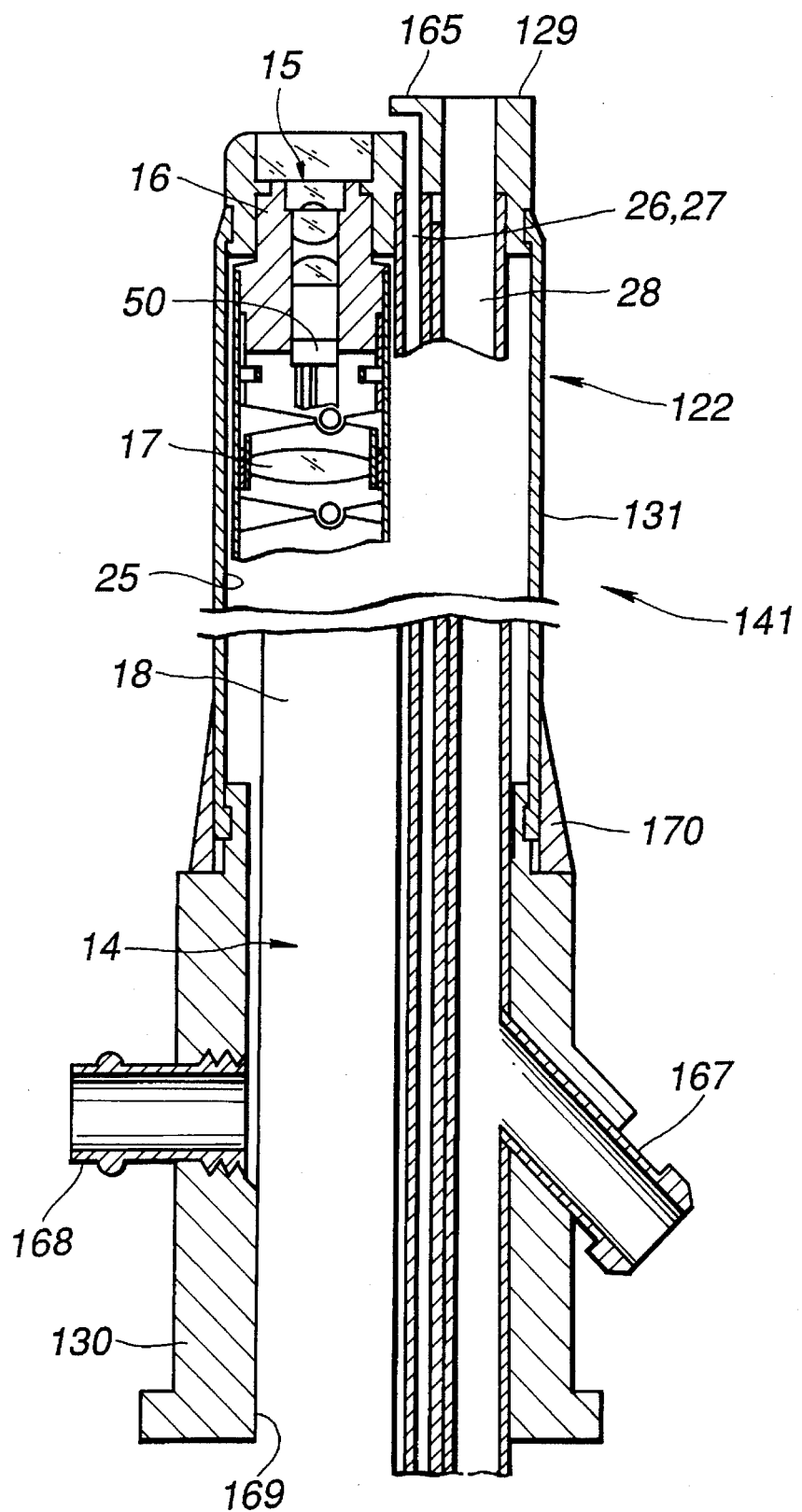

FIG. 15 shows a sectional view of the insertion tube 141 of the endoscope apparatus of an endoscope cover type in which the endoscope to be covered 104 is covered with an insertion tube cover portion 122.

The insertion tube 141 of the endoscope apparatus of an endoscope cover type mainly contains the insertion tube cover portion 122 and the insertion tube of the endoscope to be covered 14.

The insertion tube cover portion 122 is provided with a supplying air channel 26 made of PTFE tube or the like, a supplying water channel 27, a sucking channel 28 serving a forceps channel, and an endoscope insertion channel 25 into which the endoscope insertion tube 14 is inserted. The tips of these channels are connected with a cover tip portion 129 made of hard resin or the like. The supplying air channel 26 and supplying water channel 27 are joined at their tips to be one channel.

In the cover tip portion 129, as shown in FIG. 16, an observation window 161 and illumination window 162 which are made of transparent glass or resin so as to transmit light to the positions facing the observation optical system (see FIG. 15) and the illumination optical system (not illustrated) of the endoscope to be covered 104 are tightly provided. In addition, the cover tip portion 129 is provided with a supplying air and water nozzle 165 opening toward the observation window 161. The opening portion of the supplying air and water nozzle 165 is connected to the supplying air channel 26 and supplying water channel 27.

To the cover tip portion 129, as shown in FIG. 15, a thin and soft insertion tube cover exterior 131 for separating the insertion tube 14 of the endoscope to be covered 104 from surroundings is tightly connected.

The proximal end portion of the insertion tube cover exterior 131 is provided with a connector for fixing an endoscope operation part 130 having a forceps insertion entrance 167, and an extension tube connector 168 to which an extension tube 34, provided in an expander 10, is connected. The proximal end portion of the connector for insertion tube cover exterior 131 is tightly connected to the connector 130. The proximal end portion of the connector for fixing an endoscope operation part 130 is provided with an opening portion 169 of an endoscope insertion channel 25 into which the endoscope insertion tube 14 is inserted. Further, a channel, such as the sucking channel 28 is projected. One end of the sucking channel 28 opens to the cover tip portion 129.

The proximal end of the endoscope insertion channel 25 opens to the outside only in tile connector for fixing the endoscope operation part 130. The other parts are not exposed to the outside. Therefore, if the endoscope insertion tube 14 is inserted into the endoscope insertion tube cover portion 122, the endoscope insertion tube 14 is covered with the insertion tube cover exterior 131 or the like so that the tube is not exposed to the outside.

Figure 18:
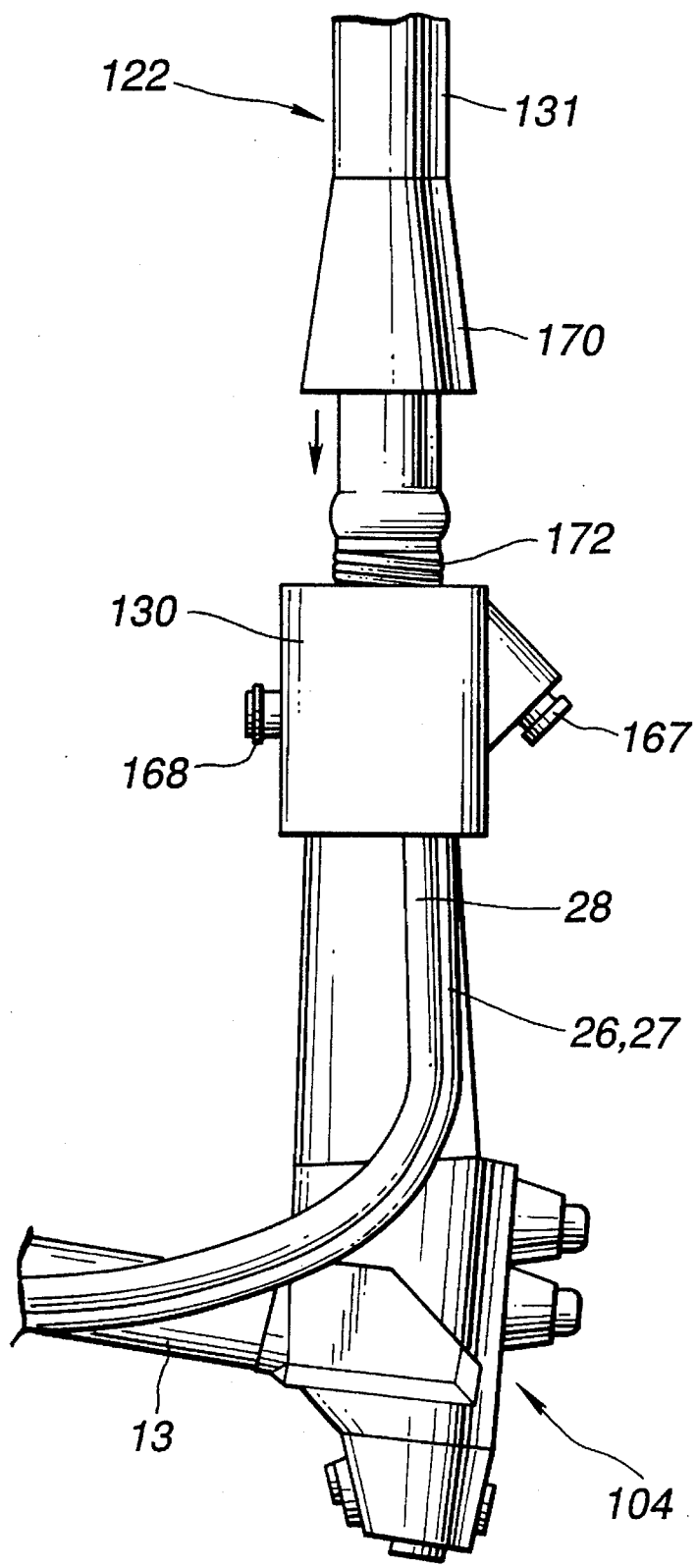

On the insertion tube cover portion 122, a cylindrical preventing member for preventing an insertion tube from breaking 170 made of an elastic member as shown in FIG. 17 is provided near the connector for fixing the endoscope operation part 130 of the proximal end portion of the insertion tube cover exterior 131. The outside shape of the preventing member 170 is formed like a taper. As shown in FIG. 17, the preventing member 170 is provided with a female screw part 171 in the inside surface. The female screw part 171 is spirally fitted to and fixed to a male screw part 172 shown in FIG. 18 provided in the connector for fixing the endoscope operation part 130.

The preventing member 170 can be detached from the connector for fixing the endoscope operation part 130 or the like, or may be fixed to the insertion tube cover portion 122. In the preventing member 170, the inside of the insertion tube cover exterior 131 may be expanded to prevent an insertion tube from breaking, instead of a shape being expanded to the outside, or both of the inside and outside may be expanded.

In the endoscope apparatus of an endoscope cover type 101 of this embodiment, the preventing member 170 is provided at the proximal end portion of the insertion tube cover portion 122. Therefore, the bending and transforming the insertion tube in the horizontal direction can be prevented even in the case in which the insertion tube cover portion is extremely bent or repeatedly bent when the insertion tube is inserted into an object to be examined. Also, the proximal end portion of the insertion tube can be prevented from bending, so that the insertability can be improved.

Generally, the construction of the insertion tube cover portion of the endoscope apparatus of an endoscope cover type containing three channels for supplying air, supplying water and sucking is used. If the insertion tube of the endoscope to be covered is covered with an insertion tube cover portion, means for considering detachability and safety should be provided in the insertion tube cover portion and the insertion tube of the endoscope to be covered. As a result, the insertion tube of the endoscope apparatus of an endoscope cover type becomes thick in comparison with the former endoscope without having a cover, so that the insertability into the body cavity becomes worse and the tube has given fear and pain to a patient.

Figure 19:
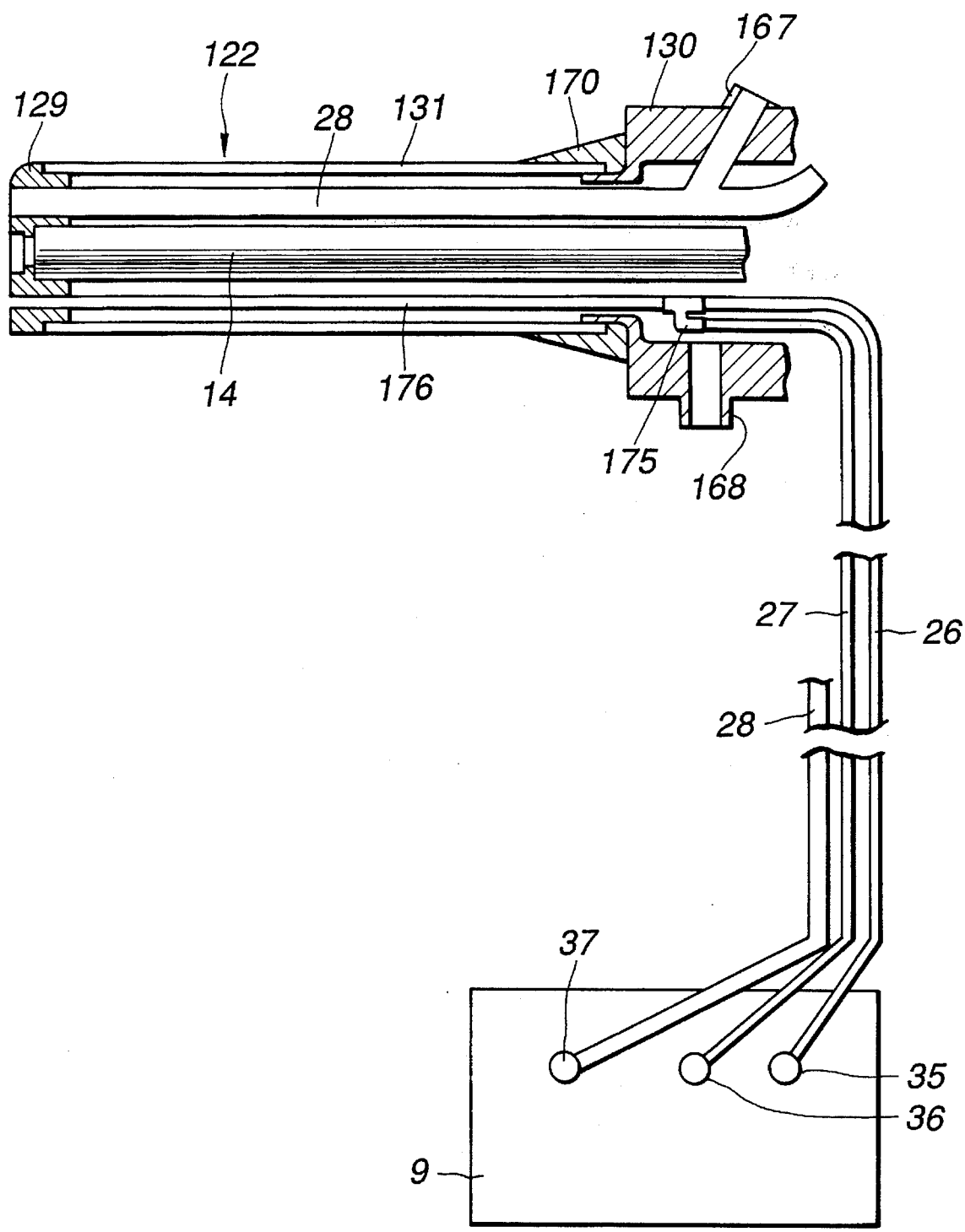
FIG. 19 is an explanatory diagram showing a construction example of an endoscope cover in which a supplying air channel and supplying water channel are joined as one tube in an insertion tube cover portion.

FIG. 19 shows a construction example of a fluid channel in an endoscope cover.

In FIG. 19, reference numerals 26 and 27 represent a supplying air channel and supplying water channel formed with a PTFE tube or the like which is connected to the fluid controlling device 9, respectively. The supplying air channel 26 and supplying water channel 27 are connected to a connecting tube 175 provided within the connector for fixing the endoscope operation part 130 so as to be one channel. The connecting tube 175 is made of hard resin and has about 1 mm of the wall thickness. A supplying air and water channel 176 made of PTFE tube or the like is connected to the other end of the connecting tube 175 and opens to the tip of the insertion tube cover portion 122.

In this way, only the supplying air and water channel 176 which has two functions of supplying air and water and the sucking channel 28 are provided within the insertion tube cover exterior 131. Thus, only one channel is required for supplying air and water and the diameter of the insertion tube cover portion 122 can be narrow.

Therefore, not only the insertability is improved but also space can be effectively used because the connecting tube 175 is contained in the connector for fixing the endoscope operation part 130 which has space. Further, when the endoscope channel 25 of the insertion tube cover portion 122 is inserted into the endoscope to be covered 104, the cover portion 122 is not caught by the connecting tube 175 or the like and can be inserted smoothly.

In this embodiment, one supplying air channel 26 and one supplying water channel 27 which are connected to the fluid controlling device 9 and the connecting tube 175 are provided, respectively. However, using a pipe-like material, the number of each supplying air channel and supplying water channel may be two or more.

In the general endoscope apparatus of an endoscope cover type, there is a case in which metal is used for the construction of the insertion tube of the endoscope to be covered. Because of this case, electromagnetic wave noise is generated from the endoscope to be covered, so that there is danger of causing a bad influence on other electric circuits, such as a circuit of a video processor. Nevertheless, the noise emitted from the insertion tube to the outside can be reduced by forming the insertion tube of the endoscope apparatus as shown in FIGS. 20 and 21.

Figure 20:
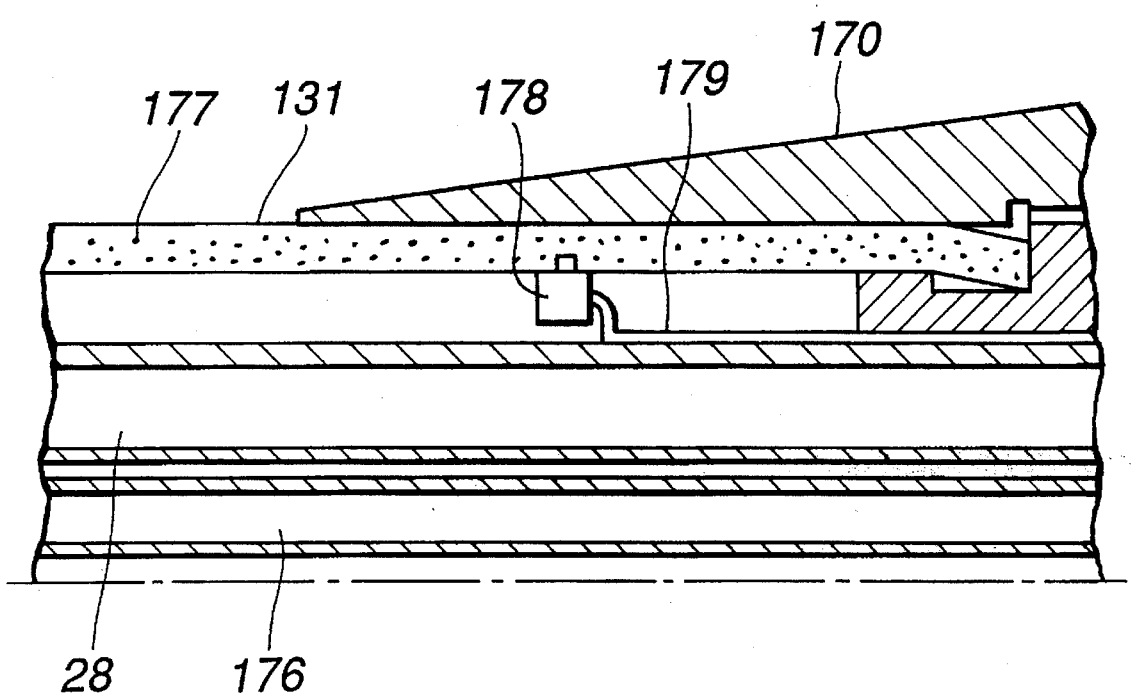
FIG. 20 is a sectional view of an area near an preventing member for preventing an insertion tube from breaking in an insertion tube cover portion of an endoscope apparatus of an endoscope cover type.

FIG. 20 is a sectional view of the portion near the preventing member 170 of the endoscope apparatus of an endoscope cover type.

In FIG. 20, reference numeral 131 represents an insertion tube cover exterior which is one of constructional elements of the insertion tube cover portion 122 and, for example, the cover exterior is made of thermoplastic elastomer. Metal powder 177 is mixed in the thermoplastic elastomer of the insertion tube cover exterior 131, so that the cover exterior 131 is conductive. A connecting pin 178 is connected to the insertion tube cover exterior 131 and connected to the fluid controlling device 9 through a lead wire 179 connected to the connecting pin 178.

Figure 21:
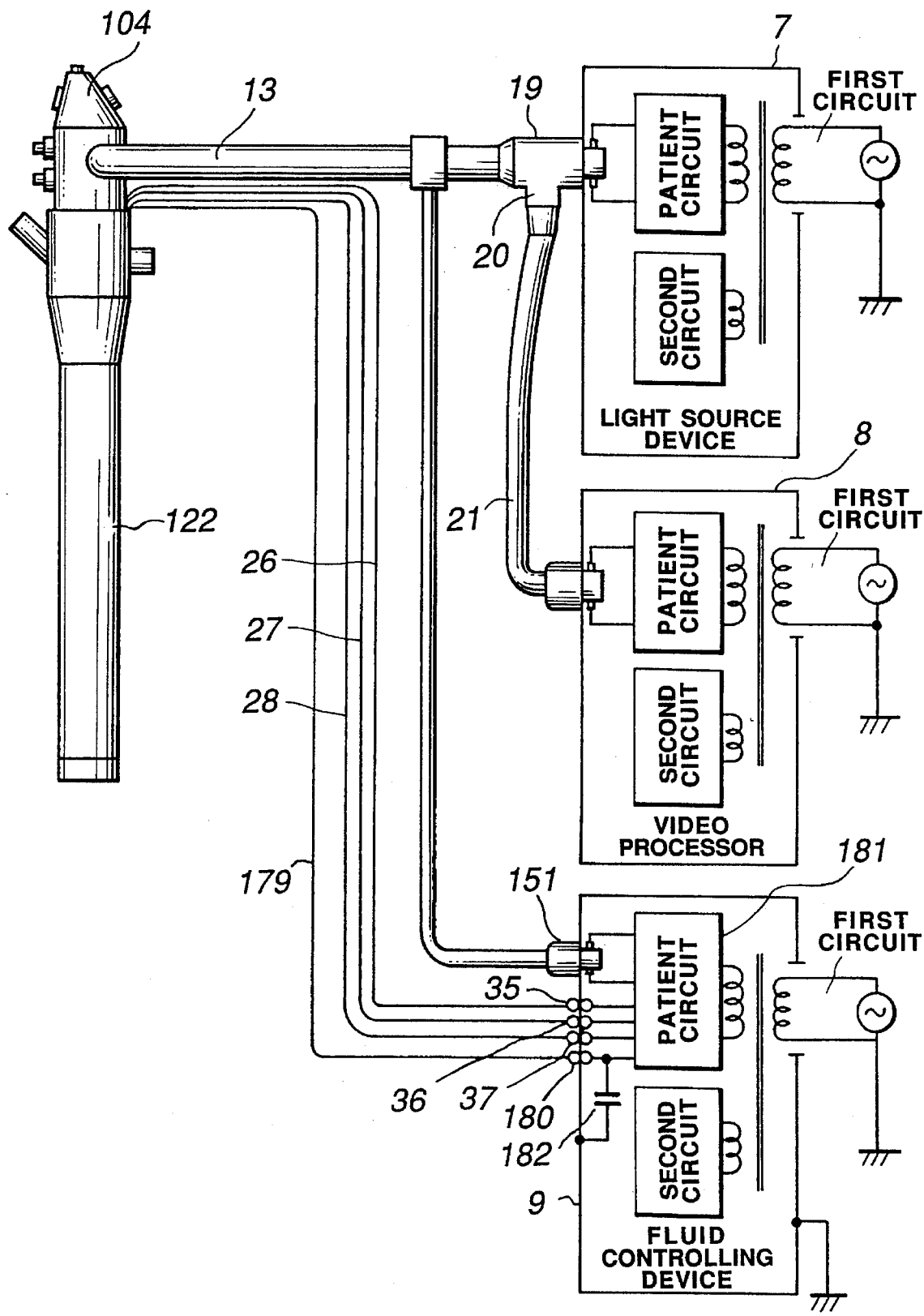
FIG. 21 is an explanatory diagram showing a connecting state among an endoscope to be covered and an insertion tube cover portion, and a light source device, video processor and fluid controlling device.

The lead wire 179 extends from the connector for fixing the endoscope operation part 130 to the outside as shown in FIG. 21 and stretches with the supplying air channel 26, supplying water channel 27 and sucking channel 28 to the fluid controlling device 9. Thus, the lead wire 179 is connected to a connecting terminal 180 provided in the fluid controlling device 9. The connecting terminal 180 is connected to the ground of a patient circuit 181 within the fluid controlling device 9 and connected to a box of the fluid controlling device 9 through a capacitor 182 which has relatively small capacity. Also, the box of the fluid controlling device 9 is grounded. That is, the insertion tube cover exterior 131 is connected to the ground of the patient circuit 181 within the fluid controlling device 9 and grounded through the capacitor 182.

The light source device 7, video processor 8 and fluid controlling device 9 are insulated from the patient circuit. A second circuit is insulated from a first circuit. Thus, the endoscope to be covered 104 connected to the patient circuit is not grounded in comparison with the first circuit which is grounded. Accordingly, in the endoscope to be covered 104 and light source device 7, and the endoscope to be covered 104 and video processor 8, only the patient circuit of each device is connected to the endoscope to be covered 104 and the endoscope to be covered 104 is not grounded through the light source device 7 and video processor 8.

In the construction formed in this way, the insertion tube cover exterior 131 is conductive. An electromagnetic interrupting effect is obtained due to the grounding, electromagnetic wave noise emitted from the endoscope to be covered 104 to the outside can be reduced and electromagnetic wave noise entering from the outside can be reduced.

Because the insertion tube cover exterior 131 is grounded through a capacitor, the exterior 131 has a grounding effect for the noise which is high-frequency wave, so that currents are not sent to a patient even when a ground line is cut.

Further, in this embodiment, the insertion tube cover exterior 131 is conductive using metal powder 177. However, the insertion tube cover exterior 131 may be conductive using metal wire made to be wire netting, metal soutache braid or the like.

At the same time, the universal cord cover portion of the endoscope cover used for the endoscope apparatus of an endoscope cover type covers the universal cord and connector of the endoscope to be covered to prevent the universal cord and connector from contaminating. Nevertheless, the construction of the connected portion between such universal cord cover and the light source device provided in the connector has not been considered. Therefore, an imperfect contact is caused due to the connection in which the connected portion is kept being covered, or it is inconvenient that a part corresponding to the connected portion should be cut off.

FIGS. 22 to 26 show examples of the construction of an endoscope cover which can surely connect the light source device and the endoscope to be covered and protect the endoscope to be covered.

Figure 22:
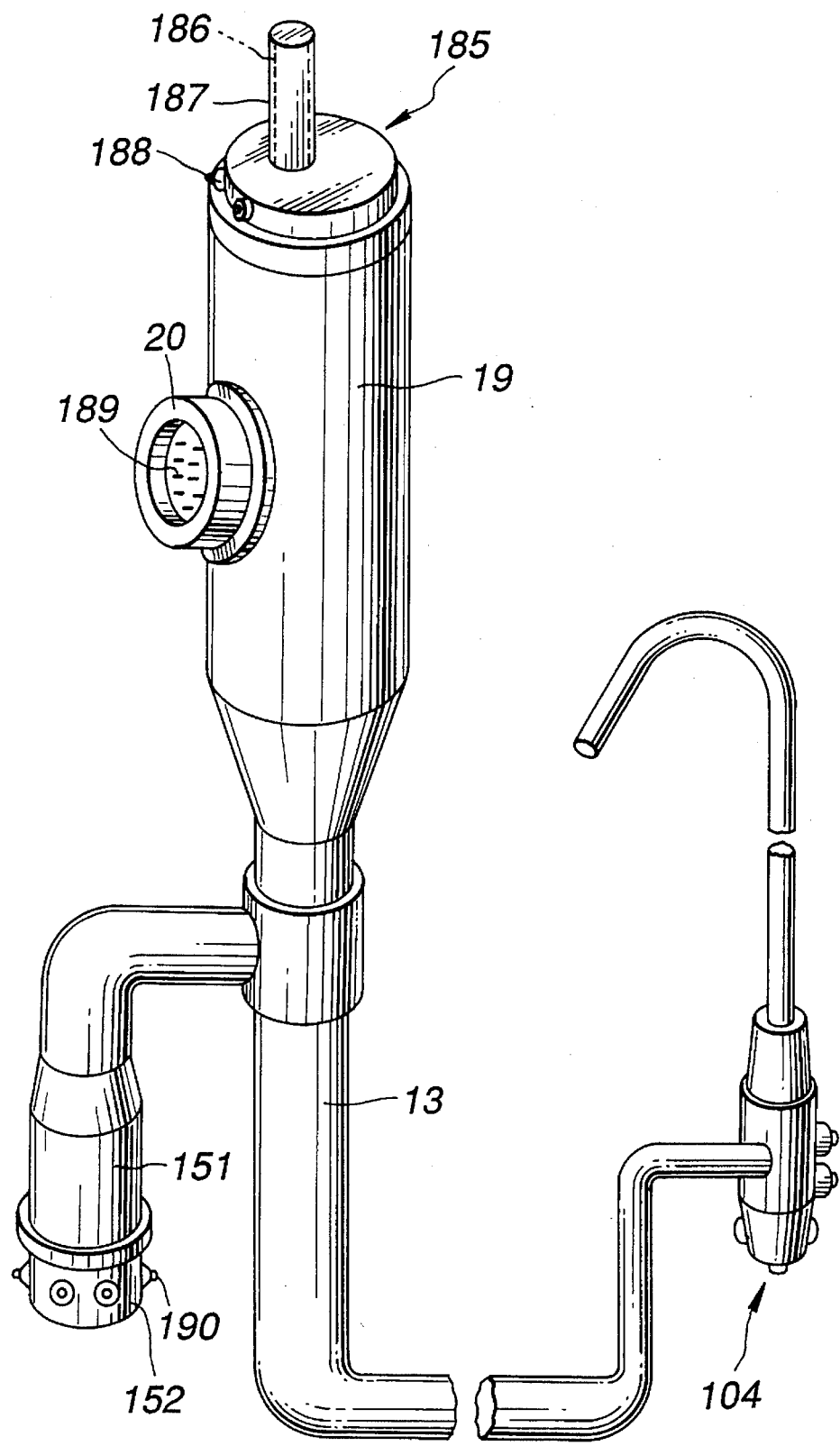
FIG. 22 is an explanatory diagram showing construction near a connector provided at an universal cord end of an endoscope to be covered.

FIG. 22 shows the construction near the connector 19 at the end of the universal cord 13 of the endoscope to be covered.

In the connector 19 provided in one end of the universal cord 13, a light source connector portion 185 connected to the light source device 7 and the electric connector portion 20 to which the signal cable 21 connected to the video processor is connected are arranged. A light guide 186 for transmitting illuminating light is projected from the rear end portion of the light source connector portion 185. On the side surface of the light source connector portion 185, a connecting pin for light source 188 for transmitting a signal for photographing to the light source device 7 is provided and a light guide cover 187 covering the light guide 186 is provided. A connecting pin for video 189 for transmitting a supplying air and water and sucking control signal to the fluid controlling device 9 is provided on the inside of the electric connector portion 20.

A second electric connector 151 positioned on the other end of the branched universal cord 13 is provided with a second electric connector portion 152. On the side surface of the second electric connector portion 152, a connecting pin for fluid controlling 190 which transmits a supplying air and water supplying control signal to the fluid controlling device 9 is provided.

Figure 23:
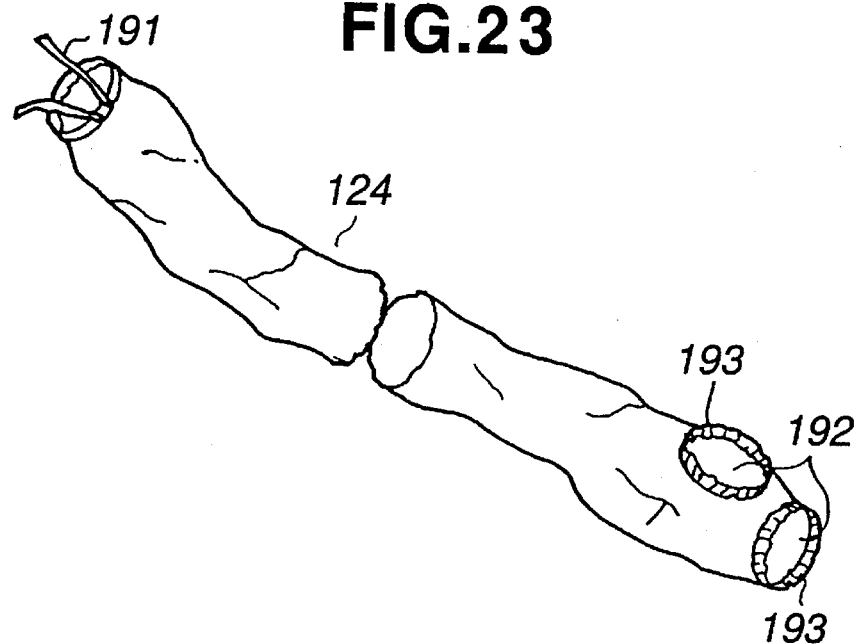
FIG. 23 is an explanatory diagram showing the whole construction of an universal cord cover portion.

FIG. 23 shows the whole construction of an universal cord cover portion 124.

A string 191 made of synthetic fibers is bound at the end of the universal cord cover portion 124 on the side of the operation part of the endoscope to be covered 12. When the universal cord cover portion 124 is fitted, the cord 124 is fixed to the endoscope to be covered 104 by binding the cord 191. A hole 192 corresponding to the positions of the light source connector portion 185 of the endoscope to be covered and the electric connector portion 20 is provided at the other end of the universal cord cover portion 124 at the end of the endoscope connector 19 to be covered. On the rim of the hole 192, pressing member 193 made of an elastic material is provided so as to tightly fit the marginal part of the hole 192 to the light source connector portion 185 or the electric connector portion 20.

Figure 24:
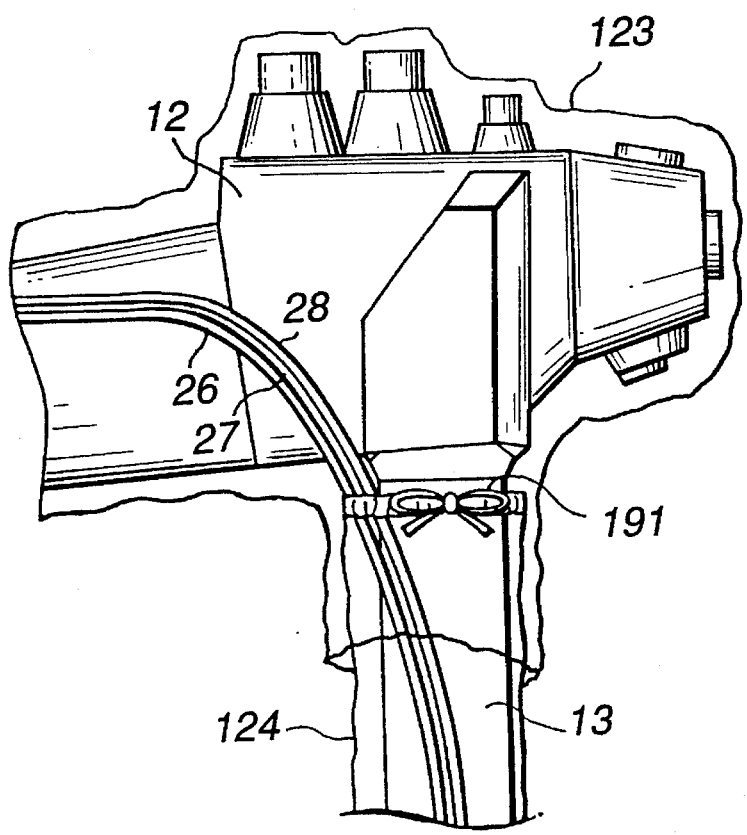
FIG. 24 is an explanatory diagram showing an area near an operation part of an endoscope to be covered in a state of the endoscope to be covered being covered with an universal cord cover portion.
Figure 25:
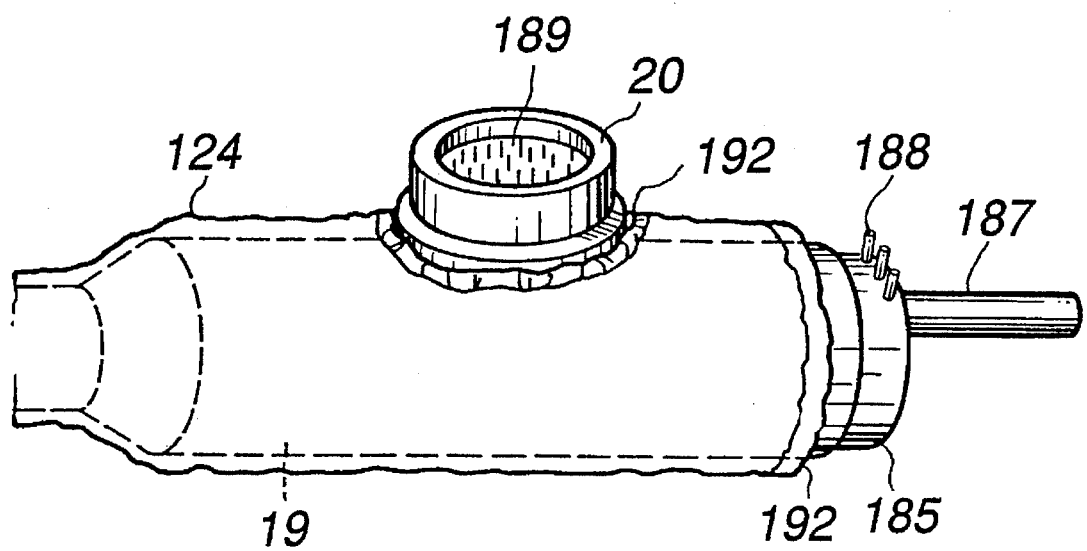
FIG. 25 is an explanatory diagram showing an area near a connector of an endoscope to be covered in a state of the endoscope to be covered being covered with an universal cord cover portion.

FIGS. 24 and 25 show the states in which the universal cord cover portion 124 covers the endoscope to be covered 104.

FIG. 24 shows the portion near the operation part 12 of the endoscope to be covered. When the universal cord 13 of the endoscope to be covered 104 is covered, the universal cord cover portion 124 is inserted into the universal cord 13 from the side of the string 191. After the cover 124 covers the distal end portion to the proximal end portion of the operation part 12, the string 191 is bound near the operation part 12 as shown in FIG. 24. Then, the operation part 12 of the endoscope to be covered is covered with the operation part cover portion 123.

FIG. 25 shows the portion near the connector 19 of the endoscope to be covered. Although the main body of the connector 19 is covered with the universal cord cover portion 124, the light source connector portion 185 and electric connector portion 20 which are connected with the light source device 7 and the signal cable 21 hard to be contaminated are exposed from the hole 192 to the outside, so that the light source device 7 and the signal cable 21 are surely connected to the light source connecting pin 185 and video connecting pin 189.

Thus, on the side of the connector 19 of the endoscope to be covered 104 of the universal cord cover portion 124, the portion which is covered with the light source device 7 or signal cable 21 and difficult to be contaminated is exposed by providing the hole 192. Therefore, a light source connecting pin 188 connected to a light source device 7 and the video connecting pin 189 connected to the signal cable 21 are exposed without being covered with the universal cord cover 124. Accordingly, an imperfect contact is not caused and a signal can be surely transmitted.

Further, because of the pressing member 193 provided on the marginal portion of the hole 192, the universal cord cover portion 124 is tightly fitted to the proximal ends of the exposed portions of the light source connector portion 185 and electric connector portion 20 so that the inside is covered and not to be exposed, the portions except for the aforesaid exposed portions are surely covered with the universal cord cover portion 124 not to be contaminated.

Figure 26:
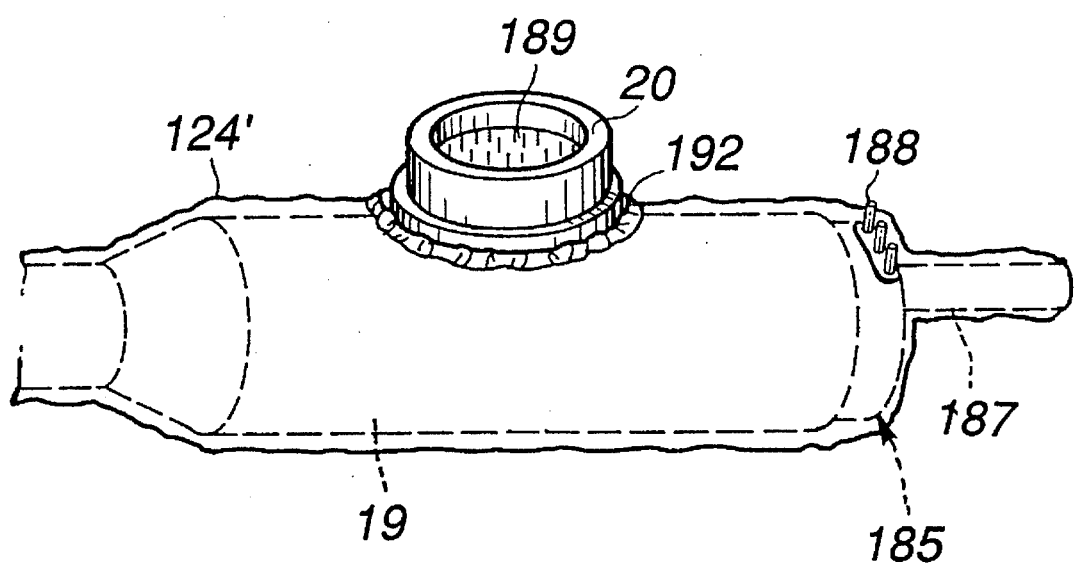
FIG. 26 is an explanatory diagram showing an area near a connector of an endoscope to be covered in a state of a modification of an universal cord cover portion being covered.

As shown in FIG. 26, as a modification 124' of the universal cord cover portion, tile hole 192 at the end of the universal cord cover portion 124' is provided only in a position corresponding to the electric connector portion 20 and the light source connector portion 185 is covered, and then only the tip of the light guide cover 187 of the light source connector portion 185 and a portion corresponding to the light source connecting pin 188 may be opened to be exposed.

Figure 27:
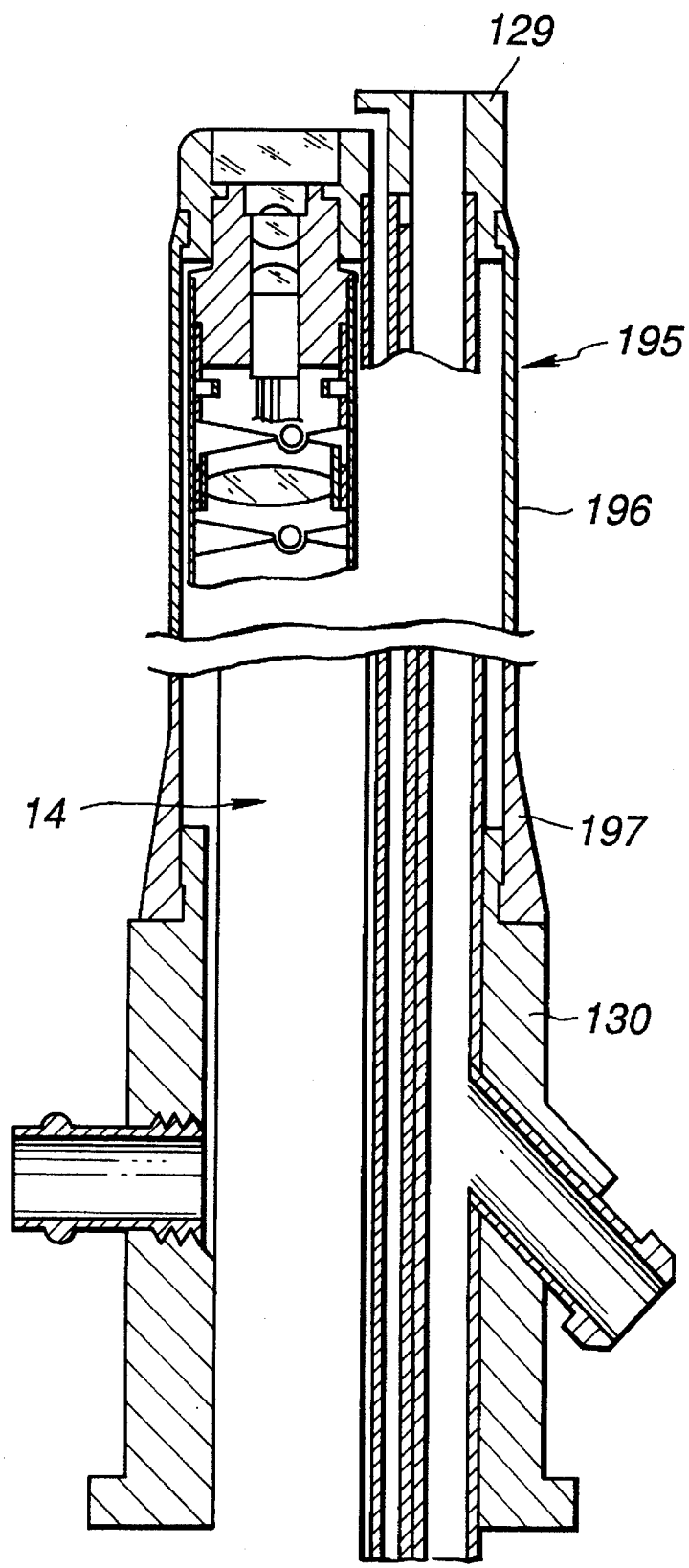
FIGS. 27 and 28 relate to the fourth embodiment of the present invention.
Figure 28:
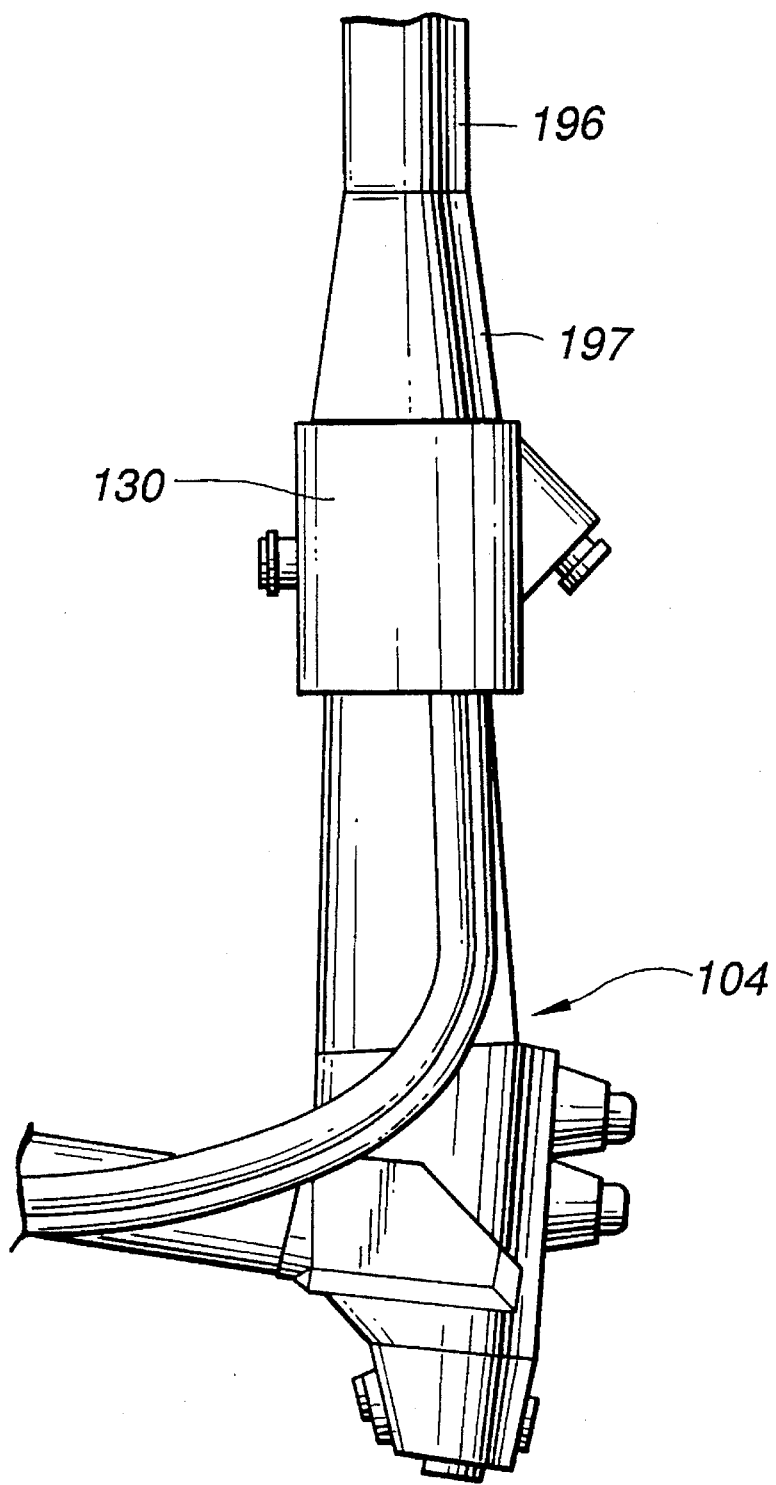

FIGS. 27 and 28 relate to the fourth embodiment of the present invention. FIG. 27 is a sectional view showing the construction of the insertion tube of the endoscope apparatus of an endoscope cover type. FIG. 28 is an explanatory diagram showing the construction of the insertion tube cover portion in a state in which the endoscope to be covered is inserted.

The fourth embodiment is a modification of the construction of the preventing member 170 provided in the third embodiment.

As shown in FIG. 27, a cover tip portion 129 and connector for fixing the endoscope operation part 130 are provided at both ends of an insertion tube cover portion 195 in the same manner as that of the third embodiment. The cover tip portion 129 and the connector for fixing the endoscope operation part 130 are tightly connected with an insertion tube cover exterior 196 which is made of thin and soft resin for separating an insertion tube 14 of an endoscope to be covered 104 from surroundings.

As shown in FIGS. 27 and 28, the ends of the portion near the insertion tube cover exterior 196 and the connector for fixing the endoscope operation part 130 changes such that the wall thickness thereof becomes thicker like a taper shape to form a preventing portion for preventing the insertion tube for breaking 197. The other construction is similar to the third embodiment and the explanation will be omitted.

In this way, the wall thickness of the proximal end portion of the insertion tube cover exterior 196 is changed to be thicker like a taper shape and the preventing portion 197 is provided, so that it prevents the insertion tube from bending at the proximal end or bending and transforming in the horizontal direction. Therefore, insertability can be improved.

Figure 29:
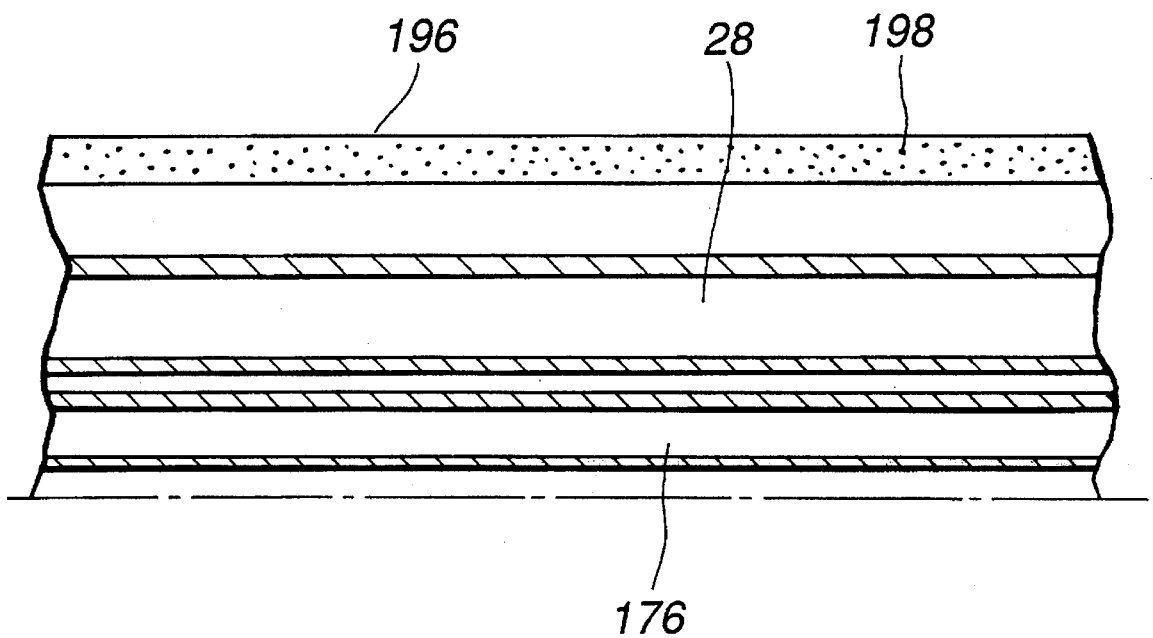
FIG. 29 is a sectional view showing a construction example of an exterior of an insertion tube cover in an insertion tube cover portion of an endoscope apparatus of an endoscope cover type.

The color of the insertion tube cover portion is changed to be black by forming the insertion tube cover exterior as shown in FIG. 29.

An insertion tube cover exterior 196 of the insertion tube cover portion 195 is made of thermoplastic elastomer. A large quantity of carbon 198 is mixed in the thermoplastic elastomer in the insertion tube cover exterior 196.

Because the apparatus is formed in this manner, the insertion tube cover exterior 196 becomes black, the diameter of the insertion tube cover portion 195 can be visually felt narrow.

If the insertion tube cover portion is bright color, such as white, the diameter of the insertion tube cover portion is visually felt thicker than the actual size. Then, there was a problem in that it gave an extreme fear to a patient. However, the black color of the insertion tube cover portion is visually felt narrow and can give a sense of security to a patient. Thus, an operator can insert the tube smoothly.

FIGS. 30 to 55 show tile fifth embodiment of the present invention.

Figure 30:
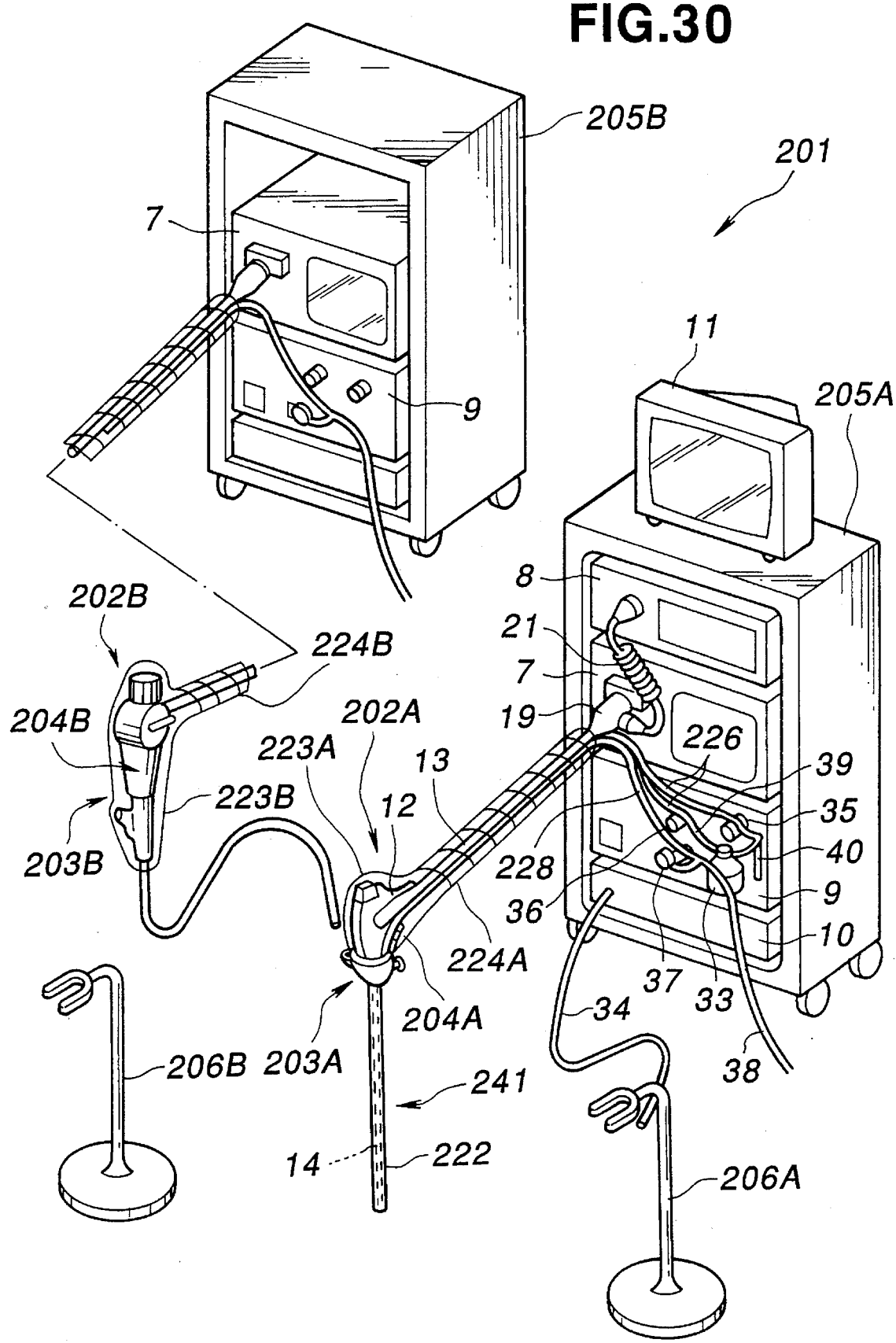

As shown in FIG. 30, an endoscope apparatus of an endoscope cover type 201 of tills embodiment comprises an endoscope of a cover type 202A, a second endoscope of a cover type 202B which has a narrow insertion tube into which a forceps channel of the endoscope of a cover type 202A is inserted in order to insert a tube into a thin object to be examined, such as a biliary duct into which the endoscope of a cover type 202A cannot be inserted. That is, the endoscope apparatus 201 is an apparatus of a parent and child scope type in which tile endoscope of a cover type 202A is a parent scope and the second endoscope of a cover type 202B is a child scope. Also, the same reference numerals are given to the same constructional elements as the elements of the first endoscope and tile explanation will be omitted.

The endoscope of a cover type 202A is formed by combining an endoscope cover 203A and an endoscope to be covered 204A which is fitted to the endoscope cover 203A. At the endoscope examination, the insertion tube of the endoscope to be covered with a clean cover 203A. After the examination, the cover 203A is thrown away. At the same time, the endoscope to be covered 204A is covered with a new cover 203A and repeatedly used.

The second endoscope of a cover type 202B is formed in the same way as the mentioned above by combining an endoscope cover 203B and an endoscope to be covered 204B which is fitted to the cover 203B.

The aforesaid endoscope apparatus 201 comprises the endoscope of a cover type 202A, a cart 205A containing various kinds of surrounding instruments to which the endoscope of a cover type 202A is connected and a cover holder 206A which holds the endoscope of a cover type 202A. Also, the endoscope apparatus 201 comprises the second endoscope of a cover type 202B, a cart 205B containing various kinds of surrounding instruments to which the second endoscope of a cover type 202B is connected and a cover holder 206B which holds the second endoscope of a cover type 202B.

The cart 205A contains, for example, a light source device 7, video processor 8, fluid controlling device 9 and endoscope cover expander 10. The cart 205B contains, in the same way as that of the cart 205A, a light source device 7, and a fluid controlling device 9.

The cover 203A has an insertion tube cover portion 222 made of thin and soft resin or the like, an operation part cover portion 223A and an universal cord cover portion 224A which are made of thin and soft polymer, such as vinyl chloride. These cover portions cover an endoscope insertion tube of endoscope 14, operation part 12 and universal cord 13 of an endoscope to be covered 204A, respectively.

The cover 203B fitted to the second endoscope of a cover type 202B has an operation part cover portion 223B and universal cord cover portion 224B which are made of thin and soft polymer, such as vinyl chloride. These cover portions cover the operation part and universal cord of the endoscope to be covered 204B, respectively.

The fluid controlling device 9 is provided with a supplying air controlling valve 35, supplying water controlling valve 36 and sucking controlling valve 37 to control supplying air and water and sucking. The supplying air controlling valve 35 and supplying water controlling valve 36 are connected to two fluid channels 226 extended from the insertion tube cover portion 222. The sucking controlling valve 37 is connected to a sucking channel 228 extended from an insertion tube cover portion 222.

Figure 31:
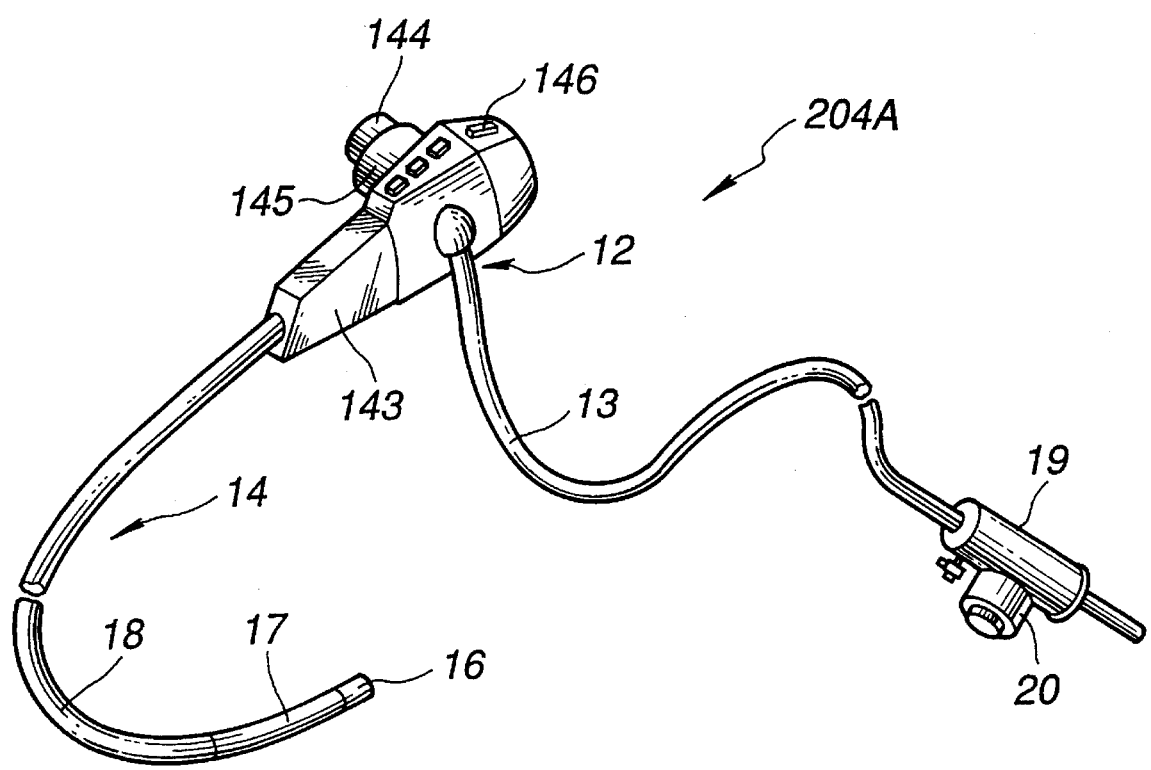

FIG. 31 shows the whole construction of the endoscope to be covered 204A.

In the same way as in the third embodiment shown in FIG. 14, the insertion tube 14 and the universal cord 13 are connected as if the tube 14 and the cord 13 are extended from the operation part 12. A connector 19 is provided at the end of the universal cord 13. On the surface of the connector 19, an electric connector portion 20 is provided. A signal cable 21 connecting a video processor 8 is connected to the electric connector portion 20. That is, in comparison with the third embodiment, the universal cord 13 is made of a cable which is not branched into two parts. The insertion tube 14 contains a flexible tube 18, having elasticity and flexibility, which transmits an operator's twisting operation and pressing and pulling operation to the tip.

Figure 32:
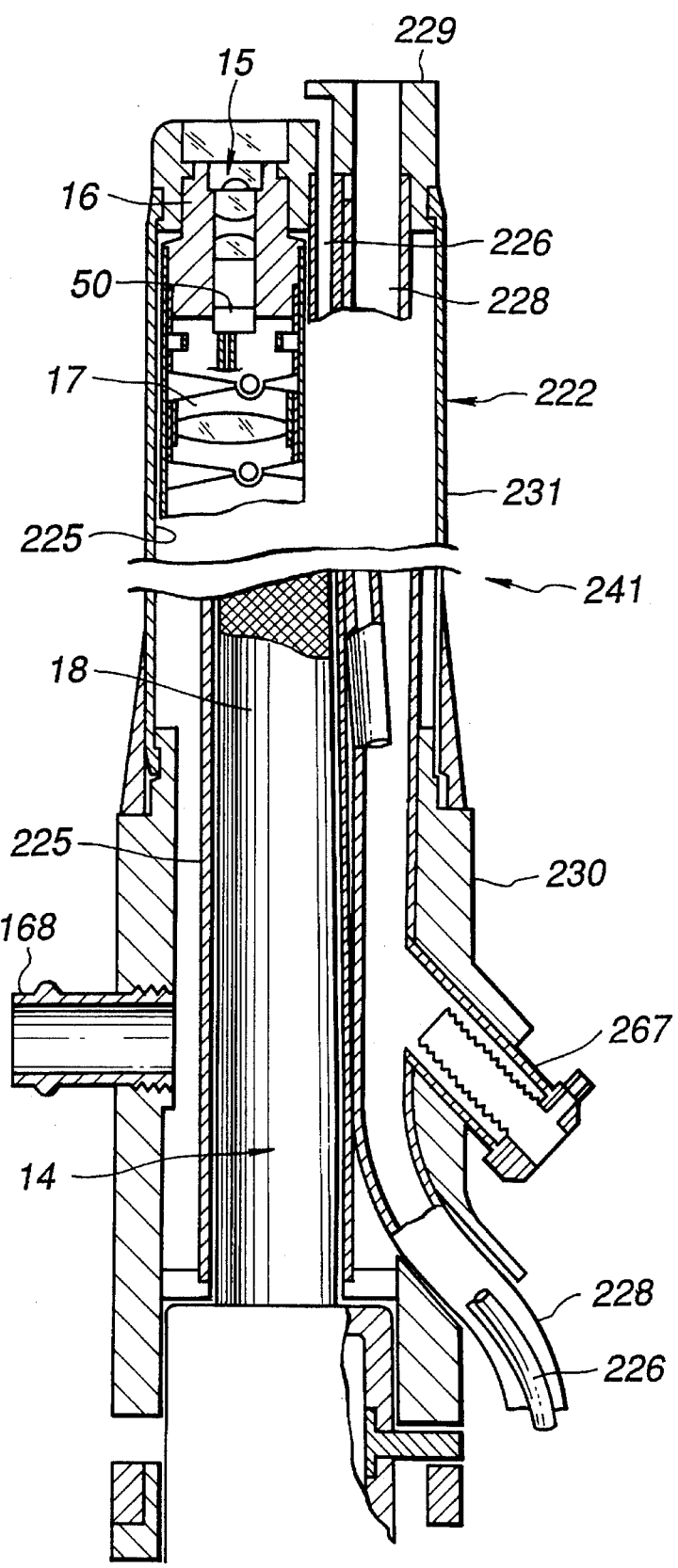

FIG. 32 shows a sectional view of an insertion tube 241 of an endoscope apparatus of an endoscope cover type in which the insertion tube cover portion 222 covers the endoscope to be covered 204A.

The insertion tube 241 of the endoscope apparatus of an endoscope cover type mainly contains the insertion tube cover portion 222 and insertion tube 14 of the endoscope to be covered.

The insertion tube cover portion 222 is provided with a sucking channel 228 which serves as the fluid channel 226 and forceps channel, and an endoscope insertion channel 225 to which the endoscope insertion tube 14 is inserted. The tips of these channels are to be connected with a cover tip portion 229 which is made of hard resin or the like.

As shown in FIG. 32, an insertion tube cover exterior 231 made of thin and soft resin for separating the insertion tube 14 of the endoscope to be covered 204A from surroundings is tightly connected to the cover tip portion 229.

At the proximal end of the insertion tube cover exterior 231, a connector for fixing an endoscope operation part 230 having a forceps insertion entrance 267 and expanding tube connector 168 to which an expanding tube 34 provided at the expander 10 is connected is provided. Then, the proximal end portion of the insertion tube cover exterior 231 is tightly connected to the insertion tube cover portion 222. At the proximal end of the connector for fixing the endoscope operation part 230, an opening portion of the endoscope insertion channel 225 to which an endoscope insertion tube 14 is inserted is tightly provided. Further, channels, such as the fluid channel 226 and sucking channel 228 are projected. The end of a fluid channel 226 opens to the cover tip portion 229.

The fluid channel 226, sucking channel 228 and endoscope insertion channel 225 have multilayer structure. The inner layer is made of a thin smooth film, such as polytetrafluoroethylene and the outer layer is made of a soft material, such as spread polytetrafluoroethylene and silicone tube.

Figure 33:
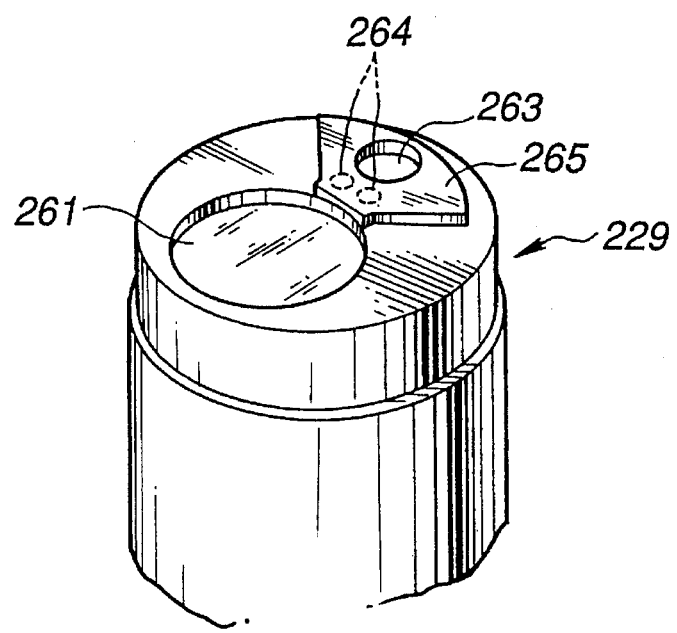

At the cover tip portion 229, as shown in FIG. 33, an observation window 261 made of transparent glass or resin so as to transmit light is tightly fitted to a position facing an observation optical system 15 (see FIG. 32) and illumination optical system (not illustrated) of the endoscope to be covered 204A. Further, a supplying air and water nozzle 265 opening toward the observation window 261 is provided. A forceps entrance 263 joined to the sucking channel 228 is provided. From the forceps entrance, forceps (not illustrated) are projected. Two fluid spouting nozzles 264 joined to the fluid channel 226 are provided under the supplying air and water nozzle 265.

Only at the connector for fixing endoscope operation part 230, the proximal end of the endoscope insertion channel 225 opens to the outside and other portions of the channel 225 are not exposed to the outside. Accordingly, when the endoscope insertion tube 14 is inserted into the insertion tube cover portion 222, the insertion tube 14 except for its proximal end is covered with the insertion tube cover exterior 231 and not exposed to the outside.

Figure 34:
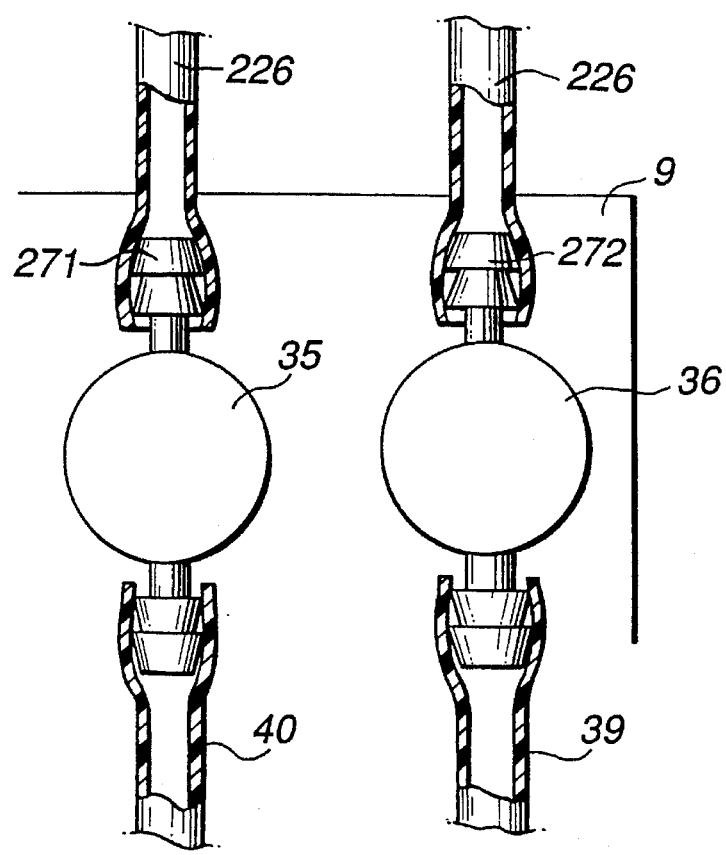

FIG. 34 shows the construction of the connected portion between the fluid controlling apparatus 9 and fluid channel 226.

A supplying air connector 271 and supplying water connector 272 are arranged on the supplying air controlling valve 35 and supplying water controlling valve 36 provided in the fluid controlling device 9. The supplying connector 271 and supplying water connector 272 have the same shape. The fluid channels 226 having the same length, inside diameter and wall thickness are connected to the supplying air connector 271 and supplying water connector 272. A supplying air tube 40 is connected to the other end of the supplying air controlling valve 35. A supplying water tube 39 is connected to the other end of the supplying water controlling valve 36.

When air is supplied by means of the fluid controlling device 9, the supplying air controlling valve 35 opens although it is usually closed. The air supplied from a supplying air tube 40 passes through one of the fluid channels 226 connected to the supplying air connector 271 by way of the supplying air connector 271 from the supplying air controlling valve 35, and spouted from one of the fluid channel spouting nozzles 264 which is an opening portion of the cover tip portion 229 of the fluid channels 226, so that air is supplied in the direction of the observation window 261 by means of the supplying air and water nozzle 265.

When water is supplied, the supplying water controlling valve 36 opens although it is usually closed. The water from a supplying water tank 33 supplied by a supplying water tube 39 passes through the other fluid channel 226 connected to the supplying water connector 272 by way of the supplying water connector 272 from the supplying water controlling valve 36, and spouted from the other fluid channel spouting nozzle 264, so that water is supplied in the direction of the observation window 261 by means of the supplying air and water nozzle 265.

A supplying air channel and supplying water channel are provided as a fluid controlling system in the endoscope apparatus of an endoscope cover type. The construction in which it is generally considered that these channels are connected to a supplying air connected portion of the supplying air controlling valve and supplying water connected portion of the supplying water controlling valve, respectively. These connected portions are provided in the fluid controlling device. In this case, the supplying air channel and supplying water channel are connected to the opening portion for supplying air and an opening portion for supplying water, respectively, so as to satisfy the functions of supplying air and water. These opening portions are provided at the cover tip portion.

At the same time, when such endoscope apparatus of an endoscope cover type is used, the aforesaid supplying air channel and supplying water channel are connected to the supplying air connected portion and supplying water connected portion of the fluid controlling device, respectively. Since the outward appearances of these channels were difficult to be differentiated, it took time to differentiate these channels when connected or there was danger that wrong channel was connected. In addition, there was a case that favorable quantity of supplying air and water could not be acquired by erroneously connecting the supplying air channel to the supplying water connected portion or the supplying water channel to the supplying air connected portion and that reliable control for supplying air and water could not be performed.

In this embodiment, as shown in FIG. 34, the supplying air connector 271 and supplying water connector 272 in the connected portion of the fluid controlling device 9 and the fluid channel 226 have the same shape. Therefore, when the fluid channel on the endoscope cover side is connected, it is not necessary to differentiate the channels for supplying air or supplying water. Either fluid channel can be connected to the supplying air controlling valve 35 and supplying water controlling valve 36. Accordingly, it saves time for differentiating the channels when connected and maneuverability can be improved. Even if either fluid channel 226 is connected to the supplying air connector 271 and supplying water 272, sufficient supplying air and water capacity can be demonstrated.

Thus, the burden of an operator can be reduced when the operator covers the endoscope to be covered 204A with the insertion tube cover portion 222 when used, and connects the fluid channel 226 extended from the insertion tube cover 222 to the fluid controlling device 9. Also, because the supplying air connector 271 and supplying water connector 272 are made of the same material and use the same two fluid channels 226, the cost price of material and assembling can be reduced.

Although the example in which two fluid channels 226 are independently provided to the cover tip portion 229 is stated, it may be formed such that two fluid channels join in the insertion tube cover portion and only one channel is inserted to the tip portion.

Figure 35:
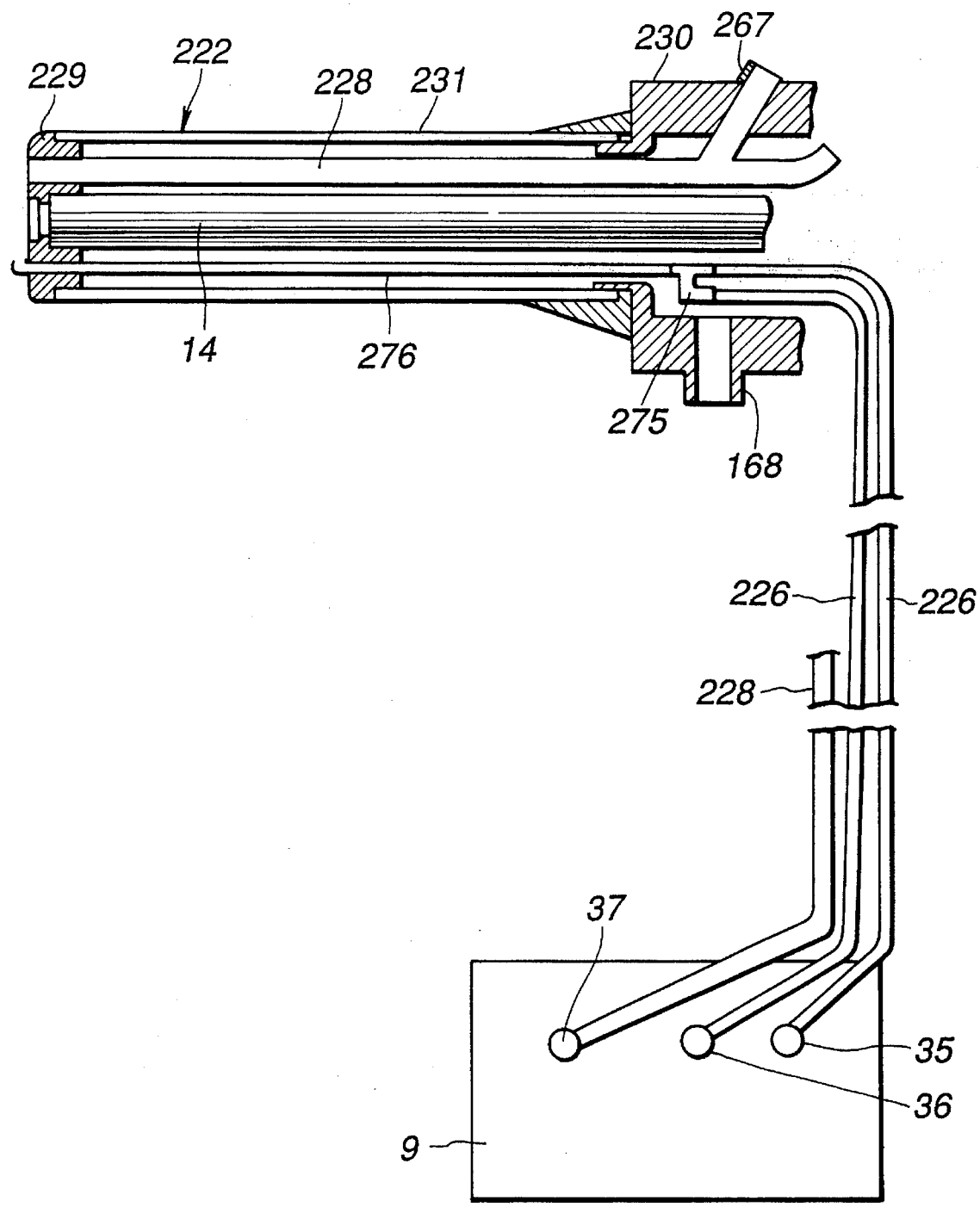

Such constructional example is shown in FIG. 35.

The two fluid channels 226 connected to the fluid controlling device 9 are connected to, for example, a connecting tube 275, which is made of hard resin and provided within a connector for fixing endoscope operation part 230, and joined to be one channel. A supplying air and water channel 276 is connected to the other end of the connecting tube 275 and open at the tip portion of the insertion tube cover portion 222.

By such construction, the fluid channel 226 can be connected to the controlling valve of tile fluid controlling device 9 without differentiating the channels in the same way as the aforesaid, and the channel within the insertion tube cover portion 222 can be reduced, so that the insertion tube cover portion 222 can be narrow.

Figure 36:
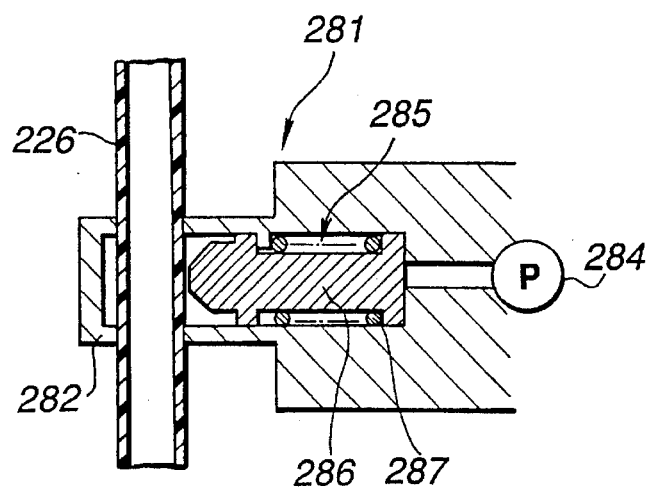
Figure 37:
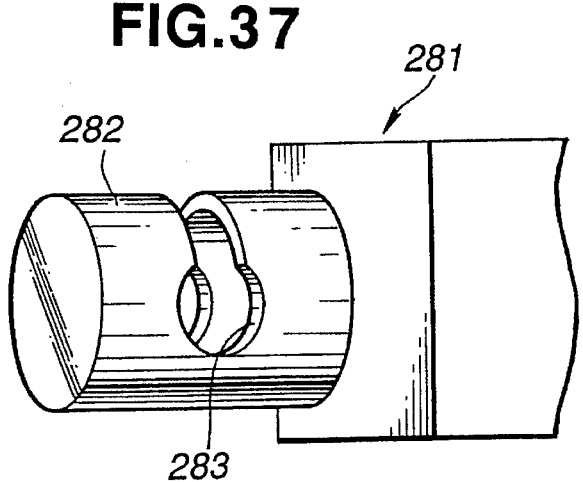

The connected portion of the fluid channel 226 and controlling valve is not limited to the construction in FIG. 34, but also may be connected to either controlling valve even if the inside diameter, outside diameter and wall thickness of two fluid channels are different as the construction shown in FIGS. 36 and 37.

FIG. 36 is a sectional view showing the connected portion of the fluid channels 226 in the supplying air controlling valve provided in the fluid controlling device 9. FIG. 37 is a perspective view showing the outward appearance of the supplying air controlling valve.

A supplying air controlling valve 281 has a chuck part 282 to which the fluid channel 226 is inserted. A notching hole 283 which is bored through the chuck part 282 in the side direction is provided, so that the fluid channel 226 is inserted into the notching hole 283. In the supplying air controlling valve 281, a cylinder 285 connected to an air pump is provided. In a cylinder 285, a controlling rod 286 which is movable in the axis direction is arranged. A spring member 287 is provided in a recess part on the surface of the controlling rod 286. Then, the end of the spring member 287 is fitted to the convex part on the surface of the cylinder 285. The controlling rod 286 is applied force in the direction of the air pump 284. The air pump 284 is connected to a supplying air and water sucking control switch 145 which is provided in the operation part 12 of the endoscope to be covered 204A through a supplying air controlling circuit (not illustrated) in the fluid controlling device 9.

The fluid channel 226 of the supplying controlling valve 281 opens at a state of FIG. 36. Then, air is supplied from a supplying air tube.

Figure 38:
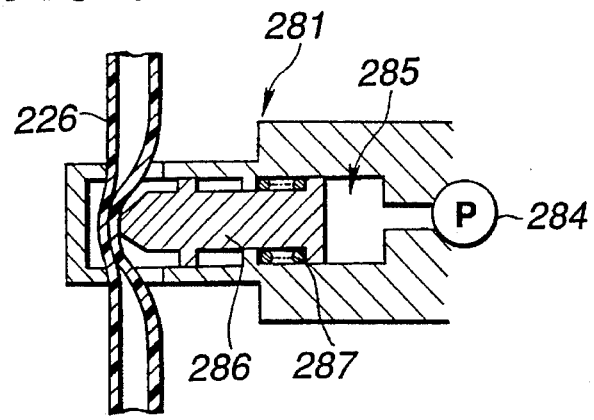

When it is designated to stop the air supply by operating the supplying air and water sucking control switch 145, air is supplied from the air pump 284 into the cylinder 285. The cylinder 285 presses the controlling rod 286 which is applied force upwards by pneumatic pressure using the spring member 287 and crushes the side surface of the fluid channels 226 as shown in FIG. 38. Thus, the flow of the fluid flowing in the channel stops.

Since the supplying water controlling valve has the same construction and operation, the explanation will be omitted.

Supplying air and water can be controlled by the supplying air and water controlling valves formed in this way. Because the fluid channels 226 do not have the structure in which the ends of the channels 226 are not connected, the two channels can be fitted to any controlling valves even if the inside diameter, outside diameter and wall thickness of the two channels are different from each other.

When the controlling valves shown in FIGS. 36 and 37 are used, the apparatus can be more resistant to pressure by connecting, for example, a silicon tube to the fluid channels 226 and inserting a silicon tube into the portion sandwiched by the chuck parts 282.

Figure 39:
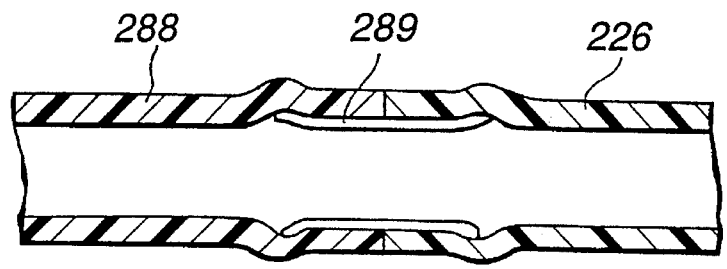

That is, as shown in FIG. 39, a silicon tube 288 is connected to the fluid channels 226 through a connecting pipe 289 and the portion of the silicon tube 288 is inserted to the chuck part 282, to be opened and closed. Both ends of the connecting pipe 289 is formed into a taper shape, so that the two tubes do not easily come off. Because of this, the resistibility of the tube for opening and closing of the controlling valve can be improved.

Figure 40:
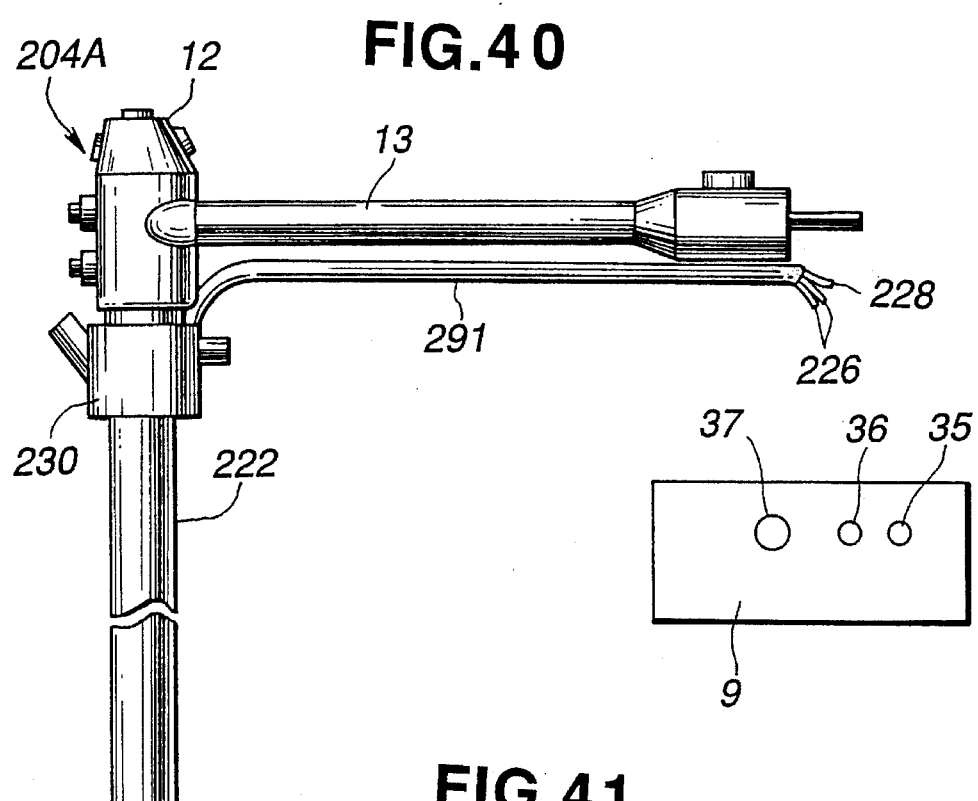
Figure 41:
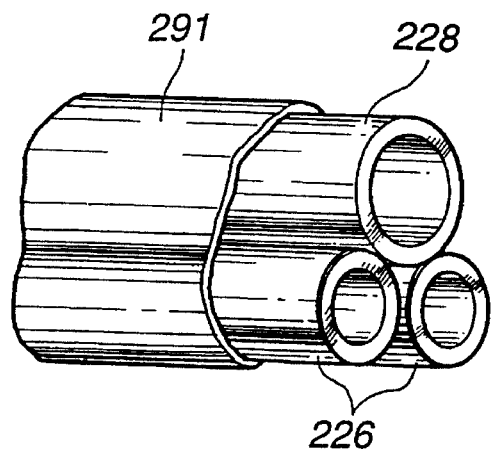

FIGS. 40 and 41 show the construction of the insertion tube cover portion 222 and the fluid channels extended from the insertion tube cover portion 222.

As mentioned above, a plurality of fluid channels, such as the fluid channels 226, and sucking channel 228 are provided in the insertion tube cover portion 222 of the endoscope apparatus of an endoscope cover type. These fluid channels are connected to the fluid controlling device 9.

In this embodiment, as shown in FIG. 40, the fluid channels 226 and the sucking channel 228 provided in the insertion tube cover portion of tile endoscope to be covered 14, are extended through the portion near the universal cord 13 of the endoscope to be covered. These fluid channels 226 and sucking channel 228 are covered with a thermo-contraction tube 291 as shown in FIG. 41 and joined to be one channel.

Figure 42:
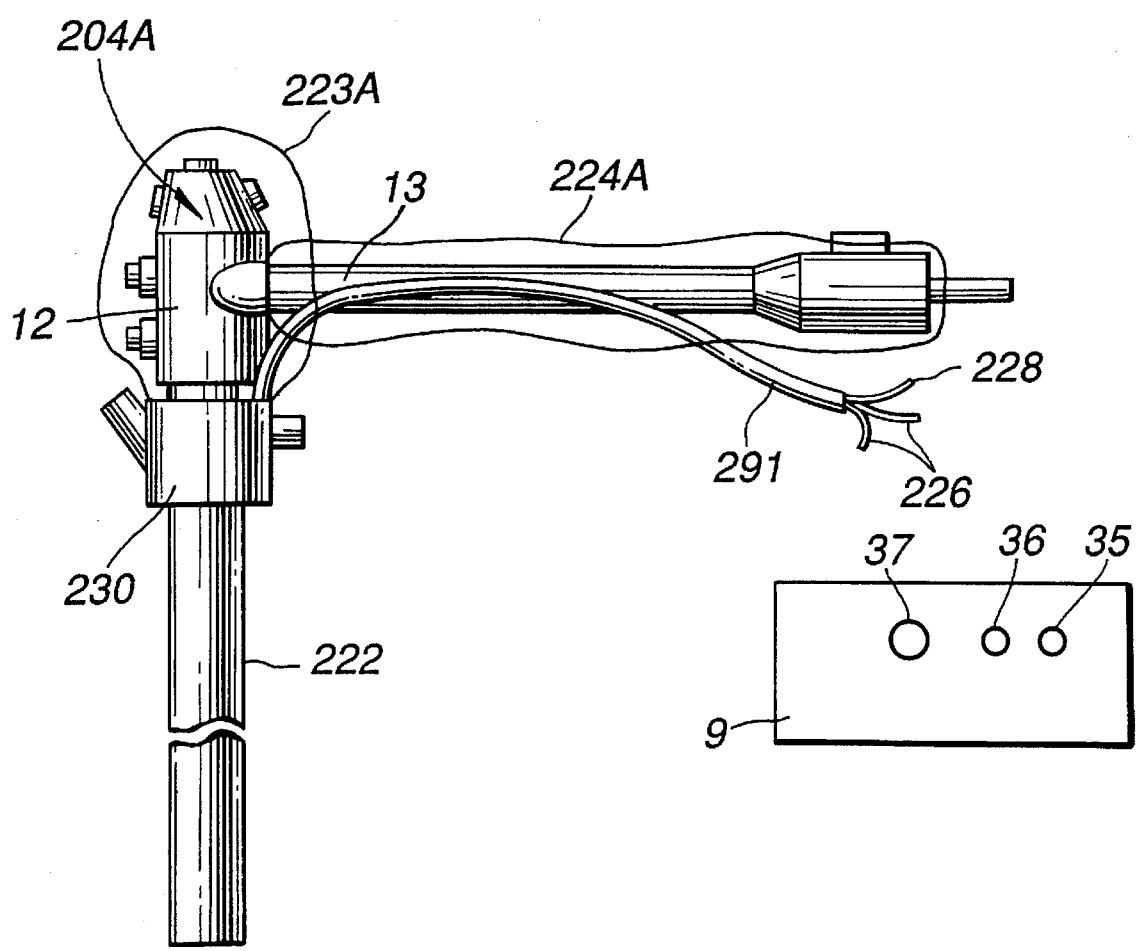

When the endoscope to be covered 204A to which tile insertion tube cover portion 222 is fitted is shown in FIG. 40 is covered with the insertion tube cover portion 223A and universal cord cover portion 224A, the whole shape is shown in FIG. 42. The operation part 12 of the endoscope to be covered 12 is covered with tile operation part cover portion 223A and the universal cord 13 and the thermo-contraction tube 291 extended along the universal cord 13 are covered with the universal cord cover portion 224A by binding the universal cord cover portion 224A.

In the endoscope apparatus of an endoscope cover type, if a plurality of fluid channels are separated into each channel, the plurality of fluid channels extended from-the insertion tube cover portion are separated or become bulky when the universal cord cover portion is bound round the universal cord of the endoscope to be covered, so that an operator who holds the channel along the universal cord is needed and maneuverability becomes quite worse.

At the same time, in this embodiment, the fluid channels 226 and sucking channel 228 are united by the thermo-contraction tube 291. Therefore, when the universal cord cover portion 224A covers the universal cord 13, fluid channel 226 and sucking channel 228, the channels are not separated or do not become bulky. Further, an operator who holds the fluid channels 226 and sucking channel 228 is not needed, so that maneuverability is quite good.

When the cord and channels are covered with a cover, one person can do it. There is no fear that an unclean person joins the operation and soils the universal cord cover portion 224A. Further, it is not necessary that an unclean person joins the operation and therefore, and that the operation is divided into a clean range and an unclean range. Thus, the operation becomes simple and maneuverability can be improved.

Figure 43:
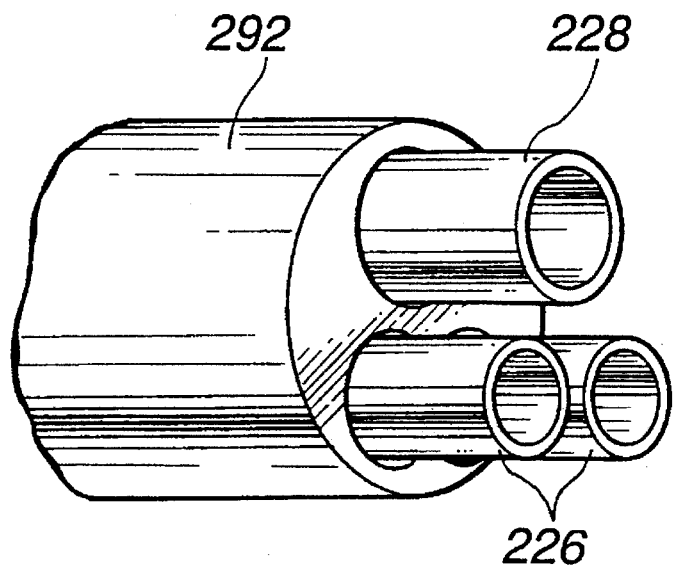
Figure 44:
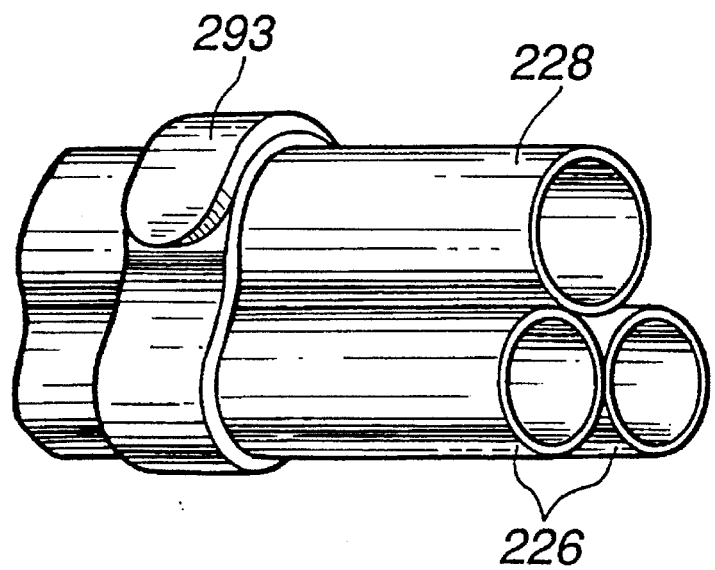

In the aforesaid construction, the thermo-contraction tube 291 is used as means for binding the fluid channels 226 and sucking channel 228; however, a multi-lumen tube 292 formed of elastic material as shown in FIG. 43 may be used and the fluid channels 226 and sucking channel 228 may be inserted into the multi-lumen tube 292. Parts of the fluid channels 226 and sucking channel 228 may be bound using a binding band 293 formed of elastic material as shown in FIG. 44 instead of binding the whole length of the channel.

Next, the construction of the connected portion between the connector for fixing endoscope operation part 230 of the proximal end portion of the insertion tube cover portion 222 and the operation part 12 of the endoscope to be covered will be explained.

Figure 45:
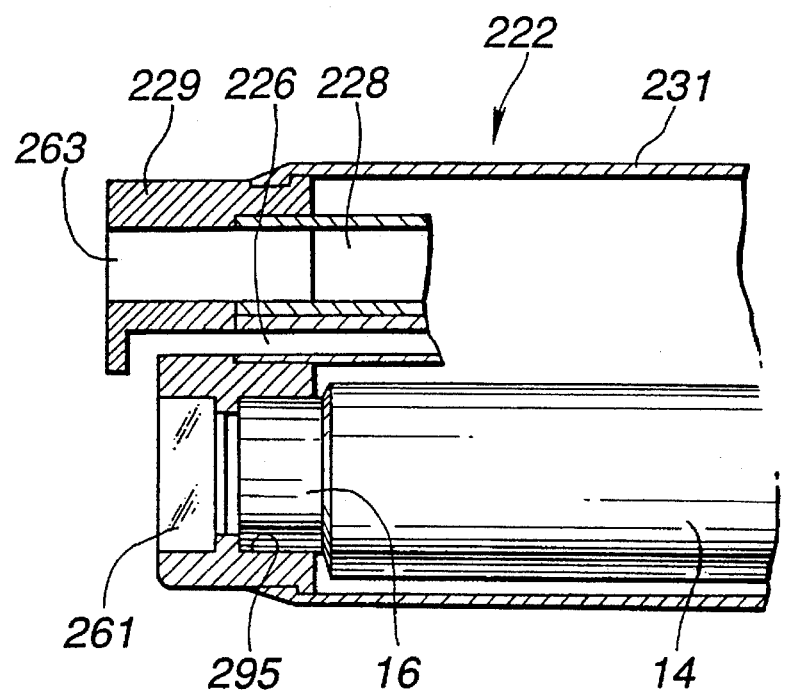

First, the construction of the tip portion of the insertion tube cover portion 222 in a state into which the insertion tube of the endoscope to be covered 14 is inserted is shown in FIG. 45.

The insertion tube cover portion 222 has a forceps entrance 263 joined to the sucking channel 228, and a cover tip portion 229 provided with an observation window 261. At the rear end of the observation window 261 of the cover tip portion 229, a recess part for connecting an endoscope tip portion 295 is provided so as to be fitted to the tip portion 16 of the endoscope insertion tube 14.

The recess part 295 is a circle shape. The inside diameter of the recess part 295 is made to be slightly wider than the outer diameter of the endoscope tip portion 16. Therefore, in a state of the endoscope tip portion 16 fitted to the cover tip portion 229, the tip portion 16 is rotatable to the cover tip portion 229.

Figure 46:
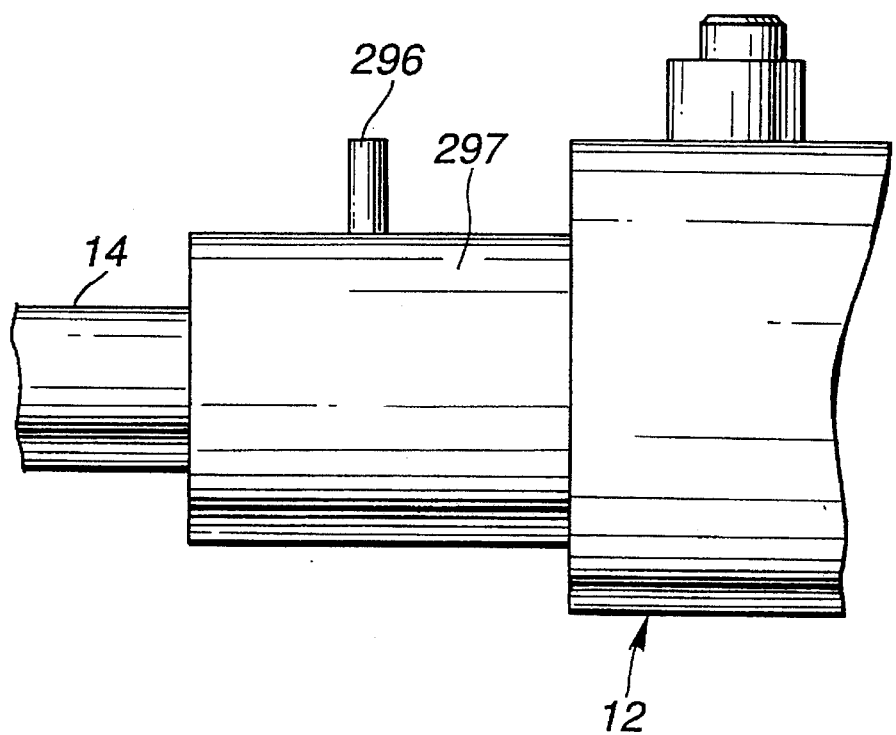

The connected portion between the insertion tube of the endoscope to be covered 204A inserted into the insertion tube cover portion 222 and the operation part 12 is formed as shown in FIG. 46.

In the insertion tube side end portion of the endoscope operation part 12, a cover fixing portion 297 over which a fixing pin 296 is projected is provided and the insertion tube 14 is connected to the tip of the cover fixing portion 297.

Figure 47:
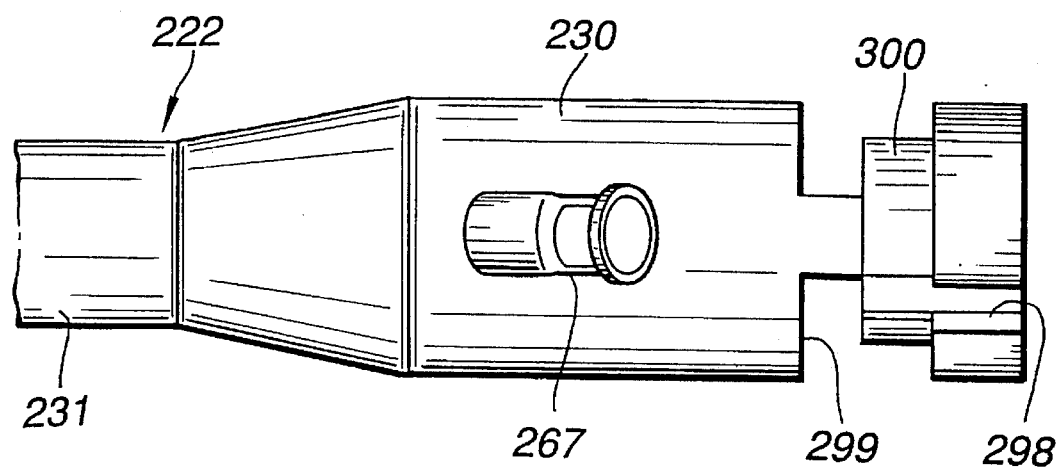

Then, the connector for fixing the endoscope operation part 230 of the proximal end portion of the insertion tube cover portion 222 is formed as shown in FIG. 47.

An insertion tube cover exterior 231 is tightly connected to the tip of the connector for fixing the endoscope operation part 230 mentioned above. A forceps insertion entrance 267 is provided at the side of the connector 230. The rear end (on the side of the endoscope operation part 12) of the connector 230 is provided with a guiding groove 298 which is formed in the axis direction to be engaged with the fixing pin 296 of the endoscope to be covered 204A, and a moving groove 299 which is formed like a circumference by connecting to the end of the guiding groove 298 and makes the fixing pin 296 engaged with the guiding groove 298 movable in the circumference direction. Further, the rear end side of the guiding groove 299 is circumferentially provided with a ring groove portion 300 with which a C ring is engaged to press the fixing pin 296 so that the fixing pin 296 in the moving groove 299 does not come off.

Figure 48:
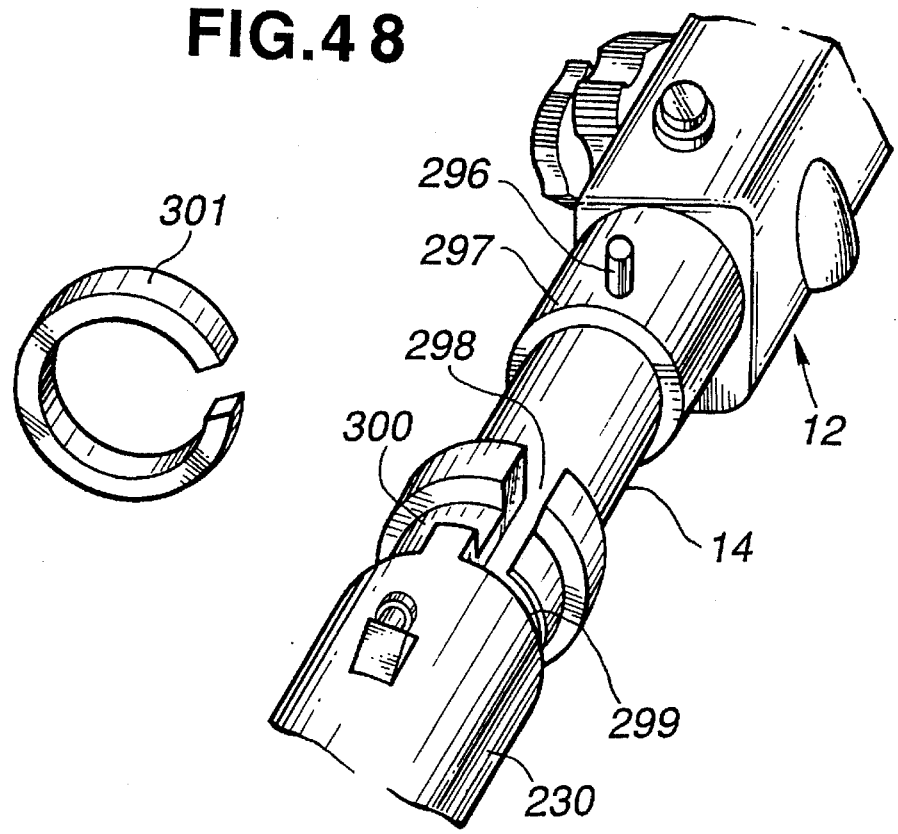
Figure 49:
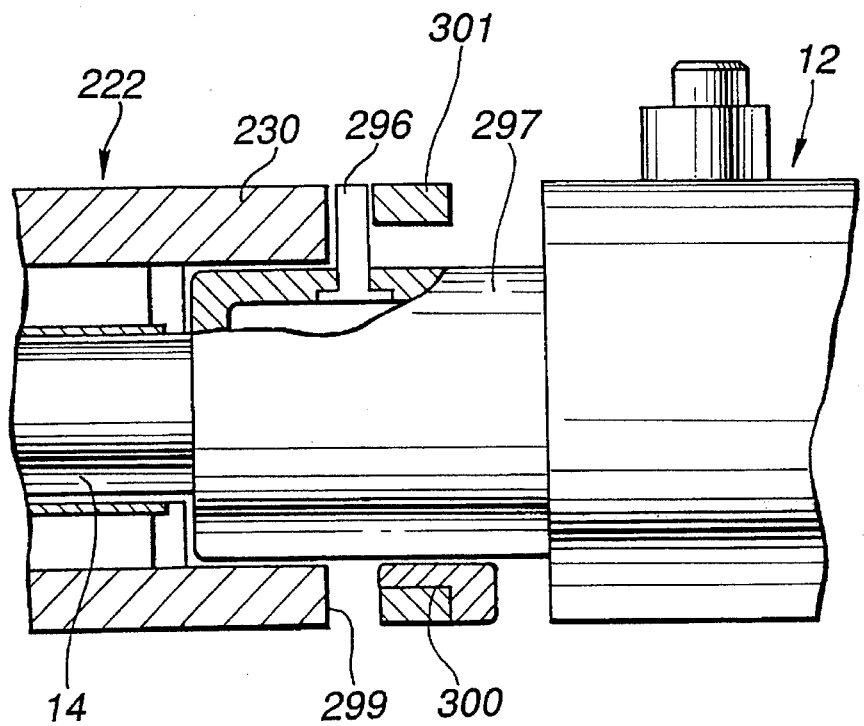
Figure 50:
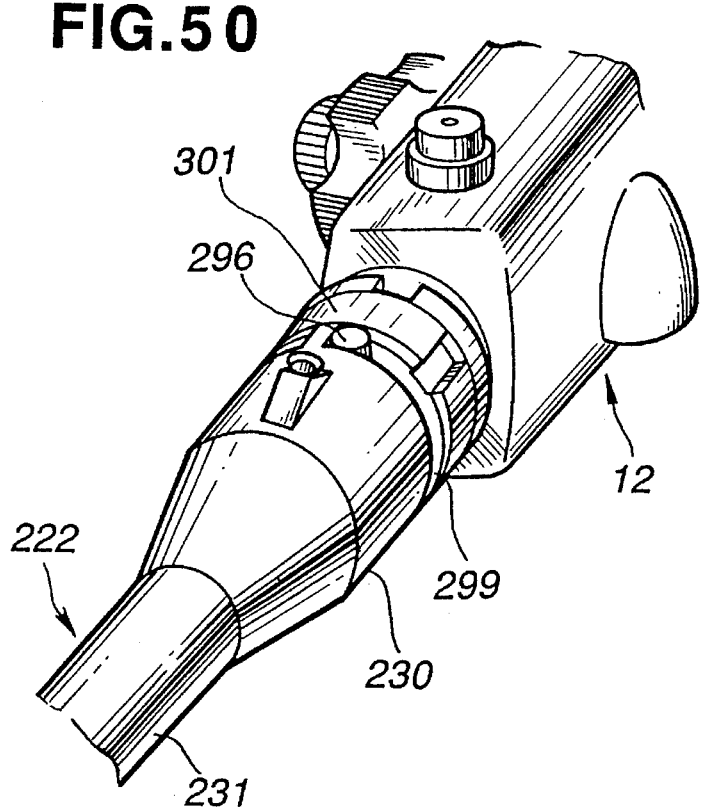

In the endoscope to be covered 204A and insertion tube cover portion 222 formed in this way, steps and a state when the insertion tube cover portion 222 is inserted into the endoscope to be covered 204A will be explained in reference to FIGS. 48 to 50. FIG. 48 shows a state when the insertion tube cover portion 222 is fitted to the endoscope to be covered 204A. FIG. 49 shows a sectional view of a state in which the insertion tube cover portion 222 is fixed to the endoscope to be covered 204A. FIG. 50 shows an outward appearance of a state in which the insertion tube cover portion 222 is fixed to the endoscope to be covered 204A.

The insertion tube 14 of the endoscope to be covered 204A is inserted into the proximal end portion in the insertion tube cover portion 222. The fixing pin 296 provided in the cover fixing portion 297 is engaged with the guiding groove 298 provided in the connector for fixing the endoscope operation part 230. Then, the fixing pin 296 is inserted into the moving groove 299 at the inner part of the guiding groove 298 and a C ring 301 is fitted into the ring groove 300 provided at the rear end side of the moving groove 299.

In a state where an insertion tube cover portion 222 is fixed to the endoscope to be covered 204A, as shown in FIGS. 49 and 50, because the fixing pin 296 is fixed in the axis direction by the C ring 301, the insertion tube cover portion 222 does not come off from the endoscope to be covered 204A.

In this state, the fixing pin 296 is movable along the moving groove 299. Therefore, the insertion tube of the endoscope to be covered 204A can be rotated in the circumference direction to the insertion tube cover portion 222. Because the insertion tube tip portion 16 of the endoscope to be covered is also rotatable to the cover tip portion 229 when the insertion tube 14 of the endoscope to be covered 204A is rotated, the insertion tube can be easily rotated to the tip portion by holding and rotating the operation part of the endoscope to be covered.

In the endoscope apparatus of an endoscope cover type, the construction which firmly fixes an endoscope by the cover tip portion and the connector for fixing the endoscope operation part is considered so that the insertion tube does not come off even if the endoscope operation part is rotated or twisted while the insertion tube is inserted into the body cavity. However, in this case, there was a problem that the insertion tube cover portion became thicker by providing means for firmly fixing the tip portion of the endoscope to be covered to the cover tip portion.

At the same time, in this embodiment, fixing means for fixing the endoscope to be covered 204A to the insertion tube cover portion 222 is provided. Thus, it is not necessary to provide firm fixing means at the cover tip portion 229. Then, the insertion tube of the endoscope apparatus of an endoscope cover type can be narrow.

Because the endoscope to be covered 204A is connected and fixed to the insertion tube cover portion 222 by the connector for fixing the endoscope operation part 230, the fixation of the endoscope to be covered 204A and the insertion tube cover portion 222 in the axis-direction becomes firmer. In addition, the endoscope to be covered 204A and the insertion tube cover portion 222 are rotatable, so that a bending direction can be finely changed by rotating the endoscope to be covered 204A to the insertion tube cover portion 222 and the improvement of the insertability can be expected.

Figure 51:
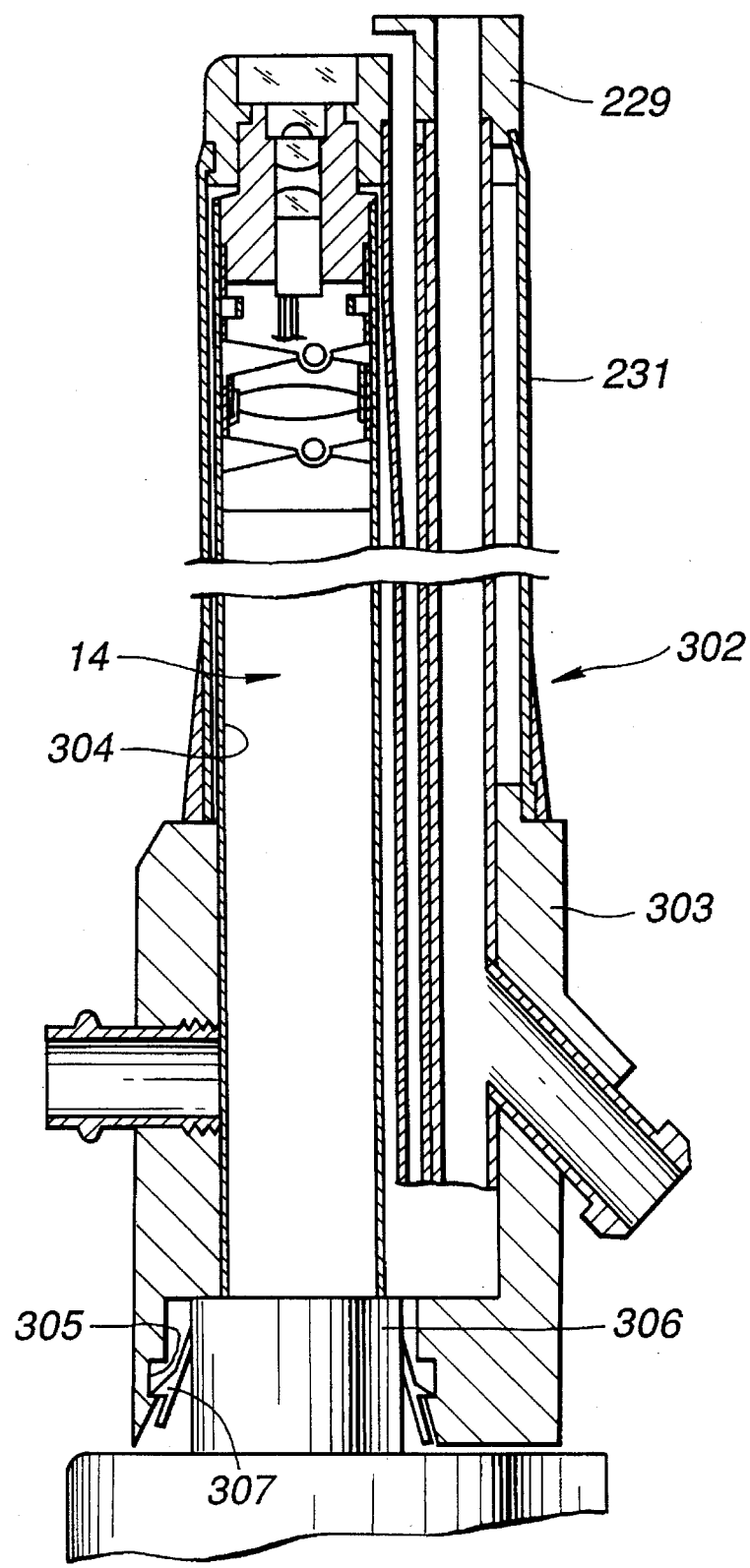

In the construction of the aforesaid embodiment, as shown in FIG. 32, the endoscope insertion channel 225 does not have the same axis on the distal end and proximal end of the insertion tube cover portion 222. However, the axes of the distal end and proximal end may be the same to reduce the resistance when the insertion tube of the endoscope is rotated. The construction of the modification of the insertion tube cover portion in which the endoscope insertion channel has the same axis at the distal end and proximal end is shown in FIG. 51.

A connector for fixing endoscope operation part 303 provided at the proximal end of an insertion tube cover portion 302 of this modification is provided with a groove portion 305 of a circumference shape on the side surface near tile opening portion at the rear end of the endoscope insertion channel 304. At the same time, a pair of snap fit portions 307 facing tile-side portion is projected over a cover fixing portion 306 at the proximal end of the endoscope insertion tube 14 inserted into the endoscope insertion channel 304. The snap fit portions are engaged with the groove portion 305 provided in the opening portion 303. Therefore, it prevents the endoscope insertion tube 14 coming off from the insertion tube cover portion 302.

Figure 52:
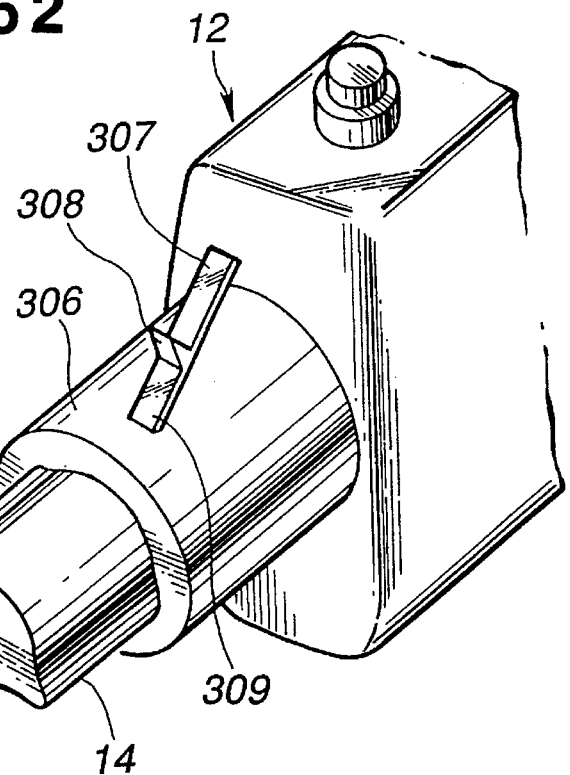

The proximal end portion 309 of the snap fit portion 307 is fixed to the cover fitting portion 306 as shown in FIG. 52. The middle portion of the snap fit portion is provided with a click 308. The click 308 is engaged with the aforesaid groove portion 305.

Figure 53A:
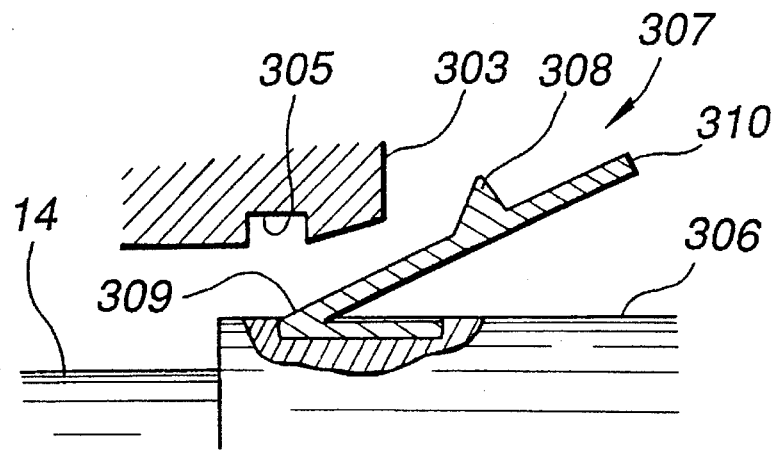
FIGS. 53(a), 53(b) and 53(c) are explanatory diagrams showing a state when the endoscope insertion tube of the modification shown in FIG. 51 is fitted into an insertion tube cover portion.
Figure 53B:
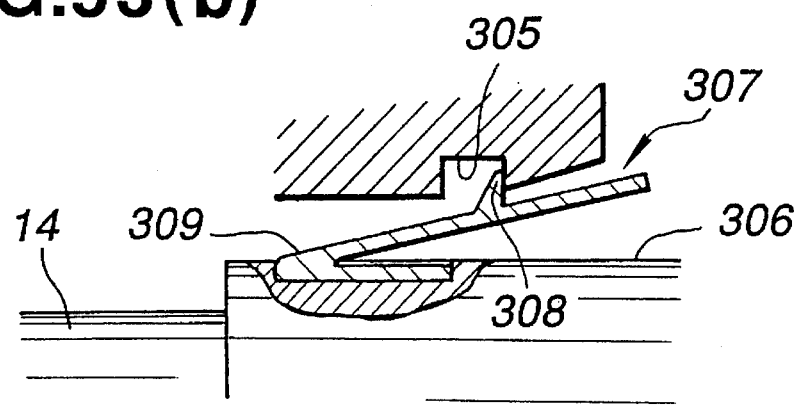
Figure 53C:
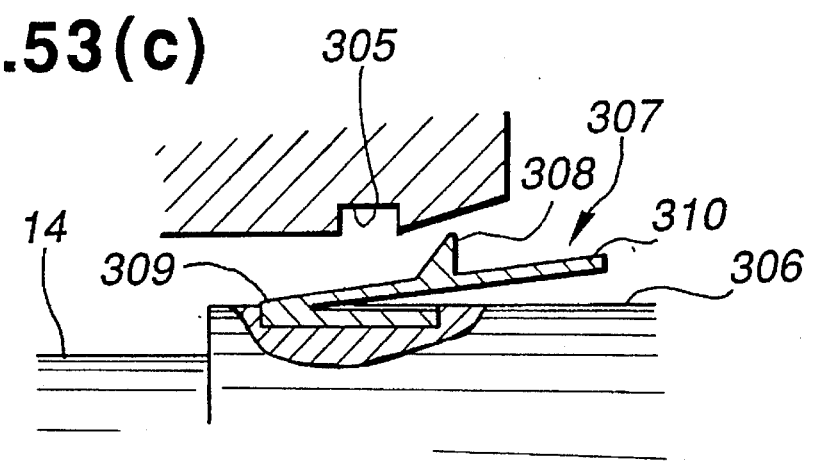

FIGS. 53(a), 53(b) and 53(c) show a state when the insertion tube cover portion 302 is fitted to the endoscope insertion tube 14. FIG. 53(a) shows a state just before the endoscope insertion tube 14 is fitted to the insertion tube cover portion 302. FIG. 53(b) shows a state when the endoscope insertion tube 14 is fitted to the insertion tube cover portion 302. FIG. 53(c) shows a state when the endoscope insertion tube 14 is pulled out from the insertion tube cover portion 302.

When the endoscope insertion tube 14 is fitted to the insertion tube cover portion 302, the proximal end portion 309 is elastically transformed by sandwiching a holding portion 310 at the end of the snap fit portion 307 from the state of FIG. 53(a) at the time of holding the cover fixing portion 306. Then, the endoscope insertion tube 14 is inserted into the insertion tube cover portion 302 by making the snap fit portion 307 fit the cover fixing portion 306.

After the endoscope insertion tube 14 is inserted the proximal end of the insertion tube cover portion 302, if an operator releases his or her hold from the holding portion 310, the click 308 of the snap fit portion 307 is engaged with the groove portion 305 of the connector for fixing the endoscope operation part 303 as shown in FIG. 53(b). At this moment, if the length of the insertion tube cover portion 302 is slightly shorter than the length of tile endoscope insertion tube 14, the insertion tube cover portion 302 is expanded and fitted to the endoscope insertion tube 14 when the endoscope insertion tube 14 is inserted. Thus, the click 308 is pushed to the side surface of the groove portion 305 by the restitution. Then, unstable installation can be prevented.

When the endoscope insertion tube 14 is pulled out from the insertion tube cover portion 302, the snap fit portion 307 is moved to the side of the cover fixing portion 306 in a state such that the holding portion 310 is sandwiched as in the same way as that of fitting the insertion tube cover portion 302, and then, the click 308 is taken off from the groove portion 305. Then, a state shown in FIG. 53(c) is made and the endoscope may be pulled out from the insertion tube cover 302.

Next, the packing of the insertion tube cover portion 222 will be explained.

Figure 54:
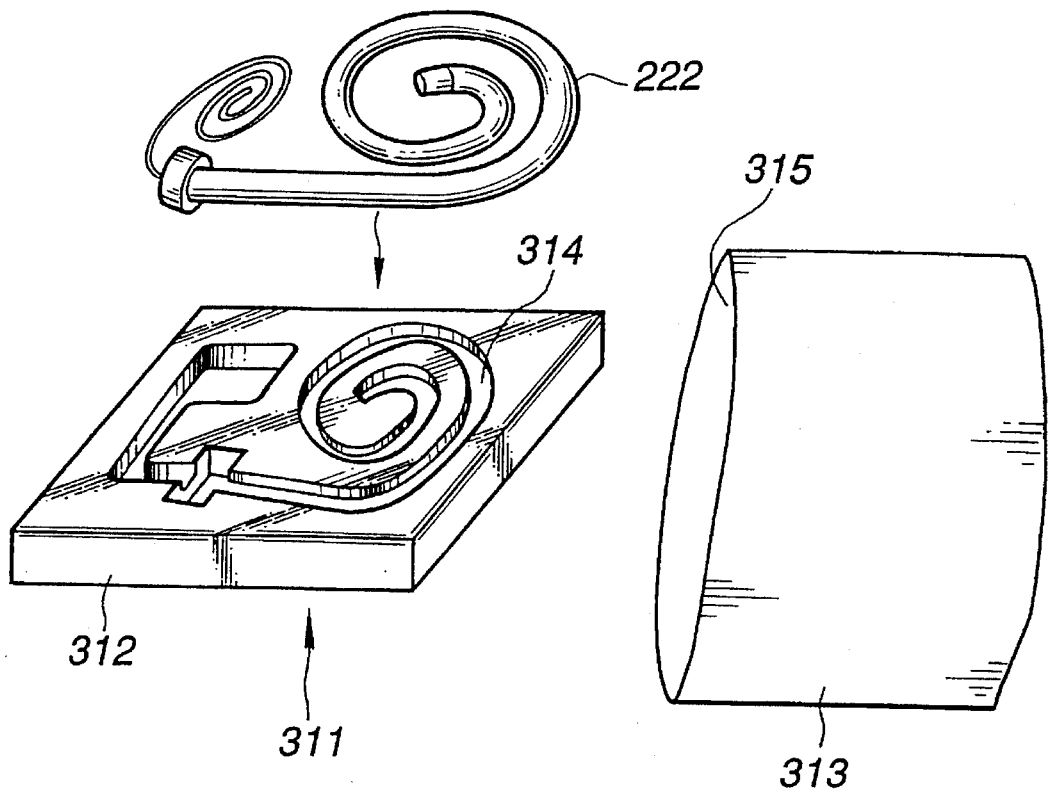

When the insertion tube cover portion 222 is packed, packing material 311 shown in FIG. 54 is used.

The packing material 311 comprises a tray 312 for putting the insertion tube cover portion 222 away in a state in which the insertion tube cover portion 222 is coiled and a package 313 for packing the insertion tube cover portion 222 in a state in which the insertion tube cover portion 222 is put in the tray 312. The package 313 is made of polymer material or paper having a hole of which diameter is about 0.2 μm that does not let a bacteria through.

A spiral groove 314 is formed in the tray 312 for putting the insertion tube cover portion 222 away in a predetermined shape. At the same time, the package 313 has an opening portion 315 and is formed to seal up the tray 312 after put away. Also, the packing material 311 may make the operation part cover portion 223 and universal cord cover portion 224 put away with the insertion tube cover portion 222.

When the insertion tube cover portion 222 is packed in the packing material 311, the insertion tube cover portion 222 is put away in a coiled and bent state along the spiral groove 314 in the tray. The tray 312 is put in the package 313 of the opening portion 315 and the opening portion 315 is sealed up. The packing material 311 in which the insertion tube cover portion 222 is contained in this state is thrown into a disinfection device and shipped after disinfected.

When the insertion tube cover portion 222 packed in this manner is fitted to the endoscope to be covered 204A, first of all, the connector for fixing the endoscope operation part 230 of the insertion tube cover portion 222 is fitted to the cover holder 206A and the expanding tube 34 is connected to the expanding tube connector 168. The endoscope insertion tube 14 is inserted into an endoscope insertion channel 225 in this state. In this way, the fitting of the insertion tube cover portion 222 to the endoscope to be covered 204A is completed.

Figure 55:
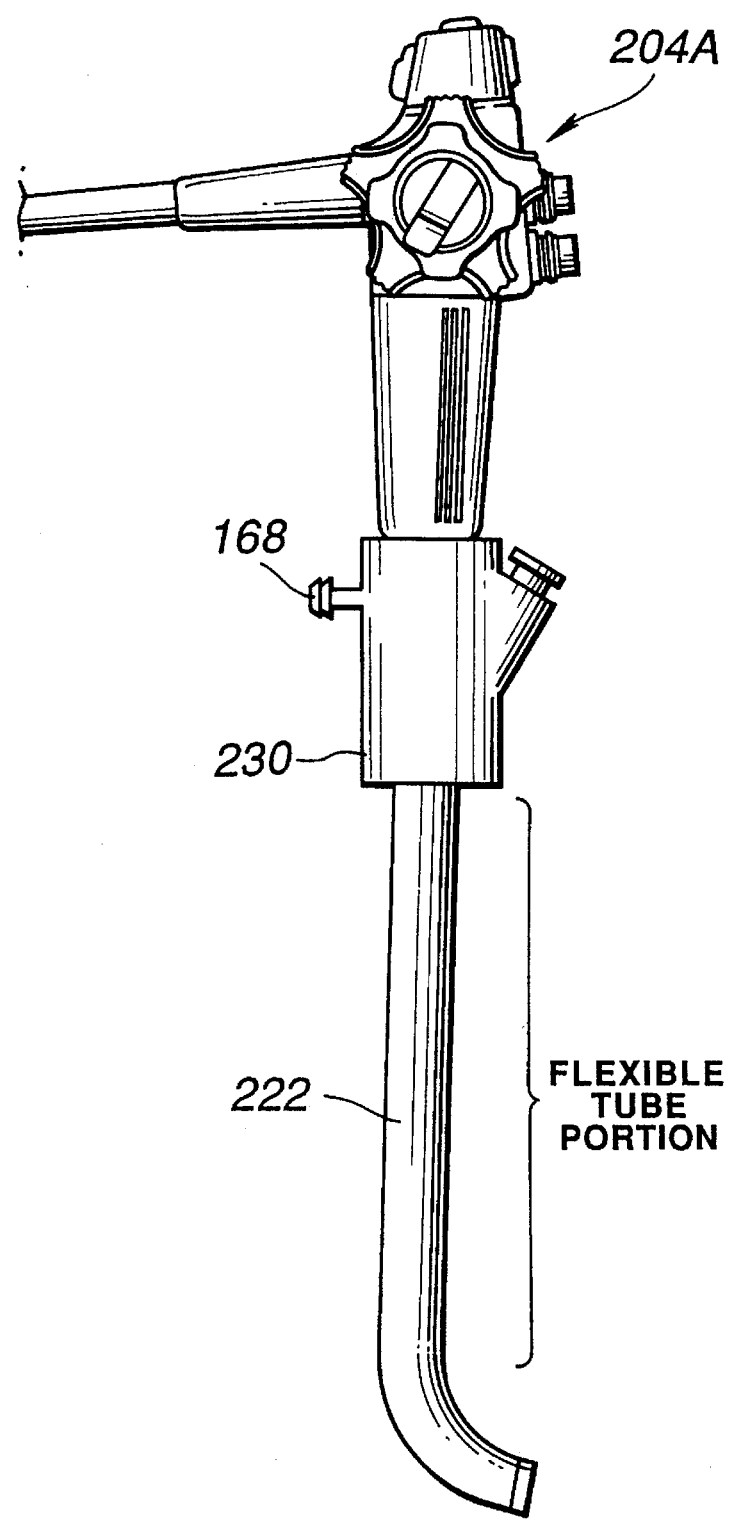

FIG. 55 shows a state in which the insertion tube cover portion 222 is fitted to the insertion tube 14 of the endoscope to be covered 204A. The channels provided in the insertion tube cover portion 222, that is, the endoscope insertion channel 225, fluid channels 226 and sucking channel 228 have multilayer structure. The channels have excellent restitutive capacity and are hard to be bent shapes. Therefore, a bent shape of a cover which has been formed is reformed by elasticity of the flexible tube portion 18 of the endoscope insertion tube 14 in a state in which the insertion tube cover portion 222 is fitted to the endoscope insertion tube 14. As shown in FIG. 55, the part corresponding to a flexible tube portion 18 becomes almost straight when the insertion tube of the endoscope apparatus of an endoscope cover type is hung down in the vertical direction.

As the aforesaid embodiment, the channel provided in the insertion tube cover portion is formed as high restitutive capacity, so that the insertion tube cover portion can be hard to be formed into a bent shape even in the case in which the insertion tube cover portion is packed in a coiled and bent state. Accordingly, it can prevent the insertion tube cover portion of the endoscope apparatus fitting an insertion tube cover portion from forming a bent shape and can remove a bad influence upon the insertability to the object position to be examined. Thus, the insertion tube cover capacity of fitting to an endoscope can be improved.

The insertion tube cover of the second endoscope of a cover type 202B which is inserted through a forceps channel of the endoscope to be covered 204A will be explained.

In such an endoscope apparatus of a parent and child scope type, when a child scope is used, an endoscope cover 203B is fitted to the second endoscope to be covered 204B which is a child scope in the same manner as that of the endoscope to be covered 204A which is a parent scope. Then, the endoscope apparatus of a parent and child scope type is used as the second endoscope of a cover type 202B.

Figure 56:
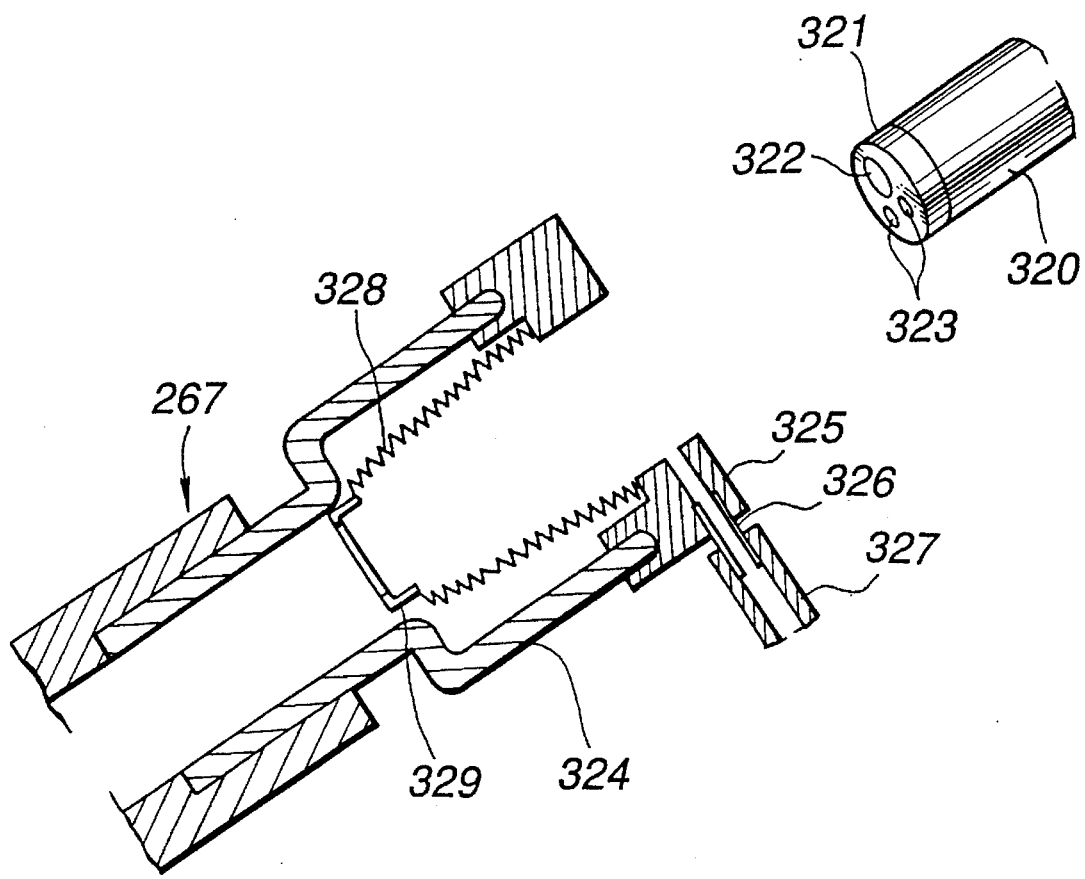
FIG. 56 is a sectional explanatory diagram showing construction of the first example of an insertion tube cover for a child scope which covers the second endoscope of a cover type.
Figure 57:
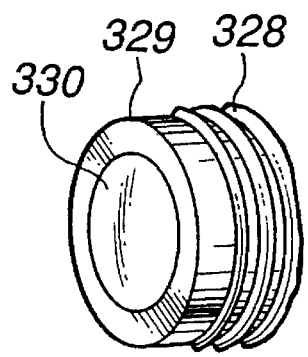
FIG. 57 is a perspective view showing construction of the tip of the insertion tube cover for the child scope shown in FIG. 56.

The construction of the first example of a child scope insertion tube cover which covers the second endoscope 202B of a cover type is shown in FIGS. 56 and 57.

A forceps insertion entrance 267 is provided at the connector for fixing the endoscope operation part 230 at the proximal end portion of the insertion tube cover portion 222 which is fitted to the endoscope to be covered 204A. An insertion tube 320 of the second endoscope to be covered 204B is inserted from the forceps insertion entrance 267. An observation optical system 322 and illumination optical system 323 are provided at a tip portion 321 of the insertion tube 320 of the second endoscope to be covered, so that a subject image can be observed by irradiating light on the position to be examined.

A child scope insertion connector 324 is connected to the forceps insertion entrance 267. An expanding connector 325 is provided at the tip of the child scope insertion connector 324. A child scope expanding tube 327 is connected to the expanding connector 325 through an expanding tube connecting tube 326. An endoscope cover expander 10 is connected to the other end of the child scope expanding tube 327. Thus, when a cover is fitted to or pulled out from the second endoscope to be covered 204B, the cover is expanded.

A child scope insertion tube cover 328 made of thin and soft polymer material which covers the insertion tube of the second endoscope to be covered 320 is folded and contained in the inside of the child scope insertion connector 324. The proximal end portion of the child scope insertion tube cover 328 is connected to the child scope insertion connector 324. A cover tip portion 329 of the child scope insertion tube cover 328 is made of hard resin or the like. As shown in FIG. 57, an observation window 330 made of transparent resin or lens is provided at the cover tip portion 329.

Figure 58:
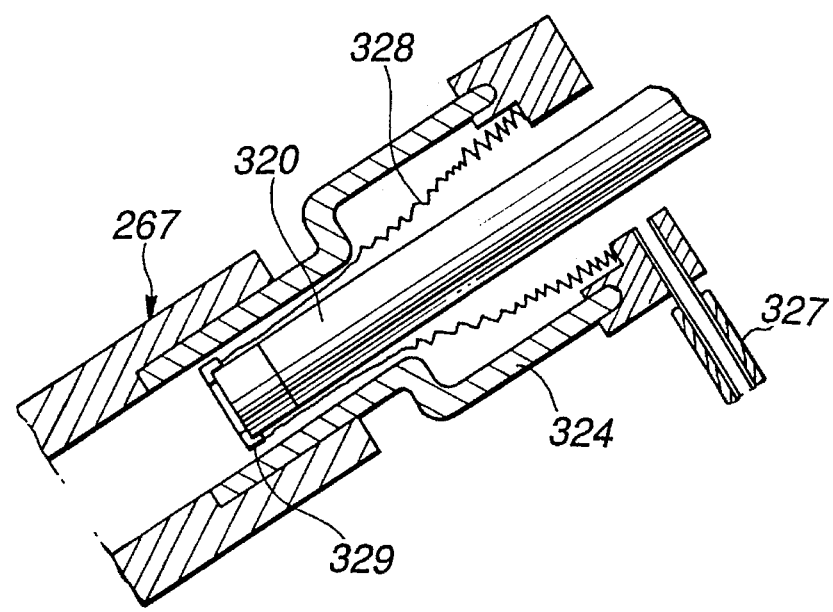
FIG. 58 is a sectional view showing a state when an insertion tube of the second endoscope to be covered is inserted into a forceps insertion entrance having an insertion tube cover for the first example of a child scope.

When the insertion tube of the second endoscope to be covered 320 is inserted into the forceps insertion entrance 267, as shown in FIG. 58, the child scope cover tip portion 329 and insertion tube tip portion 321 are joined. When the insertion tube 320 is further inserted into a forceps channel, the folded part of the child scope insertion tube cover 328 is expanded to cover the insertion tube of the second endoscope to be covered 320. At this moment, air is supplied from the child scope expanding tube 327 connected to the expander 10 into the child scope insertion tube cover 328, so that the insertion tube 320 of the second endoscope to be covered is easily inserted into the channel and easily covered with the insertion tube cover 328.

If the endoscope apparatus of an endoscope cover type is used as a parent and child scope type, it is the general construction where the parent scope to which the child scope is inserted and the child scope are separately covered and then, the covered child scope is inserted into the forceps entrance of the parent scope. Therefore, the time for covering two endoscopes is needed. Thus, there was a problem in that a lot of time and labor were spent.

At the same time, in the construction of this embodiment, the child scope insertion tube cover 328 automatically covers the insertion tube 320 only by inserting the insertion tube of the second endoscope to be covered 320, which is a child scope, into the forceps channel. Therefore, when the child scope is used, it is sufficient that only an operation part cover portion 223B and universal cord cover portion 224B are fitted before insertion. Because no time is needed to fit the child scope insertion tube cover is needed, the burden of an operator can be reduced. In addition, the labor for fitting covers can be saved and maneuverability can be improved.

When the cover is inserted into the forceps channel to fit a cover on the second endoscope to be covered, there is no fear that the child scope insertion tube cover is contaminated because an operator does not touch tile child insertion tube cover.

Figure 59:
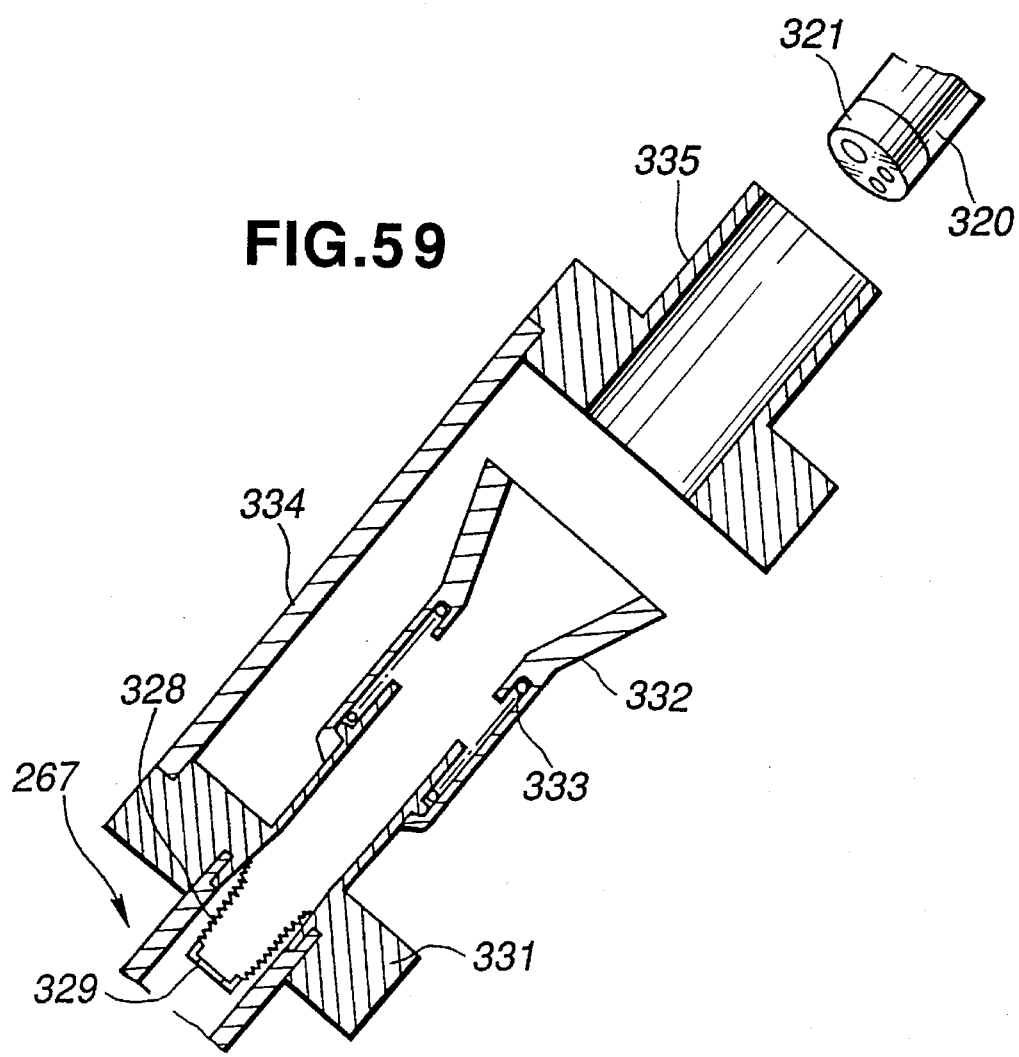
FIG. 59 is a sectional explanatory diagram showing construction of the second example of an insertion tube cover for a child scope which covers the second endoscope of a cover type.
Figure 60:
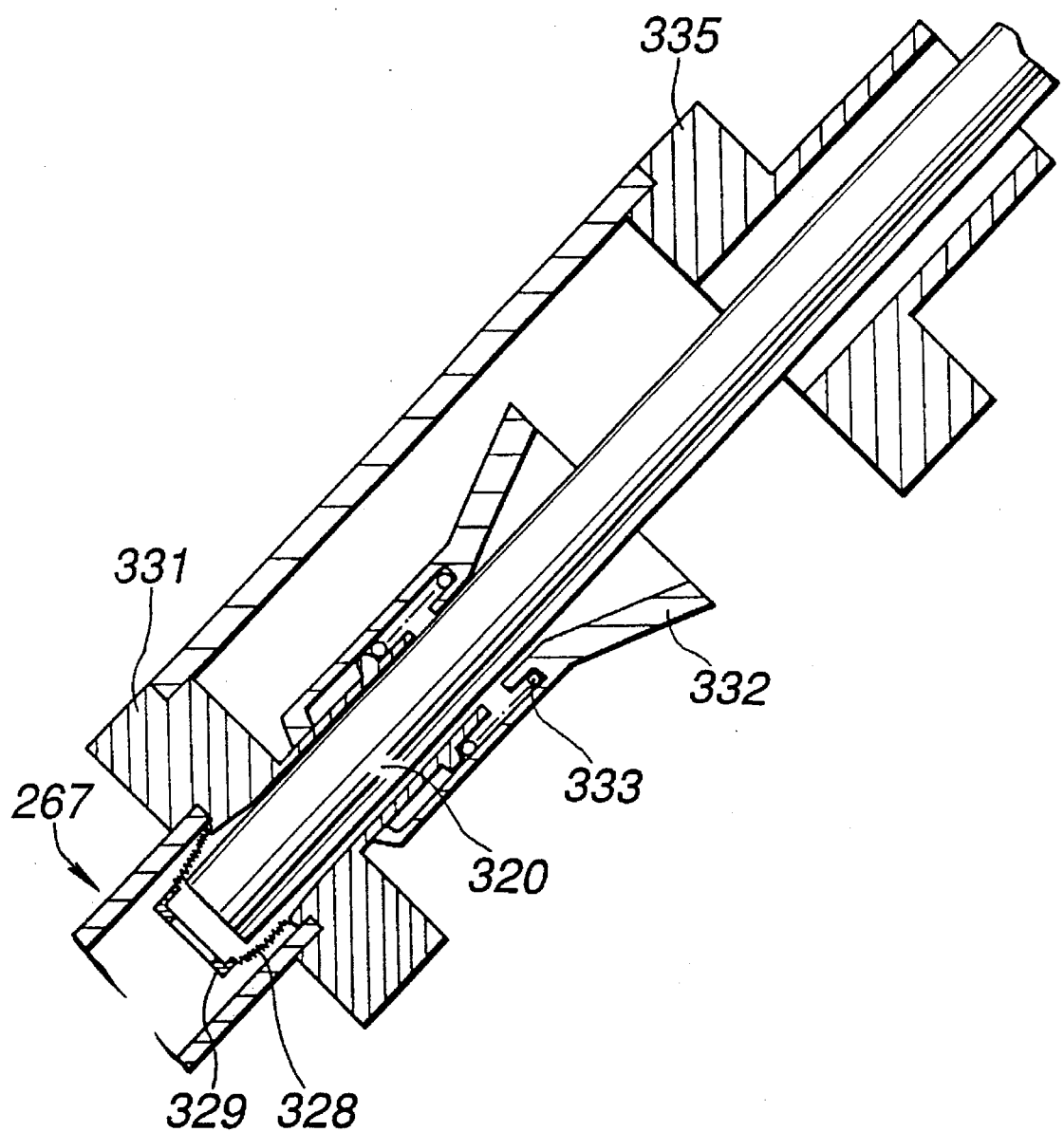
FIG. 60 is a sectional view showing a state when an insertion tube of the second endoscope to be covered is inserted into a forceps insertion entrance having an insertion tube cover for the second example child scope.

FIGS. 59 and 60 show the construction of the second example of the child scope insertion tube cover which covers a second endoscope of a cover type 202B. The second example of the child scope insertion tube cover is a construction example which does not use the expander 10 at the time of insertion and pulling out.

A forceps entrance connector 331 is detachably connected to the forceps insertion entrance 267. A child scope insertion connector 332 is fitted to the forceps entrance connector 331. The proximal end of the child scope insertion connector 332 can move in the axis direction and spreads like a taper shape. A spring member 333 for applying force to the child scope insertion entrance connector 332 to the rear side is provided at a joint of the child scope insertion connector 332 and forceps entrance connector 331.

On the surface of the forceps entrance connector 331, a supporting rod 334 is provided in the rear direction. A cylindrical child scope guiding auxiliary instrument 335 is provided at the tip of the supporting rod 334.

In the same way as the first example shown in FIG. 56, the child scope insertion tube cover 328 made of thin and soft polymer material, such as vinyl chloride which covers the insertion tube of the second endoscope to be covered 320 is folded and contained in the inside of the forceps entrance connector 331. The proximal end portion of the child scope insertion cover 328 is connected to the forceps entrance connector 331. A cover tip portion 329 made of hard resin or the like is connected to the child scope insertion tube cover 328.

When the insertion tube of the second endoscope to be covered 320 is inserted into the forceps insertion entrance 267, as shown in FIG. 60, the insertion tube 320 is guided to the child scope insertion connector 332 in a straight line by the child scope guiding auxiliary instrument 335. When the insertion tube 320 is further pushed, the insertion tube 320 is inserted into the child scope insertion connector 332 and then, inserted into the forceps insertion entrance 267 while the pushing force is adjusted by the spring member 333 provided between the child scope insertion connector 332 and the forceps entrance connector 331.

In the same way as the first example, the child scope cover tip portion 329 and insertion tube portion 321 are joined. When the insertion tube 320 is further pushed into the forceps channel, the folded part of the child scope insertion cover 328 is expanded to cover the insertion tube 320 of the second endoscope to be covered.

By forming the child scope insertion tube cover in this way, pushing force is adjusted when the insertion tube 320 of the second endoscope to be covered is inserted into the forceps insertion entrance 267 in addition to the aforesaid first example's effect. Therefore, there is an effect to reduce the fear in which the narrow insertion tube of the second endoscope to be covered is bent and transformed in the horizontal direction.

Figure 61:
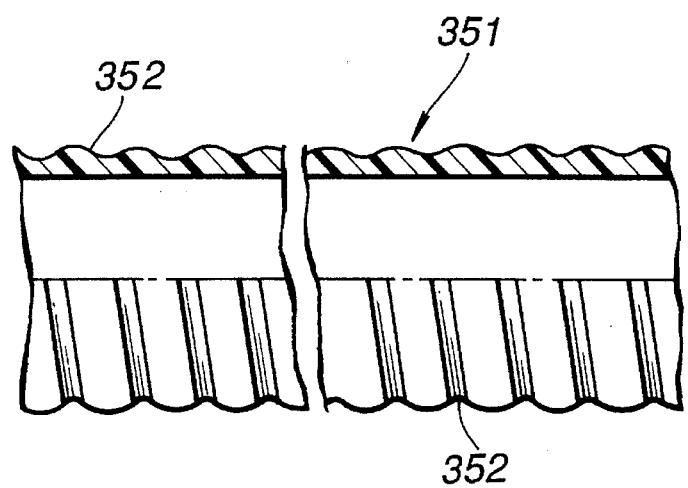
FIG. 61 is an explanatory diagram showing construction of a channel provided in an insertion tube cover portion of an endoscope cover related to the sixth embodiment of the present invention.

FIG. 61 is an explanatory diagram showing the construction of the channels provided in the insertion tube cover portion of the endoscope cover related to the sixth embodiment of the present invention.

The construction of channels, such as fluid channels 226, sucking channel 228 and endoscope insertion channel 225 which are provided in the insertion tube cover portion 222 of the endoscope cover 203A is changed in the sixth to eighth embodiments.

Channels 351 forming fluid channels 226, sucking channel 228 and endoscope insertion channel 225 of the sixth embodiment are made of PTFE tube or the like as shown in FIG. 61. A groove 352 is spirally formed on the outer circumference surface.

Because the groove 352 is spirally formed on the outer circumference in this way, the restitutive capacity of the channels increases. Even in a case in which the insertion tube cover portion is packed as a state where the cover portion is coiled and bent, the insertion tube cover portion can be made to be hard to form a bent shape. Thus, it can prevent the insertion tube of the endoscope apparatus fitting the insertion tube cover portion from forming a bent shape and also prevent the insertability to an object position to be examined from becoming worse.

Figure 62:
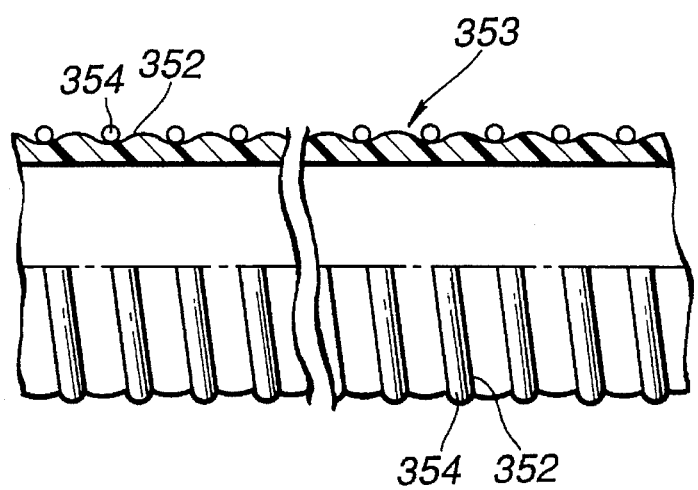
FIG. 62 is an explanatory diagram showing construction of a channel provided in an insertion tube cover portion of an endoscope cover related to the seventh embodiment of the present invention.

FIG. 62 is an explanatory diagram showing the construction of the channels provided in the insertion tube cover portion of the endoscope cover related to the seventh embodiment of the present invention.

Channels 353 forming fluid channels 226, sucking channel 228 and endoscope insertion channel 225 of the seventh embodiment are made of PTFE tube or the like as shown in FIG. 62 in the same way as that of the sixth embodiment. A groove 352 is spirally formed on the outer circumference surface. Further, a coil 354 is bound along the groove 352 in the channels 353.

In this way, by binding the coil 354 in addition to the construction of the sixth embodiment, the restitutive capacity of the channels increases. Even in a case in which the insertion tube cover portion is packed as a state where the insertion tube cover portion is coiled and bent, the insertion tube cover portion can be made to be hard to form a bent shape.

Figure 63:
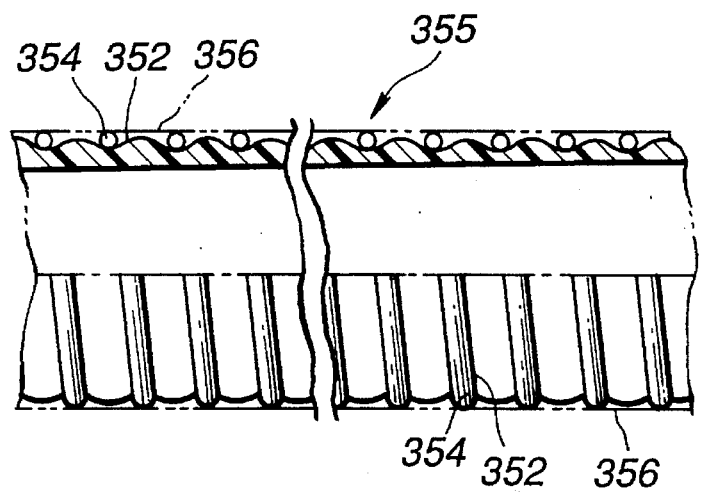
FIG. 63 is an explanatory view showing construction of a channel provided in an insertion tube cover portion of an endoscope cover related to the eighth embodiment of the present invention.

FIG. 63 is an explanatory diagram showing the construction of the channels provided in the insertion tube cover portion of the endoscope cover related to the eighth embodiment of the present invention.

Channels 355 forming fluid channels 226, sucking channel 228 and endoscope insertion channel 225 of the eighth embodiment are made of PTFE tube or the like as shown in FIG. 63 in the same way as that of the seventh embodiment. A groove 352 is spirally formed on the outer circumference surface and coil 354 is bound along the groove 352. Further, the outer circumference of the channels 355 which are bound by the coil 354 is covered with elastic resin 356.

In this way, by covering the outer circumference with the elastic resin 356 in addition to the construction of the seventh embodiment, the restitutive capacity of the channels increases. Even in a case in which the insertion tube cover portion is packed as a state where the insertion tube cover portion is coiled and bent, the insertion tube cover portion can be made to be hard to form a bent shape.

The aforesaid channels forming the fluid channels 226, sucking channel 228 and endoscope insertion channel 225 can be made of not only PTFE tube but also vinyl chloride and fluororubber as modifications.

In the present invention, it is apparent that working modes different in a wide range can be formed on the basis of the invention without departing from the spirit and scope of the invention. This invention is not restricted by its specific working mode except that it is limited by the appended claims.

What is claimed is:

1. An endoscope apparatus of an endoscope cover type comprising:

an endoscope having a long and narrow insertion tube, said insertion tube containing an optical system within said insertion tube for obtaining an endoscope image; and an endoscope cover covering at least the insertion tube of said endoscope, said endoscope cover containing a channel outside said insertion tube and extending in a longitudinal direction of said insertion tube, wherein flexibility of said endoscope cover varies in a direction of a longitudinal axis of the insertion tube.

2. An endoscope apparatus of an endoscope cover type comprising:

an endoscope having a long and narrow insertion tube, said insertion tube containing an optical system within said insertion tube for obtaining an endoscope image; and an endoscope cover covering at least the insertion tube of said endoscope, said endoscope cover containing a channel outside said insertion tube and extending in a longitudinal direction of said insertion tube, wherein, the insertion tube of said endoscope contains a plurality of kinds of thermoplastic elastomer having different degrees of hardness which are present in a mixed percentage such that the insertion tube has an increased percentage of low hardness thermoplastic elastomer in a distal end portion and an increased percentage of high hardness thermoplastic elastomer in a proximal end portion, in order to effect a change in the flexibility of the exterior portion of said insertion tube in the direction of the longitudinal axis of the insertion tube.

3. An endoscope apparatus of an endoscope cover type comprising:

an endoscope having a long and narrow insertion tube, said insertion tube containing an optical system within said insertion tube for obtaining an endoscope image; and an endoscope cover covering at least the insertion tube of said endoscope, said endoscope cover containing a channel outside said insertion tube and extending in a longitudinal direction of said insertion tube, wherein flexibility of the insertion tube of said endoscope cover continuously varies in a direction of a longitudinal axis of the insertion tube.

* * * * *